(12) United States Patent
Woo et al.

(10) Patent No.: US 9,688,976 B2
(45) Date of Patent: Jun. 27, 2017

(54) **TRANSFORMED *SYNECHOCOCCUS ELONGATUS* HAVING CAPABILITY OF PRODUCING ACETONE FROM CARBON DIOXIDE**

(71) Applicant: Korea Institute of Science and Technology, Seoul (KR)

(72) Inventors: Han Min Woo, Seoul (KR); Youngsoon Um, Seoul (KR); Jun Won Chwa, Seoul (KR); Gyeongtaek Gong, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 15/057,551

(22) Filed: Mar. 1, 2016

(65) Prior Publication Data

US 2016/0257966 A1    Sep. 8, 2016

(30) Foreign Application Priority Data

Mar. 4, 2015    (KR) .......................... 10-2015-0030616

(51) Int. Cl.
| | |
|---|---|
| *C12P 7/28* | (2006.01) |
| *C12N 15/09* | (2006.01) |
| *C12N 9/88* | (2006.01) |
| *C12N 9/00* | (2006.01) |
| *C12N 9/10* | (2006.01) |

(52) U.S. Cl.
CPC ................ *C12N 9/88* (2013.01); *C12N 9/13* (2013.01); *C12N 9/93* (2013.01); *C12Y 208/03009* (2013.01); *C12Y 401/01004* (2013.01); *C12Y 602/01001* (2013.01); *Y02P 60/247* (2015.11)

(58) Field of Classification Search
CPC .................................... C12P 7/28; C12N 15/09
USPC ...................................................... 435/252.3
See application file for complete search history.

(56) References Cited

U.S. PATENT DOCUMENTS

| 2011/0212498 A1 | 9/2011 | Hellingwerf et al. |
| 2012/0101304 A1 | 4/2012 | Becker et al. |
| 2014/0363847 A1 | 12/2014 | Fujii et al. |

FOREIGN PATENT DOCUMENTS

JP        2012-524529 A        10/2012

OTHER PUBLICATIONS

Lee, Taek Soon, et al. "BglBrick Vectors and Datasheets: A Synthetic Biology Platform for Gene Expression." *Journal of biological engineering* 5.12 (2011). (14 pages, in English).
Zhou, Jie, et al. "Designing and Creating a Modularized Synthetic Pathway in Cyanobacterium *Synechocystis* Enables Production of Acetone From Carbon Dioxide." *Metabolic engineering* 14.4 (2012): 394-400. (7 pages, in English).
Kusakabe, Tamami, et al. "Engineering a Synthetic Pathway in Cyanobacteria for Isopropanol Production Directly From Carbon Dioxide and Light." *Metabolic engineering* 20 (2013): 101-108. (8 pages, in English).
Hirokawa, Yasutaka, et al. "Optimization of Isopropanol Production by Engineered Cyanobacteria With a Synthetic Metabolic Pathway." *Journal of Bioscience and Bioengineering* 119.5 (2015). (6 pages, in English).

*Primary Examiner* — Maryam Monshipouri
(74) *Attorney, Agent, or Firm* — NSIP Law

(57) ABSTRACT

Disclosed herein are a transformed *Synechococcus elongatus* strain having improved capability of producing acetone and a method for producing acetone and a method for removing carbon dioxide using the same. In an aspect, the transformed *Synechococcus elongatus* strain of the present disclosure can produce acetone with high selectivity using carbon dioxide as a carbon source. The present disclosure is economical because the *Synechococcus elongatus* strain can economically produce high value-added acetone using carbon dioxide existing in the atmosphere as a carbon source without requiring an additional catalytic reaction. Also, the present disclosure is environment-friendly because carbon dioxide in the atmosphere can be removed or reduced using the microorganism.

8 Claims, 35 Drawing Sheets

Fig. 6

```
atgaaaaact gcgtgatcgt gagcgccgtg cgcaccgcca tcggcagctt taacggcagc
ctggccagca ccagcgccat cgatctgggc gccaccgtga tcaaagccgc catcgaacgc
gccaaaatcg atagccagca cgtggatgaa gtgatcatgg gcaacgtgct ccaggccggc
ctgggccaga accccgcccg ccaggccctg ctgaaaagcg gcctggccga accgtgtgc
ggctttaccg tgaacaaagt gtgcggcagc ggcctgaaaa gcgtggccct ggccgcccag
gccatccagg ccggccaggc ccagagcatc gtggccggcg catggaaaa catgagcctg
gcccctacc tgctggatgc caaagcccgc agcggctacc gctgggcga tggccaggtg
tacgatgtga tcctgcgcga tggcctgatg tgcgccaccc acggctacca catgggcatc
accgccgaaa acgtggccaa agaatacggc atcacccgcg aaatgcagga tgaactggcc
ctgcacagcc agcgcaaagc cgccgccgcc atcgaaagcg gcgcctttac cgccgaaatc
gtgcccgtga acgtggtgac ccgcaaaaaa acctttgtgt tagccagga tgaatttccc
aaagccaaca gcaccgccga agccctgggc gccctgcgcc ccgcctttga taaagccggc
accgtgaccg ccggcaacgc cagcggcatc aacgatggcg ccgccgccct ggtgatcatg
gaagaaagcg ccgccctggc cgccggcctg acccccctgg cccgcatcaa aagctacgcc
agcggcggcg tgcccccgc cctgatgggc atgggccccg tgcccgccac ccagaaagcc
ctccagctgg ccggcctcca gctggccgat atcgatctga tcgaagccaa cgaagccttt
gccgcccagt ttctggccgt gggcaaaaac ctgggctttg atagcgaaaa agtgaacgtg
aacggcggcg ccatcgccct gggccacccc atcggcgcca gcggcgcccg catcctggtg
accctgctgc acgccatgca ggcccgcgat aaaaccctgg gcctggccac cctgtgcatc
ggcggcggcc agggcatcgc catggtgatc gaacgcctga actag
```

Fig. 7 atgaccgatg tgcgctttcg catcatcggc accggcgcct acgtgcccga acgcatcgtg
agcaacgatg aagtgggcgc ccccgccggc gtggatgatg attggatcac ccgcaaaacc
ggcatccgcc agcgccgctg ggccgccgat gatcaggcca ccagcgatct ggccaccgcc
gccggccgcg ccgccctgaa agccgccggc atcaccccg aacagctgac cgtgatcgcc
gtggccacca gcaccccga tcgcccccag cccccaccg ccgcctacgt gcagcaccac
ctgggcgcca ccggcaccgc cgcctttgat gtgaacgccg tgtgcagcgg caccgtgttt
gccctgagca gcgtggccgg caccctggtg taccgcggcg gctacgccct ggtgatcggc
gccgatctgt acagccgcat cctgaacccc gccgatcgca aaaccgtggt gctgtttggc
gatggcgccg gcgccatggt gctgggcccc accagcaccg gcaccggccc catcgtgcgc
cgcgtggccc tgcacacctt tggcggcctg accgatctga tccgcgtgcc cgccggcggc
agccgccagc ccctggatac cgatggcctg gatgccggcc tgcagtactt tgccatggat
ggccgcgaag tgcgccgctt tgtgaccgaa cacctgcccc agctgatcaa aggctttctg
cacgaagccg gcgtggatgc cgccgatatc agccactttg tgccccacca ggccaacggc
gtgatgctgg atgaagtgtt tggcgaactg cacctgcccc gcgccaccat gcaccgcacc
gtggaaacct acggcaacac cggcgccgcc agcatcccca tcaccatgga tgccgccgtg
cgcgccggca gctttcgccc cggcgaactg gtgctgctgg ccggctttgg cggcggcatg
gccgccagct ttgccctgat cgaatggtag

Fig. 8 atgaaaacca aactgatgac cctccaggat gccaccggct tttttcgcga tggcatgacc
atcatggtgg gcggctttat gggcatcggc accccagcc gcctggtgga agccctgctg
gaaagcggcg tgcgcgatct gaccctgatc gccaacgata ccgcctttgt ggataccggc
atcggccccc tgatcgtgaa cggccgcgtg cgcaaagtga tcgccagcca catcggcacc
aaccccgaaa ccggccgccg catgatcagc ggcgaaatgg atgtggtgct ggtgcccag
ggcaccctga tcaacagat ccgctgcggc ggcgccggcc tgggcggctt tctgaccccc
accggcgtgg gcaccgtggt ggaagaaggc aaacagaccc tgaccctgga tggcaaaacc
tggctgctgg aacgcccct gcgcgccgat ctggccctga tccgcgccca ccgctgcgat
accctgggca acctgaccta ccagctgagc gccgcaact taaccccct gatcgccctg
gccgccgata tcaccctggt ggaacccgat gaactggtgg aaaccggcga actccagccc
gatcacatcg tgaccccgg cgccgtgatc gatcacatca tcgtgagcca ggaaagcaaa
tagttaaaga ggagaatact agatggatgc caaacagcgc atcgcccgcc gcgtggccca
ggaactgcgc gatggcgata tcgtgaacct gggcatcggc ctgcccacca tggtggccaa
ctacctgccc gaaggcatcc acatcaccct ccagagcgaa aacggctttc tgggcctggg
ccccgtgacc accgcccacc ccgatctggt gaacgccggc ggccagcct gcggcgtgct
gcccggcgcc gccatgtttg atagcgccat gagctttgcc ctgatccgcg gcggccacat
cgatgcctgc gtgctgggcg gcctccaggt ggatgaagaa gccaacctgg ccaactgggt
ggtgcccggc aaaatggtgc ccggcatggg cggcgccatg gatctggtga ccggcagccg
caaagtgatc atcgccatgg aacactgcgc caaagatggc agcgccaaaa tcctgcgccg
ctgcaccatg cccctgaccg cccagcacgc cgtgcacatg ctggtgaccg aactggccgt
gtttcgcttt atcgatggca aaatgtggct gaccgaaatc gccgatggct gcgatctggc
caccgtgcgc gccaaaaccg aagcccgctt tgaagtggcc gccgatctga acacccagcg
cggcgatctg tag

Fig. 9 atgaacagca aaatcatccg ctttgaaaac ctgcgcagct tttttaaaga tggcatgacc
atcatgatcg gcggctttct gaactgcggc accccacca aactgatcga ttttctggtg
aacctgaaca tcaaaaacct gaccatcatc agcaacgata cctgctaccc caacaccggc
atcggcaaac tgatcagcaa caaccaggtg aaaaaactga tcgccagcta catcggcagc
aaccccgata ccggcaaaaa actgtttaac aacgaactgg aagtggaact gagccccag
ggcaccctgg tggaacgcat ccgcgccggc ggcagcggcc tgggcggcgt gctgaccaaa
accggcctgg gcaccctgat cgaaaaaggc aaaaaaaaaa tcagcatcaa cggcaccgaa
tacctgctgg aactgcccct gaccgccgat atcgccctga tcaaaggcag catcgtggat
gaagccggca acaccttta caaaggcacc accaaaaact taaccccta catggccatg
gccgccaaaa ccgtgatcgt ggaagccgaa aacctggtga gctgcgaaaa actggaaaaa
gaaaaagcca tgaccccgg cgtgctgatc aactacatcg tgaaagaacc cgcctaaaat
gatcaacgat aaaaacctgg ccaaagaaat catcgccaaa cgcgtggccc gcgaactgaa
aaacggccag ctggtgaacc tgggcgtggg cctgcccacc atggtggccg attacatccc
caaaaacttt aaaatcacct tcagagcga aaacggcatc gtgggcatgg gcgccagccc
caaaatcaac gaagccgata agatgtggt gaacgccggc ggcgattaca ccaccgtgct
gcccgatggc acctttttg atagcagcgt gagctttagc ctgatccgcg gcggccacgt
ggatgtgacc gtgctgggcg ccctccaggt ggatgaaaaa ggcaacatcg ccaactggat
cgtgcccggc aaaatgctga gcggcatggg cggcgccatg gatctggtga acggcgccaa
aaaagtgatc atcgccatgc gccacaccaa caaaggccag cccaaaatcc tgaaaaaatg
caccctgccc ctgaccgcca aaagccaggc caacctgatc gtgaccgaac tgggcgtgat
cgaagtgatc aacgatggcc tgctgctgac cgaaatcaac aaaaacacca ccatcgatga
aatccgcagc ctgaccgccg ccgatctgct gatcagcaac gaactgcgcc ccatggccgt
gtag

Fig. 10 atgctgaaag atgaagtgat caaacagatc agcacccccc tgaccagccc cgcctttccc
cgcggcccct acaaatttca caaccgcgaa tactttaaca tcgtgtaccg caccgatatg
gatgccctgc gcaaagtggt gcccgaaccc ctggaaatcg atgaacccct ggtgcgcttt
gaaatcatgg ccatgcacga taccagcggc ctgggctgct acaccgaaag cggccaggcc
atccccgtga gctgcaacgg cgtgaaaggc gattacctgc acatgatgta cctggataac
gaacccgcca tcgccgtggg ccgcgaactg agcgcctacc ccaaaaaact gggctacccc
aaactgtttg tggatagcga taccctggtg ggcaccctgg attacggcaa actgcgcgtg
gccaccgcca ccatgggcta caaacacaaa gccctggatg ccaacgaagc caaagatcag
atttgccgcc ccaactacat gctgaaaatc atccccaact acgatggcag ccccgcatc
tgcgaactga tcaacgccaa atcaccgat gtgaccgtgc acgaagcctg gaccggcccc
acccgcctcc agctgtttga tcacgccatg gccccctga acgatctgcc cgtgaaagaa
atcgtgagca gcagccacat cctggccgat atcatcctgc cccgcgccga agtgatctac
gattacctga aatag

Fig. 11A

```
gataatctca tgaccaaaat cccttaacgt gagttttcgt tccactgagc gtcagacccc
gtagaaaaga tcaaaggatc ttcttgagat cctttttttc tgcgcgtaat ctgctgcttg
caaacaaaaa aaccaccgct accagcggtg gtttgtttgc cggatcaaga gctaccaact
cttttttccga aggtaactgg cttcagcaga gcgcagatac caaatactgt tcttctagtg
tagccgtagt taggccacca cttcaagaac tctgtagcac cgcctacata cctcgctctg
ctaatcctgt taccagtggc tgctgccagt ggcgataagt cgtgtcttac cgggttggac
tcaagacgat agttaccgga taaggcgcag cggtcgggct gaacggggg ttcgtgcaca
cagcccagct tggagcgaac gacctacacc gaactgagat acctacagcg tgagctatga
gaaagcgcca cgcttcccga agggagaaag gcggacaggt atccggtaag cggcagggtc
ggaacaggag agcgcacgag ggagcttcca gggggaaacg cctggtatct ttatagtcct
gtcgggtttc gccacctctg acttgagcgt cgatttttgt gatgctcgtc aggggggcgg
agcctatgga aaaacgccag caacgcggcc ttttttacggt tcctggcctt ttgctggcct
tttgctcaca tgtgtgctgg gccccaatgc cttctccaag ggcggcattc ccctgactgt
tgaaggcgtt gccaatatca agattgctgg ggaagaaccg accatccaca acgcgatcga
gcggctgctt ggcaaaaacc gtaaggaaat cgagcaaatt gccaaggaga ccctcgaagg
caacttgcgt ggtgttttag ccagcctcac gccggagcag atcaacgagg acaaaattgc
ctttgccaaa agtctgctgg aagaggcgga ggatgaccct gagcagctgg gtctagtcct
cgatacgctg caagtccaga acatttccga tgaggtcggt tatctctcgg ctagtggacg
caagcagcgg gctgatctgc agcgagatgc ccgaattgct gaagccgatg cccaggctgc
ctctgcgatc caaacggccg aaaatgacaa gatcacggcc ctgcgtcgga tcgatcgcga
tgtagcgatc gcccaagccg aggccgagcg ccggattcag gatgcgttga cgcggcgcga
agcggtggtg gccgaagctg aagcggacat tgctaccgaa gtcgctcgta gccaagcaga
actccctgtg cagcaggagc ggatcaaaca ggtgcagcag caacttcaag ccgatgtgat
cgccccagct gaggcagctt gtaaacgggc gatcgcggaa gcgcggggg ccgccgcccg
tatcgtcgaa gatggaaaag ctcaagcgga agggacccaa cggctggcgg aggcttggca
gaccgctggt gctaatgccc gcgacatctt cctgctccag aagtctagac cagccaggac
agaaatgcct cgacttcgct gctacccaag gttgccgggt gacgcacacc gtggaaacgg
atgaaggcac gaacccagtg gacataagcc tgttcggttc gtaagctgta atgcaagtag
cgtatgcgct cacgcaactg gtccagaacc ttgaccgaac gcagcggtgg taacggcgca
gtggcggttt tcatggcttg ttatgactgt ttttttgggg tacagtctat gcctcgggca
tccaagcagc aagcgcgtta cgccgtgggt cgatgtttga tgttatggag cagcaacgat
gttacgcagc agggcagtcg ccctaaaaca aagttaaaca ttatgaggga agcggtgatc
gccgaagtat cgactcaact atcagaggta gttggcgtca tcgagcgcca tctcgaaccg
acgttgctgg ccgtacattt gtacggctcc gcagtggatg gcggcctgaa gccacacagt
gatattgatt tgctggttac ggtgaccgta aggcttgatg aaacaacgcg gcgagctttg
atcaacgacc ttttggaaac ttcggcttcc cctggagaga gcgagattct ccgcgctgta
gaagtcacca ttgttgtgca cgacgacatc attccgtggc gttatccagc taagcgcgaa
```

Fig. 11B

```
ctgcaatttg gagaatggca gcgcaatgac attcttgctg gtatcttcga gccagccacg
atcgacattg atctggctat cttgctgaca aaagcaagag aacatagcgt tgccttggta
ggtccagcgg cggaggaact ctttgatccg gttcctgaac aggatctatt tgaggcgcta
aatgaaacct taacgctatg gaactcgccg cccgactggg ctggcgatga gcgaaatgta
gtgcttacgt tgtcccgcat ttggtacagc gcagtaaccg gcaaaatcgc gccgaaggat
gtcgctgccg actgggcaat ggagcgcctg ccggcccagt atcagcccgt catacttgaa
gctagacagg cttatcttgg acaagaagaa gatcgcttgg cctcgcgcgc agatcagttg
gaagaatttg tccactacgt gaaaggcgag atcaccaagg tagtcggcaa ataacctcat
tttcgccaga tatcgacgtc gacaccatcg aatggtgcaa aacctttcgc ggtatggcat
gatagcgccc ggaagagagt caattcaggg tggtgaatgt gaaaccagta acgttatacg
atgtcgcaga gtatgccggt gtctcttatc agaccgtttc ccgcgtggtg aaccaggcca
gccacgtttc tgcgaaaacg cgggaaaaag tggaagcggc gatggcggag ctgaattaca
ttcccaaccg cgtggcacaa caactggcgg gcaaacagtc gttgctgatt ggcgttgcca
cctccagtct ggccctgcac gcgccgtcgc aaattgtcgc ggcgattaaa tctcgcgccg
atcaactggg tgccagcgtg gtggtgtcga tggtagaacg aagcggcgtc gaagcctgta
aagcggcggt gcacaatctt ctcgcgcaac gcgtcagtgg gctgatcatt aactatccgc
tggatgacca ggatgccatt gctgtggaag ctgcctgcac taatgttccg gcgttatttc
ttgatgtctc tgaccagaca cccatcaaca gtattatttt ctcccatgaa gacggtacgc
gactgggcgt ggagcatctg gtcgcattgg gtcaccagca aatcgcgctg ttagcgggcc
cattaagttc tgtctcggcg cgtctgcgtc tggctggctg gcataaatat ctcactcgca
atcaaattca gccgatagcg gaacgggaag gcgactggag tgccatgtcc ggttttcaac
aaaccatgca aatgctgaat gagggcatcg ttcccactgc gatgctggtt gccaacgatc
agatggcgct gggcgcaatg cgcgccatta ccgagtccgg gctgcgcgtt ggtgcggata
tctcggtagt gggatacgac gataccgaag acagctcatg ttatatcccg ccgttaacca
ccatcaaaca ggattttcgc ctgctggggc aaaccagcgt ggaccgcttg ctgcaactct
ctcagggcca ggcggtgaag ggcaatcagc tgttgcccgt ctcactggtg aaaagaaaaa
ccaccctggc gcccaatacg caaaccgcct ctccccgcgc gttggccgat tcattaatgc
agctggcacg acaggtttcc cgactggaaa gcgggcagtg agcgcaacgc aattaatgta
agttagcgcg aattgatctg gtttgacagc ttatcatcga ctgcacggtg caccaatgct
tctggcgtca ggcagccatc ggaagctgtg gtatggctgt gcaggtcgta atcactgca
taattcgtgt cgctcaaggc gcactcccgt tctggataat gttttttgcg ccgacatcat
aacggttctg gcaaatattc tgaaatgagc tgttgacaat taatcatccg gctcgtataa
tgtgtggaat tgtgagcgga taacaatttc agaattcaaa agatctttaa agaggagaat
actagatgaa aaactgcgtg atcgtgagcg ccgtgcgcac cgccatcggc agctttaacg
gcagcctggc cagcaccagc gccatcgatc tgggcgccac cgtgatcaaa gccgccatcg
aacgcgccaa aatcgatagc cagcacgtgg atgaagtgat catgggcaac gtgctccagg
ccggcctggg ccagaacccc gcccgccagg ccctgctgaa aagcggcctg gccgaaaccg
tgtgcggctt taccgtgaac aaagtgtgcg gcagcggcct gaaaagcgtg gccctggccg
cccaggccat ccaggccggc caggcccaga gcatcgtggc cggcggcatg gaaaacatga
gcctggccgg ctacctgctg gatgccaaag cccgcagcgg ctaccgcctg ggcgatggcc
aggtgtacga tgtgatcctg cgcgatggcc tgatgtgcgc cacccacggc taccacatgg
```

Fig. 11C

```
gcatcaccgc cgaaaacgtg gccaaagaat acggcatcac ccgcgaaatg caggatgaac
tggccctgca cagccagcgc aaagccgccg ccgccatcga aagcggcgcc tttaccgccg
aaatcgtgcc cgtgaacgtg gtgacccgca aaaaaacctt tgtgtttagc caggatgaat
ttcccaaagc caacagcacc gccgaagccc tgggcgccct gcgccccgcc tttgataaag
ccggcaccgt gaccgccggc aacgccagcg gcatcaacga tggcgccgcc gccctggtga
tcatggaaga aagcgccgcc ctggccgccg gcctgacccc cctggcccgc atcaaaagct
acgccagcgg cggcgtgccc cccgccctga tgggcatggg ccccgtgccc gccacccaga
aagccctcca gctggccggc ctccagctgg ccgatatcga tctgatcgaa gccaacgaag
cctttgccgc ccagtttctg gccgtgggca aaacctggg ctttgatagc gaaaaagtga
acgtgaacgg cggcgccatc gccctgggcc acccatcgg cgccagcggc gccgcatcc
tggtgaccct gctgcacgcc atgcaggccc gcgataaaac cctgggcctg gccaccctgt
gcatcggcgg cggccagggc atcgccatgg tgatcgaacg cctgaactag aagaggagaa
atactagatg aaaaccaaac tgatgaccct ccaggatgcc accggcttt ttcgcgatgg
catgaccatc atggtgggcg gctttatggg catcggcacc cccagccgcc tggtggaagc
cctgctggaa agcggcgtgc gcgatctgac cctgatcgcc aacgataccg cctttgtgga
taccggcatc ggccccctga tcgtgaacgg ccgcgtgcgc aaagtgatcg ccagccacat
cggcaccaac cccgaaaccg gccgccgcat gatcagcggc gaaatggatg tggtgctggt
gccccagggc accctgatcg aacagatccg ctgcggcggc gccggcctgg cggctttct
gacccccacc ggcgtgggca ccgtggtgga agaaggcaaa cagaccctga ccctggatgg
caaaacctgg ctgctggaac gccccctgcg cgccgatctg gccctgatcc gcgcccaccg
ctgcgatacc ctgggcaacc tgacctacca gctgagcgcc cgcaactta accccctgat
cgccctggcc gccgatatca ccctggtgga acccgatgaa ctggtggaaa ccggcgaact
ccagcccgat cacatcgtga ccccggcgc cgtgatcgat cacatcatcg tgagccagga
aagcaaatag ttaaagagga gaatactaga tggatgccaa acagcgcatc gccgccgcg
tgcccagga actgcgcgat ggcgatatcg tgaacctggg catcggcctg cccaccatgg
tggccaacta cctgcccgaa ggcatccaca tcaccctcca gagcgaaaac ggctttctgg
gcctgggccc cgtgaccacc gcccaccccg atctggtgaa cgccggcggc cagccctgcg
gcgtgctgcc cggcgccgcc atgtttgata gcgccatgag ctttgccctg atccgcggcg
gccacatcga tgcctgcgtg ctgggcggcc tccaggtgga tgaagaagcc aacctggcca
actgggtggt gcccggcaaa atggtgcccg gcatgggcgg cgccatggat ctggtgaccg
gcagccgcaa agtgatcatc gccatggaac actgcgccaa agatggcagc gccaaaatcc
tgcgccgctg caccatgccc ctgaccgccc agcacgccgt gcacatgctg gtgaccgaac
tggccgtgtt tcgctttatc gatggcaaaa tgtggctgac cgaaatcgcc gatggctgcg
atctggccac cgtgcgcgcc aaaaccgaag cccgctttga agtggccgcc gatctgaaca
cccagcgcgg cgatctgtag ggatctggat ctttaaagag gagaatacta gatgctgaaa
gatgaagtga tcaaacagat cagcaccccc ctgaccagcc ccgcctttcc ccgcggcccc
tacaaattc acaaccgcga atactttaac atcgtgtacc gcaccgatat ggatgccctg
cgcaaagtgg tgcccgaacc cctggaaatc gatgaacccc tggtgcgctt tgaaatcatg
gccatgcacg ataccagcgg cctgggctgc tacaccgaaa gcggccaggc catccccgtg
agctgcaacg gcgtgaaagg cgattacctg cacatgatgt acctggataa cgaacccgcc
atcgccgtgg gccgcgaact gagcgcctac cccaaaaaac tgggctaccc caaactgttt
```

Fig. 11D gtggatagcg ataccctggt gggcaccctg gattacggca aactgcgcgt ggccaccgcc
accatgggct acaaacacaa agccctggat gccaacgaag ccaaagatca gatttgccgc
cccaactaca tgctgaaaat catccccaac tacgatggca gccccgcat ctgcgaactg
atcaacgcca aaatcaccga tgtgaccgtg cacgaagcct ggaccggccc cacccgcctc
cagctgtttg atcacgccat ggccccctg aacgatctgc ccgtgaaaga aatcgtgagc
agcagccaca tcctggccga tatcatcctg ccccgcgccg aagtgatcta cgattacctg
aaatagctcg agtaaggatc tccaggcatc aaataaaacg aaaggctcag tcgaaagact
gggcctttcg ttttatctgt tgtttgtcgg tgaacgctct ctactagagt cacactggct
caccttcggg tgggcctttc tgcgtttata cctagggcgt tcggctgcgg cgagcggtat
cagctcactc aaaggcggta atacgtccct gctcgtcacg ctttcaggca ccgtgccaga
tatcgacgtg gagtcgatca ctgtgattgg cgaaggggaa ggcagcgcta cccaaatcgc
tagcttgctg gagaagctga aacaaaccac gggcattgat ctggcgaaat ccctaccggg
tcaatccgac tcgcccgctg cgaagtccta agagatagcg atgtgaccgc gatcgcttgt
caagaatccc agtgatccg aaccatagga aggcaagctc aatgcttgcc tcgtcttgag
gactatctag atgtctgtgg aacgcacatt tattgccatc aagcccgatg gcgttcagcg
gggtttggtc ggtacgatca tcggccgctt tgagcaaaaa ggcttcaaac tggtgggcct
aaagcagctg aagcccagtc gcgagctggc cgaacagcac tatgctgtcc accgcgagcg
ccccttcttc aatggcctcg tcgagttcat cacctctggg ccgatcgtgg cgatcgtctt
ggaaggcgaa ggcgttgtgg cggctgctcg caagttgatc ggcgctacca atccgctgac
ggcagaaccg ggcaccatcc gtggtgattt tggtgtcaat attggccgca acatcatcca
tggctcggat gcaatcgaaa cagcacaaca ggaaattgct ctctggttta gcccagcaga
gctaagtgat tggaccccca cgattcaacc ctggctgtac gaataaggtc tgcattcctt
cagagagaca ttgccatgcc c

Fig. 12A

```
gataatctca tgaccaaaat cccttaacgt gagttttcgt tccactgagc gtcagacccc
gtagaaaaga tcaaaggatc ttcttgagat cctttttttc tgcgcgtaat ctgctgcttg
caaacaaaaa aaccaccgct accagcggtg gtttgtttgc cggatcaaga gctaccaact
cttttttccga aggtaactgg cttcagcaga gcgcagatac caaatactgt tcttctagtg
tagccgtagt taggccacca cttcaagaac tctgtagcac cgcctacata cctcgctctg
ctaatcctgt taccagtggc tgctgccagt ggcgataagt cgtgtcttac cgggttggac
tcaagacgat agttaccgga taaggcgcag cggtcgggct gaacgggggg ttcgtgcaca
cagcccagct tggagcgaac gacctacacc gaactgagat acctacagcg tgagctatga
gaaagcgcca cgcttccga agggagaaag gcggacaggt atccggtaag cggcagggtc
ggaacaggag agcgcacgag ggagcttcca gggggaaacg cctggtatct ttatagtcct
gtcgggtttc gccacctctg acttgagcgt cgattttgt gatgctcgtc aggggggcgg
agcctatgga aaaacgccag caacgcggcc tttttacggt tcctggcctt ttgctggcct
tttgctcaca tgtgtgctgg gccccaatgc cttctccaag ggcggcattc ccctgactgt
tgaaggcgtt gccaatatca agattgctgg ggaagaaccg accatccaca acgcgatcga
gcggctgctt ggcaaaaacc gtaaggaaat cgagcaaatt gccaaggaga ccctcgaagg
caacttgcgt ggtgttttag ccagcctcac gccggagcag atcaacgagg acaaaattgc
ctttgccaaa agtctgctgg aagaggcgga ggatgacctt gagcagctgg gtctagtcct
cgatacgctg caagtccaga acatttccga tgaggtcggt tatctctcgg ctagtggacg
caagcagcgg gctgatctgc agcgagatgc ccgaattgct gaagccgatg cccaggctgc
ctctgcgatc caaacggccg aaaatgacaa gatcacggcc ctgcgtcgga tcgatcgcga
tgtagcgatc gcccaagccg aggccgagcg ccggattcag gatgcgttga cgcggcgcga
agcggtggtg gccgaagctg aagcggacat tgctaccgaa gtcgctcgta gccaagcaga
actccctgtg cagcaggagc ggatcaaaca ggtgcagcag caacttcaag ccgatgtgat
cgccccagct gaggcagctt gtaaacgggc gatcgcggaa gcgcgggggg ccgccgcccg
tatcgtcgaa gatggaaaag ctcaagcgga agggacccaa cggctggcgg aggcttggca
gaccgctggt gctaatgccc gcgacatctt cctgctccag aagtctagac cagccaggac
agaaatgcct cgacttcgct gctacccaag gttgccgggt gacgcacacc gtggaaacgg
atgaaggcac gaacccagtg gacataagcc tgttcggttc gtaagctgta atgcaagtag
cgtatgcgct cacgcaactg gtccagaacc ttgaccgaac gcagcggtgg taacggcgca
gtggcggttt tcatggcttg ttatgactgt ttttttgggg tacagtctat gcctcgggca
```

Fig. 12B tccaagcagc aagcgcgtta cgccgtgggt cgatgtttga tgttatggag cagcaacgat
gttacgcagc agggcagtcg ccctaaaaca aagttaaaca ttatgaggga agcggtgatc
gccgaagtat cgactcaact atcagaggta gttggcgtca tcgagcgcca tctcgaaccg
acgttgctgg ccgtacattt gtacggctcc gcagtggatg gcggcctgaa gccacacagt
gatattgatt tgctggttac ggtgaccgta aggcttgatg aaacaacgcg gcgagctttg
atcaacgacc ttttggaaac ttcggcttcc cctggagaga gcgagattct ccgcgctgta
gaagtcacca ttgttgtgca cgacgacatc attccgtggc gttatccagc taagcgcgaa
ctgcaatttg gagaatggca gcgcaatgac attcttgctg gtatcttcga gccagccacg
atcgacattg atctggctat cttgctgaca aaagcaagag aacatagcgt tgccttggta
ggtccagcgg cggaggaact ctttgatccg gttcctgaac aggatctatt tgaggcgcta
aatgaaacct taacgctatg gaactcgccg cccgactggg ctggcgatga gcgaaatgta
gtgcttacgt tgtcccgcat ttggtacagc gcagtaaccg gcaaaatcgc gccgaaggat
gtcgctgccg actgggcaat ggagcgcctg ccggcccagt atcagcccgt catacttgaa
gctagacagg cttatcttgg acaagaagaa gatcgcttgg cctcgcgcgc agatcagttg
gaagaatttg tccactacgt gaaaggcgag atcaccaagg tagtcggcaa ataacctcat
tttcgccaga tatcgacgtc gacaccatcg aatggtgcaa aacctttcgc ggtatggcat
gatagcgccc ggaagagagt caattcaggg tggtgaatgt gaaaccagta acgttatacg
atgtcgcaga gtatgccggt gtctcttatc agaccgtttc ccgcgtggtg aaccaggcca
gccacgtttc tgcgaaaacg cgggaaaaag tggaagcggc gatggcggag ctgaattaca
ttcccaaccg cgtggcacaa caactggcgg gcaaacagtc gttgctgatt ggcgttgcca
cctccagtct ggccctgcac gcgccgtcgc aaattgtcgc ggcgattaaa tctcgcgccg
atcaactggg tgccagcgtg gtggtgtcga tggtagaacg aagcggcgtc gaagcctgta
aagcggcggt gcacaatctt ctcgcgcaac gcgtcagtgg gctgatcatt aactatccgc
tggatgacca ggatgccatt gctgtggaag ctgcctgcac taatgttccg gcgttatttc
ttgatgtctc tgaccagaca cccatcaaca gtattatttt ctcccatgaa gacggtacgc
gactgggcgt ggagcatctg gtcgcattgg gtcaccagca aatcgcgctg ttagcgggcc
cattaagttc tgtctcggcg cgtctgcgtc tggctggctg gcataaatat ctcactcgca
atcaaattca gccgatagcg gaacgggaag gcgactggag tgccatgtcc ggttttcaac
aaaccatgca aatgctgaat gagggcatcg ttcccactgc gatgctggtt gccaacgatc
agatggcgct gggcgcaatg cgcgccatta ccgagtccgg gctgcgcgtt ggtgcggata
tctcggtagt gggatacgac gataccgaag acagctcatg ttatatcccg ccgttaacca
ccatcaaaca ggattttcgc ctgctggggc aaaccagcgt ggaccgcttg ctgcaactct
ctcagggcca ggcggtgaag ggcaatcagc tgttgcccgt ctcactggtg aaaagaaaaa
ccaccctggc gcccaatacg caaaccgcct ctccccgcgc gttggccgat tcattaatgc
agctggcacg acaggtttcc cgactggaaa gcgggcagtg agcgcaacgc aattaatgta
agttagcgcg aattgatctg gtttgacagc ttatcatcga ctgcacggtg caccaatgct
tctggcgtca ggcagccatc ggaagctgtg gtatggctgt gcaggtcgta aatcactgca
taattcgtgt cgctcaaggc gcactcccgt tctggataat aacggttctg gcaaatattc
tgaaatgagc tgttgacaat taatcatccg gctcgtataa tgtgtggaat tgtgagcgga
taacaatttc agaattcaaa agatctttaa agaggagaat actagatgaa aaactgcgtg
atcgtgagcg ccgtgcgcac cgccatcggc agctttaacg gcagcctggc cagcaccagc

Fig. 12C

```
gccatcgatc tgggcgccac cgtgatcaaa gccgccatcg aacgcgccaa aatcgatagc
cagcacgtgg atgaagtgat catgggcaac gtgctccagg ccggcctggg ccagaacccc
gcccgccagg ccctgctgaa aagcggcctg gccgaaaccg tgtgcggctt taccgtgaac
aaagtgtgcg gcagcggcct gaaaagcgtg gccctggccg cccaggccat ccaggccggc
caggcccaga gcatcgtggc cggcggcatg gaaaacatga gcctggcccc ctacctgctg
gatgccaaag cccgcagcgg ctaccgcctg ggcgatggcc aggtgtacga tgtgatcctg
cgcgatggcc tgatgtgcgc cacccacggc taccacatgg gcatcaccgc cgaaaacgtg
gccaaagaat acggcatcac ccgcgaaatg caggatgaac tggccctgca cagccagcgc
aaagccgccg ccgccatcga aagcggcgcc tttaccgccg aaatcgtgcc cgtgaacgtg
gtgacccgca aaaaaaccdt tgtgtttagc caggatgaat ttcccaaagc caacagcacc
gccgaagccc tgggcgccct gcgccccgcc tttgataaag ccggcaccgt gaccgccggc
aacgccagcg gcatcaacga tggcgccgcc gccctggtga tcatggaaga aagcgccgcc
ctggccgccg gcctgacccc cctgcccgc atcaaaagct acgccagcgg cggcgtgccc
cccgccctga tgggcatggg ccccgtgccc gccacccaga aagccctcca gctggccggc
ctccagctgg ccgatatcga tctgatcgaa gccaacgaag ccttttgccgc ccagtttctg
gccgtgggca aaaacctggg cttttgatagc gaaaaagtga acgtgaacgg cggcgccatc
gccctgggcc accccatcgg cgccagcggc gcccgcatcc tggtgaccct gctgcacgcc
atgcaggccc gcgataaaac cctgggcctg gccaccctgt gcatcggcgg cggccagggc
atcgccatgg tgatcgaacg cctgaactag aagaggagaa atactagatg aacagcaaaa
tcatccgctt tgaaaacctg cgcagctttt ttaaagatgg catgaccatc atgatcggcg
gcttttctgaa ctgcggcacc cccaccaaac tgatcgattt tctggtgaac ctgaacatca
aaaacctgac catcatcagc aacgatacct gctaccccaa caccggcatc ggcaaactga
tcagcaacaa ccaggtgaaa aaactgatcg ccagctacat cggcagcaac cccgataccg
gcaaaaaact gtttaacaac gaactggaag tggaactgag cccccagggc accctggtgg
aacgcatccg cgccggcggc agcggcctgg gcggcgtgct gaccaaaacc ggcctgggca
ccctgatcga aaaaggcaaa aaaaaaatca gcatcaacgg caccgaatac ctgctggaac
tgccccctgac cgccgatatc gccctgatca aaggcagcat cgtggatgaa gccggcaaca
ccttttacaa aggcaccacc aaaaacttta ccccctacat ggccatggcc gccaaaaccg
tgatcgtgga agccgaaaac ctggtgagct gcgaaaaact ggaaaaagaa aaagccatga
ccccccggcgt gctgatcaac tacatcgtga agaacccgc ctaaaatgat caacgataaa
aacctggcca aagaaatcat cgccaaacgc gtggcccgcg aactgaaaaa cggccagctg
gtgaacctgg gcgtgggcct gcccaccatg gtggccgatt acatccccaa aaactttaaa
atcaccttc agagcgaaaa cggcatcgtg ggcatgggcg ccagcccaa atcaacgaa
gccgataaag atgtggtgaa cgccggcgc gattacacca ccgtgctgcc cgatggcacc
tttttttgata gcagcgtgag ctttagcctg atccgcggcg gccacgtgga tgtgaccgtg
ctgggcgccc tccaggtgga tgaaaaaggc aacatcgcca actggatcgt gcccggcaaa
atgctgagcg gcatgggcgg cgccatggat ctggtgaacg gcgccaaaaa agtgatcatc
gccatgcgcc acaccaacaa aggccagccc aaaatcctga aaaatgcac cctgccctg
accgccaaaa gccaggccaa cctgatcgtg accgaactgg gcgtgatcga agtgatcaac
gatggcctgc tgctgaccga aatcaacaaa acaccacca tcgatgaaat ccgcagcctg
accgccgccg atctgctgat cagcaacgaa ctgcgcccca tggccgtgta gggatctgga
```

Fig. 12D

```
tctttaaaga ggagaatact agatgctgaa agatgaagtg atcaaacaga tcagcacccc
cctgaccagc cccgcctttc cccgcggccc ctacaaattt cacaaccgcg aatactttaa
catcgtgtac cgcaccgata tggatgccct gcgcaaagtg gtgcccgaac ccctggaaat
cgatgaaccc ctggtgcgct tgaaatcat ggccatgcac gataccagcg gcctgggctg
ctacaccgaa agcggccagg ccatccccgt gagctgcaac ggcgtgaaag gcgattacct
gcacatgatg tacctggata acgaacccgc catcgccgtg ggccgcgaac tgagcgccta
ccccaaaaaa ctgggctacc ccaaactgtt tgtggatagc gatacctgg tgggcaccct
ggattacggc aaactgcgcg tggccaccgc caccatgggc tacaaacaca aagccctgga
tgccaacgaa gccaaagatc agatttgccg ccccaactac atgctgaaaa tcatccccaa
ctacgatggc agccccgca tctgcgaact gatcaacgcc aaaatcaccg atgtgaccgt
gcacgaagcc tggaccggcc ccacccgcct ccagctgttt gatcacgcca tggccccct
gaacgatctg cccgtgaaag aaatcgtgag cagcagccac atcctggccg atatcatcct
gccccgcgcc gaagtgatct acgattacct gaaatagctc gagtaaggat ctccaggcat
caaataaaac gaaaggctca gtcgaaagac tgggcctttc gttttatctg ttgtttgtcg
gtgaacgctc tctactagag tcacactggc tcaccttcgg gtgggccttt ctgcgtttat
acctagggcg ttcggctgcg gcgagcggta tcagctcact caaaggcggt aatacgtccc
tgctcgtcac gctttcaggc accgtgccag atatcgacgt ggagtcgatc actgtgattg
gcgaagggga aggcagcgct acccaaatcg ctagcttgct ggagaagctg aaacaaacca
cgggcattga tctggcgaaa tccctaccgg tcaatccga ctcgcccgct gcgaagtcct
aagagatagc gatgtgaccg cgatcgcttg tcaagaatcc cagtgatccc gaaccatagg
aaggcaagct caatgcttgc ctcgtcttga ggactatcta gatgtctgtg aacgcacat
ttattgccat caagcccgat ggcgttcagc ggggtttggt cggtacgatc atcggccgct
ttgagcaaaa aggcttcaaa ctggtgggcc taaagcagct gaagcccagt cgcgagctgg
ccgaacagca ctatgctgtc caccgcgagc gccccttctt caatggcctc gtcgagttca
tcacctctgg gccgatcgtg gcgatcgtct tggaaggcga aggcgttgtg gcggctgctc
gcaagttgat cggcgctacc aatccgctga cggcagaacc gggcaccatc cgtggtgatt
ttggtgtcaa tattggccgc aacatcatcc atggctcgga tgcaatcgaa acagcacaac
aggaaattgc tctctggttt agcccagcag agctaagtga ttgaccccc acgattcaac
cctggctgta cgaataaggt ctgcattcct tcagagagac attgccatgc cc
```

Fig. 13A

```
gataatctca tgaccaaaat cccttaacgt gagttttcgt tccactgagc gtcagacccc
gtagaaaaga tcaaaggatc ttcttgagat cctttttttc tgcgcgtaat ctgctgcttg
caaacaaaaa aaccaccgct accagcggtg gtttgtttgc cggatcaaga gctaccaact
cttttccga aggtaactgg cttcagcaga gcgcagatac caaatactgt tcttctagtg
tagccgtagt taggccacca cttcaagaac tctgtagcac cgcctacata cctcgctctg
ctaatcctgt taccagtggc tgctgccagt ggcgataagt cgtgtcttac cgggttggac
tcaagacgat agttaccgga taaggcgcag cggtcgggct gaacggggg ttcgtgcaca
cagcccagct tggagcgaac gacctacacc gaactgagat acctacagcg tgagctatga
gaaagcgcca cgcttccga agggagaaag gcggacaggt atccggtaag cggcagggtc
ggaacaggag agcgcacgag ggagcttcca gggggaaacg cctggtatct ttatagtcct
gtcgggtttc gccacctctg acttgagcgt cgatttttgt gatgctcgtc aggggggcgg
agcctatgga aaaacgccag caacgcggcc ttttacggt tcctggcctt ttgctggcct
tttgctcaca tgtgtgctgg gccccaatgc cttctccaag ggcggcattc ccctgactgt
tgaaggcgtt gccaatatca agattgctgg ggaagaaccg accatccaca acgcgatcga
gcggctgctt ggcaaaaacc gtaaggaaat cgagcaaatt gccaaggaga ccctcgaagg
caacttgcgt ggtgttttag ccagcctcac gccggagcag atcaacgagg acaaaattgc
ctttgccaaa agtctgctgg aagaggcgga ggatgacctt gagcagctgg gtctagtcct
cgatacgctg caagtccaga acatttccga tgaggtcggt tatctctcgg ctagtggacg
caagcagcgg gctgatctgc agcgagatgc ccgaattgct gaagccgatg cccaggctgc
ctctgcgatc caaacggccg aaaatgacaa gatcacggcc ctgcgtcgga tcgatcgcga
tgtagcgatc gcccaagccg aggccgagcg ccggattcag gatgcgttga cgcggcgcga
agcggtggtg gccgaagctg aagcggacat tgctaccgaa gtcgctcgta gccaagcaga
actccctgtg cagcaggagc ggatcaaaca ggtgcagcag caacttcaag ccgatgtgat
cgccccagct gaggcagctt gtaaacgggc gatcgcggaa gcgcgggggg ccgccgcccg
tatcgtcgaa gatggaaaag ctcaagcgga agggacccaa cggctggcgg aggcttggca
gaccgctggt gctaatgccc gcgacatctt cctgctccag aagtctagac cagccaggac
agaaatgcct cgacttcgct gctacccaag gttgccgggt gacgcacacc gtggaaacgg
atgaaggcac gaacccagtg gacataagcc tgttcggttc gtaagctgta atgcaagtag
cgtatgcgct cacgcaactg gtccagaacc ttgaccgaac gcagcggtgg taacggcgca
gtggcggttt tcatggcttg ttatgactgt ttttttgggg tacagtctat gcctcgggca
```

Fig. 13B

```
tccaagcagc aagcgcgtta cgccgtgggt cgatgtttga tgttatggag cagcaacgat
gttacgcagc agggcagtcg ccctaaaaca aagttaaaca ttatgaggga agcggtgatc
gccgaagtat cgactcaact atcagaggta gttggcgtca tcgagcgcca tctcgaaccg
acgttgctgg ccgtacattt gtacggctcc gcagtggatg gcggcctgaa gccacacagt
gatattgatt tgctggttac ggtgaccgta aggcttgatg aaacaacgcg gcgagctttg
atcaacgacc ttttggaaac ttcggcttcc cctggagaga gcgagattct ccgcgctgta
gaagtcacca ttgttgtgca cgacgacatc attccgtggc gttatccagc taagcgcgaa
ctgcaatttg gagaatggca gcgcaatgac attcttgctg gtatcttcga gccagccacg
atcgacattg atctggctat cttgctgaca aaagcaagag aacatagcgt tgccttggta
ggtccagcgg cggaggaact ctttgatccg gttcctgaac aggatctatt tgaggcgcta
aatgaaacct taacgctatg gaactcgccg cccgactggg ctggcgatga gcgaaatgta
gtgcttacgt tgtcccgcat ttggtacagc gcagtaaccg gcaaaatcgc gccgaaggat
gtcgctgccg actgggcaat ggagcgcctg ccggcccagt atcagcccgt catacttgaa
gctagacagg cttatcttgg acaagaagaa gatcgcttgg cctcgcgcgc agatcagttg
gaagaatttg tccactacgt gaaaggcgag atcaccaagg tagtcggcaa ataacctcat
tttcgccaga tatcgacgtc gacaccatcg aatggtgcaa aacctttcgc ggtatggcat
gatagcgccc ggaagagagt caattcaggg tggtgaatgt gaaaccagta acgttatacg
atgtcgcaga gtatgccggt gtctcttatc agaccgtttc ccgcgtggtg aaccaggcca
gccacgtttc tgcgaaaacg cgggaaaaag tggaagcggc gatggcggag ctgaattaca
ttcccaaccg cgtggcacaa caactggcgg gcaaacagtc gttgctgatt ggcgttgcca
cctccagtct ggccctgcac gcgccgtcgc aaattgtcgc ggcgattaaa tctcgcgccg
atcaactggg tgccagcgtg gtggtgtcga tggtagaacg aagcggcgtc gaagcctgta
aagcggcggt gcacaatctt ctcgcgcaac gcgtcagtgg gctgatcatt aactatccgc
tggatgacca ggatgccatt gctgtggaag ctgcctgcac taatgttccg gcgttatttc
ttgatgtctc tgaccagaca cccatcaaca gtattatttt ctcccatgaa gacggtacgc
gactgggcgt ggagcatctg gtcgcattgg gtcaccagca aatcgcgctg ttagcgggcc
cattaagttc tgtctcggcg cgtctgcgtc tggctggctg gcataaatat ctcactcgca
atcaaattca gccgatagcg gaacgggaag gcgactggag tgccatgtcc ggttttcaac
aaaccatgca aatgctgaat gagggcatcg ttcccactgc gatgctggtt gccaacgatc
agatggcgct gggcgcaatg cgcgccatta ccgagtccgg gctgcgcgtt ggtgcggata
tctcggtagt gggatacgac gataccgaag acagctcatg ttatatcccg ccgttaacca
ccatcaaaca ggattttcgc ctgctggggc aaaccagcgt ggaccgcttg ctgcaactct
ctcagggcca ggcggtgaag ggcaatcagc tgttgcccgt ctcactggtg aaaagaaaaa
ccaccctggc gcccaatacg caaaccgcct ctccccgcgc gttggccgat tcattaatgc
agctggcacg acaggtttcc cgactggaaa gcgggcagtg agcgcaacgc aattaatgta
agttagcgcg aattgatctg gtttgacagc ttatcatcga ctgcacggtg caccaatgct
tctggcgtca ggcagccatc ggaagctgtg gtatggctgt gcaggtcgta atcactgca
taattcgtgt cgctcaaggc gcactcccgt tctggataat gttttttgcg ccgacatcat
aacggttctg gcaaatattc tgaaatgagc tgttgacaat taatcatccg gctcgtataa
tgtgtggaat tgtgagcgga taacaatttc agaattcaaa agatctaaag aggagaaata
ctagatgacc gatgtgcgct ttcgcatcat cggcaccggc gcctacgtgc ccgaacgcat
```

Fig. 13C

```
cgtgagcaac gatgaagtgg gcgcccccgc cggcgtggat gatgattgga tcacccgcaa
aaccggcatc cgccagcgcc gctgggccgc cgatgatcag gccaccagcg atctggccac
cgccgccggc cgcgccgccc tgaaagccgc cggcatcacc cccgaacagc tgaccgtgat
cgccgtggcc accagcaccc ccgatcgccc ccagccccce accgccgcct acgtgcagca
ccacctgggc gccaccggca ccgccgcctt tgatgtgaac gccgtgtgca gcggcaccgt
gtttgccctg agcagcgtgg ccggcaccct ggtgtaccgc ggcggctacg ccctggtgat
cggcgccgat ctgtacagcc gcatcctgaa ccccgccgat cgcaaaaccg tggtgctgtt
tggcgatggc gccggcgcca tggtgctggg cccaccagc accggcaccg gcccatcgt
gcgccgcgtg gccctgcaca ccttggcgg cctgaccgat ctgatccgcg tgcccgccgg
cggcagccgc cagcccctgg ataccgatgg cctggatgcc ggcctgcagt actttgccat
ggatggccgc gaagtgcgcc gctttgtgac cgaacacctg ccccagctga tcaaaggctt
tctgcacgaa gccggcgtgg atgccgccga tatcagccac tttgtgcccc accaggccaa
cggcgtgatg ctggatgaag tgtttggcga actgcacctg ccccgcgcca ccatgcaccg
caccgtggaa acctacggca acaccggcgc cgccagcatc cccatcacca tggatgccgc
cgtgcgcgcc ggcagctttc gccccggcga actggtgctg ctggccggct tggcggcgg
catggccgcc agctttgccc tgatcgaatg gtagggatct aagaggagaa atactagatg
aaaaccaaac tgatgaccct ccaggatgcc accggctttt tcgcgatgg catgaccatc
atggtgggcg gctttatggg catcggcacc cccagccgcc tggtggaagc cctgctggaa
agcggcgtgc gcgatctgac cctgatcgcc aacgataccg cctttgtgga taccggcatc
ggcccctga tcgtgaacgg ccgcgtgcgc aaagtgatcg ccagccacat cggcaccaac
cccgaaaccg gccgccgcat gatcagcggc gaaatggatg tggtgctggt gccccagggc
accctgatcg aacagatccg ctgcggcggc gccggcctgg cggctttct gaccccccacc
ggcgtgggca ccgtggtgga agaaggcaaa cagaccctga ccctggatgg caaaacctgg
ctgctggaac gccccctgcg cgccgatctg gccctgatcc gcgcccaccg ctgcgatacc
ctgggcaacc tgacctacca gctgagcgcc gcaactta ccccctgat cgccctggcc
gccgatatca ccctggtgga acccgatgaa ctggtggaaa ccggcgaact ccagcccgat
cacatcgtga ccccggcgc cgtgatcgat cacatcatcg tgagccagga aagcaaatag
ttaaagagga gaatactaga tggatgccaa acagcgcatc gcccgccgcg tgcccagga
actgcgcgat ggcgatatcg tgaacctggg catcggcctg cccaccatgg tggccaacta
cctgcccgaa ggcatccaca tcaccctcca gagcgaaaac ggctttctgg gcctgggccc
cgtgaccacc gcccaccccg atctggtgaa cgccggcggc cagccctgcg gcgtgctgcc
cggcgccgcc atgtttgata gcgccatgag ctttgccctg atccgcggcg gccacatcga
tgcctgcgtg ctgggcggcc tccaggtgga tgaagaagcc aacctggcca ctgggtggt
gcccggcaaa atggtgcccg gcatgggcgg cgccatggat ctggtgaccg gcagccgcaa
agtgatcatc gccatggaac actgcgccaa agatggcagc gccaaaatcc tgcgccgctg
caccatgccc ctgaccgccc agcacgccgt gcacatgctg gtgaccgaac tggccgtgtt
tcgctttatc gatggcaaaa tgtggctgac cgaaatcgcc gatggctgcg atctggccac
cgtgcgcgcc aaaaccgaag cccgctttga gtggccgcc gatctgaaca cccagcgcgg
cgatctgtag ggatctggat ctttaaagag gagaatacta gatgctgaaa gatgaagtga
tcaaacagat cagcacccc ctgaccagcc ccgcctttcc ccgcggcccc tacaaatttc
acaaccgcga atactttaac atcgtgtacc gcaccgatat ggatgccctg cgcaaagtgg
```

Fig. 13D

```
tgcccgaacc cctggaaatc gatgaacccc tggtgcgctt tgaaatcatg gccatgcacg
ataccagcgg cctgggctgc tacaccgaaa gcggccaggc catccccgtg agctgcaacg
gcgtgaaagg cgattacctg cacatgatgt acctggataa cgaacccgcc atcgccgtgg
gccgcgaact gagcgcctac cccaaaaaac tgggctaccc caaactgttt gtggatagcg
ataccctggt gggcaccctg gattacggca aactgcgcgt ggccaccgcc accatgggct
acaaacacaa agccctggat gccaacgaag ccaaagatca gatttgccgc cccaactaca
tgctgaaaat catccccaac tacgatggca gccccgcat ctgcgaactg atcaacgcca
aaatcaccga tgtgaccgtg cacgaagcct ggaccggccc caccgcctc cagctgtttg
atcacgccat ggccccctg aacgatctgc ccgtgaaaga aatcgtgagc agcagccaca
tcctggccga tatcatcctg ccccgcgccg aagtgatcta cgattacctg aaatagctcg
agtaaggatc tccaggcatc aaataaaacg aaaggctcag tcgaaagact gggcctttcg
ttttatctgt tgtttgtcgg tgaacgctct ctactagagt cacactggct caccttcggg
tgggcctttc tgcgtttata cctagggcgt tcggctgcgg cgagcggtat cagctcactc
aaaggcggta atacgtccct gctcgtcacg ctttcaggca ccgtgccaga tatcgacgtg
gagtcgatca ctgtgattgg cgaaggggaa ggcagcgcta cccaaatcgc tagcttgctg
gagaagctga aacaaaccac gggcattgat ctggcgaaat ccctaccggg tcaatccgac
tcgcccgctg cgaagtccta agagatagcg atgtgaccgc gatcgcttgt caagaatccc
agtgatcccg aaccatagga aggcaagctc aatgcttgcc tcgtcttgag gactatctag
atgtctgtgg aacgcacatt tattgccatc aagcccgatg gcgttcagcg gggtttggtc
ggtacgatca tcggccgctt tgagcaaaaa ggcttcaaac tggtgggcct aaagcagctg
aagcccagtc gcgagctggc cgaacagcac tatgctgtcc accgcgagcg ccccttcttc
aatggcctcg tcgagttcat cacctctggg ccgatcgtgg cgatcgtctt ggaaggcgaa
ggcgttgtgg cggctgctcg caagttgatc ggcgctacca atccgctgac ggcagaaccg
ggcaccatcc gtggtgattt tggtgtcaat attggccgca acatcatcca tggctcggat
gcaatcgaaa cagcacaaca ggaaattgct ctctggttta gcccagcaga gctaagtgat
tggacccca cgattcaacc ctggctgtac gaataaggtc tgcattcctt cagagagaca
ttgccatgcc c
```

Fig. 14A

```
gataatctca tgaccaaaat cccttaacgt gagttttcgt tccactgagc gtcagaccee
gtagaaaaga tcaaaggatc ttcttgagat ccttttttc tgcgcgtaat ctgctgcttg
caaacaaaaa aaccaccgct accagcggtg gtttgtttgc cggatcaaga gctaccaact
cttttccga aggtaactgg cttcagcaga gcgcagatac caaatactgt tcttctagtg
tagccgtagt taggccacca cttcaagaac tctgtagcac cgcctacata cctcgctctg
ctaatcctgt taccagtggc tgctgccagt ggcgataagt cgtgtcttac cgggttggac
tcaagacgat agttaccgga taaggcgcag cggtcgggct gaacgggggg ttcgtgcaca
cagcccagct tggagcgaac gacctacacc gaactgagat acctacagcg tgagctatga
gaaagcgcca cgcttcccga agggagaaag gcggacaggt atccggtaag cggcagggtc
ggaacaggag agcgcacgag ggagcttcca gggggaaacg cctggtatct ttatagtcct
gtcgggtttc gccacctctg acttgagcgt cgattttgt gatgctcgtc aggggggcgg
agcctatgga aaaacgccag caacgcggcc ttttttacggt tcctggcctt ttgctggcct
tttgctcaca tgtgtgctgg gccccaatgc cttctccaag ggcggcattc ccctgactgt
tgaaggcgtt gccaatatca agattgctgg ggaagaaccg accatccaca acgcgatcga
gcggctgctt ggcaaaaacc gtaaggaaat cgagcaaatt gccaaggaga ccctcgaagg
caacttgcgt ggtgttttag ccagcctcac gccggagcag atcaacgagg acaaaattgc
ctttgccaaa agtctgctgg aagaggcgga ggatgacctt gagcagctgg gtctagtcct
cgatacgctg caagtccaga acatttccga tgaggtcggt tatctctcgg ctagtggacg
caagcagcgg gctgatctgc agcgagatgc ccgaattgct gaagccgatg cccaggctgc
ctctgcgatc caaacggccg aaaatgacaa gatcacggcc ctgcgtcgga tcgatcgcga
tgtagcgatc gcccaagccg aggccgagcg ccggattcag gatgcgttga cgcggcgcga
agcggtggtg gccgaagctg aagcggacat tgctaccgaa gtcgctcgta gccaagcaga
actccctgtg cagcaggagc ggatcaaaca ggtgcagcag caacttcaag ccgatgtgat
cgccccagct gaggcagctt gtaaacgggc gatcgcggaa gcgcgggggg ccgccgcccg
tatcgtcgaa gatggaaaag ctcaagcgga agggacccaa cggctggcgg aggcttggca
gaccgctggt gctaatgccc gcgacatctt cctgctccag aagtctagac cagccaggac
agaaatgcct cgacttcgct gctacccaag gttgccgggt gacgcacacc gtggaaacgg
atgaaggcac gaacccagtg gacataagcc tgttcggttc gtaagctgta atgcaagtag
cgtatgcgct cacgcaactg gtccagaacc ttgaccgaac gcagcggtgg taacggcgca
gtggcggttt tcatggcttg ttatgactgt tttttggggg tacagtctat gcctcgggca
tccaagcagc aagcgcgtta cgccgtgggt cgatgtttga tgttatggag cagcaacgat
gttacgcagc agggcagtcg ccctaaaaca aagttaaaca ttatgaggga agcggtgatc
gccgaagtat cgactcaact atcagaggta gttggcgtca tcgagcgcca tctcgaaccg
acgttgctgg ccgtacattt gtacggctcc gcagtggatg gcggcctgaa gccacacagt
gatattgatt tgctggttac ggtgaccgta aggcttgatg aaacaacgcg gcgagctttg
atcaacgacc ttttggaaac ttcggcttcc cctggagaga gcgagattct ccgcgctgta
gaagtcacca ttgttgtgca cgacgacatc attccgtggc gttatccagc taagcgcgaa
ctgcaatttg gagaatggca gcgcaatgac attcttgctg gtatcttcga gccagccacg
atcgacattg atctggctat cttgctgaca aaagcaagag aacatagcgt tgccttggta
ggtccagcgg cggaggaact ctttgatccg gttcctgaac aggatctatt tgaggcgcta
aatgaaacct taacgctatg gaactcgccg cccgactggg ctggcgatga gcgaaatgta
```

Fig. 14B

```
gtgcttacgt tgtcccgcat ttggtacagc gcagtaaccg gcaaaatcgc gccgaaggat
gtcgctgccg actgggcaat ggagcgcctg ccggcccagt atcagcccgt catacttgaa
gctagacagg cttatcttgg acaagaagaa gatcgcttgg cctcgcgcgc agatcagttg
gaagaatttg tccactacgt gaaaggcgag atcaccaagg tagtcggcaa ataacctcat
tttcgccaga tatcgacgtc gacaccatcg aatggtgcaa aacctttcgc ggtatggcat
gatagcgccc ggaagagagt caattcaggg tggtgaatgt gaaaccagta acgttatacg
atgtcgcaga gtatgccggt gtctcttatc agaccgtttc ccgcgtggtg aaccaggcca
gccacgtttc tgcgaaaacg cgggaaaaag tggaagcggc gatggcggag ctgaattaca
ttcccaaccg cgtggcacaa caactggcgg gcaaacagtc gttgctgatt ggcgttgcca
cctccagtct ggccctgcac gcgccgtcgc aaattgtcgc ggcgattaaa tctcgcgccg
atcaactggg tgccagcgtg gtggtgtcga tggtagaacg aagcggcgtc gaagcctgta
aagcggcggt gcacaatctt ctcgcgcaac gcgtcagtgg gctgatcatt aactatccgc
tggatgacca ggatgccatt gctgtggaag ctgcctgcac taatgttccg gcgttatttc
ttgatgtctc tgaccagaca cccatcaaca gtattatttt ctccatgaa gacggtacgc
gactgggcgt ggagcatctg gtcgcattgg gtcaccagca aatcgcgctg ttagcgggcc
cattaagttc tgtctcggcg cgtctgcgtc tggctggctg gcataaatat ctcactcgca
atcaaattca gccgatagcg gaacgggaag gcgactggag tgccatgtcc ggtttttcaac
aaaccatgca aatgctgaat gagggcatcg ttcccactgc gatgctggtt gccaacgatc
agatggcgct gggcgcaatg cgcgccatta ccgagtccgg gctgcgcgtt ggtgcggata
tctcggtagt gggatacgac gataccgaag acagctcatg ttatatcccg ccgttaacca
ccatcaaaca ggattttcgc ctgctggggc aaaccagcgt ggaccgcttg ctgcaactct
ctcagggcca ggcggtgaag ggcaatcagc tgttgcccgt ctcactggtg aaaagaaaaa
ccaccctggc gcccaatacg caaaccgcct ctccccgcgc gttggccgat tcattaatgc
agctggcacg acaggtttcc cgactggaaa gcgggcagtg agcgcaacgc aattaatgta
agttagcgcg aattgatctg gtttgacagc ttatcatcga ctgcacggtg caccaatgct
tctggcgtca ggcagccatc ggaagctgtg gtatggctgt gcaggtcgta atcactgca
taattcgtgt cgctcaaggc gcactcccgt tctggataat gttttttgcg ccgacatcat
aacggttctg gcaaatattc tgaaatgagc tgttgacaat taatcatccg gctcgtataa
tgtgtggaat tgtgagcgga taacaatttc agaattcaaa agatctaaag aggagaaata
ctagatgacc gatgtgcgct ttcgcatcat cggcaccggc gcctacgtgc ccgaacgcat
cgtgagcaac gatgaagtgg gcgccccccgc cggcgtggat gatgattgga tcacccgcaa
aaccggcatc cgccagcgcc gctgggccgc cgatgatcag gccaccagcg atctggccac
cgccgccggc cgcgccgccc tgaaagccgc cggcatcacc cccgaacagc tgaccgtgat
cgccgtggcc accagcaccc ccgatcgccc ccagcccccc accgccgcct acgtgcagca
ccacctgggc gccaccggca ccgccgcctt tgatgtgaac gccgtgtgca gcggcaccgt
gtttgccctg agcagcgtgg ccggcaccct ggtgtaccgc ggcggctacg ccctggtgat
cggcgccgat ctgtacagcc gcatcctgaa ccccgccgat cgcaaaaccg tggtgctgtt
tggcgatggc gccggcgcca tggtgctggg ccccaccagc accggcaccg gccccatcgt
gcgccgcgtg gccctgcaca ccttggcgg cctgaccgat ctgatccgcg tgcccgccgg
cggcagccgc cagcccctgg ataccgatgg cctggatgcc ggcctgcagt actttgccat
ggatggccgc gaagtgcgcc gctttgtgac cgaacacctg ccccagctga tcaaaggctt
```

Fig. 14C

```
tctgcacgaa gccggcgtgg atgccgccga tatcagccac tttgtgcccc accaggccaa
cggcgtgatg ctggatgaag tgtttggcga actgcacctg ccccgcgcca ccatgcaccg
caccgtggaa acctacggca acaccggcgc cgccagcatc cccatcacca tggatgccgc
cgtgcgcgcc ggcagctttc gccccggcga actggtgctg ctggccggct tggcggcgg
catggccgcc agctttgccc tgatcgaatg tagggatct aagaggagaa atactagatg
aacagcaaaa tcatccgctt tgaaaacctg cgcagctttt ttaaagatgg catgaccatc
atgatcggcg gctttctgaa ctgcggcacc cccaccaaac tgatcgattt tctggtgaac
ctgaacatca aaaacctgac catcatcagc aacgatacct gctacccaa caccggcatc
ggcaaactga tcagcaacaa ccaggtgaaa aaactgatcg ccagctacat cggcagcaac
cccgataccg gcaaaaaact gtttaacaac gaactggaag tggaactgag cccccagggc
accctggtgg aacgcatccg cgccggcggc agcggcctgg gcggcgtgct gaccaaaacc
ggcctgggca ccctgatcga aaaggcaaa aaaaaatca gcatcaacgg caccgaatac
ctgctggaac tgccctgac cgccgatatc gccctgatca aggcagcat cgtggatgaa
gccggcaaca ccttttacaa aggcaccacc aaaaactta accctacat ggccatggcc
gccaaaaccg tgatcgtgga agccgaaaac ctggtgagct gcgaaaaact ggaaaaagaa
aaagccatga cccccggcgt gctgatcaac tacatcgtga agaacccgc ctaaaatgat
caacgataaa aacctggcca agaaatcat cgccaaacgc gtggcccgcg aactgaaaaa
cggccagctg gtgaacctgg gcgtgggcct gcccaccatg gtggccgatt acatccccaa
aaactttaaa atcacctttc agagcgaaaa cggcatcgtg ggcatgggcg ccagccccaa
aatcaacgaa gccgataaag atgtggtgaa cgccggcggc gattacacca ccgtgctgcc
cgatggcacc ttttttgata gcagcgtgag ctttagcctg atccgcggcg gccacgtgga
tgtgaccgtg ctgggcgccc tccaggtgga tgaaaaggc aacatcgcca actggatcgt
gcccggcaaa atgctgagcg gcatgggcgg cgccatggat ctggtgaacg gcgccaaaaa
agtgatcatc gccatgcgcc acaccaacaa aggcagccc aaaatcctga aaaatgcac
cctgcccctg accgccaaaa gccaggccaa cctgatcgtg accgaactgg gcgtgatcga
agtgatcaac gatggcctgc tgctgaccga atcaacaaa acaccacca tcgatgaaat
ccgcagcctg accgccgccg atctgctgat cagcaacgaa ctgcgcccca tggccgtgta
gggatctgga tctttaaaga ggagaatact agatgctgaa agatgaagtg atcaaacaga
tcagcacccc cctgaccagc cccgcctttc cccgcgccc ctacaaattt cacaccgcg
aatactttaa catcgtgtac cgcaccgata tggatgccct gcgcaaagtg gtgcccgaac
ccctggaaat cgatgaaccc ctggtgcgct tgaaatcat ggccatgcac gataccagcg
gcctgggctg ctacaccgaa agcggccagg ccatccccgt gagctgcaac ggcgtgaaag
gcgattacct gcacatgatg tacctggata cgaacccgc catcgccgtg ggccgcgaac
tgagcgccta ccccaaaaaa ctgggctacc ccaaactgtt tgtggatagc gataccctgg
tgggcaccct ggattacggc aaactgcgcg tggccaccgc caccatgggc tacaaacaca
aagccctgga tgccaacgaa gccaaagatc agatttgccg ccccaactac atgctgaaaa
tcatccccaa ctacgatggc agccccgca tctgcgaact gatcaacgcc aaaatcaccg
atgtgaccgt gcacgaagcc tggaccggcc ccacccgcct ccagctgttt gatcacgcca
tggccccct gaacgatctg cccgtgaaag aaatcgtgag cagcagccac atcctggccg
atatcatcct gccccgcgcc gaagtgatct acgattacct gaaatagctc gagtaaggat
ctccaggcat caaataaaac gaaaggctca gtcgaaagac tgggcctttc gttttatctg
```

Fig. 14D ttgtttgtcg gtgaacgctc tctactagag tcacactggc tcaccttcgg gtgggccttt
ctgcgtttat acctagggcg ttcggctgcg gcgagcggta tcagctcact caaaggcggt
aatacgtccc tgctcgtcac gctttcaggc accgtgccag atatcgacgt ggagtcgatc
actgtgattg gcgaagggga aggcagcgct acccaaatcg ctagcttgct ggagaagctg
aaacaaacca cgggcattga tctggcgaaa tccctaccgg gtcaatccga ctcgcccgct
gcgaagtcct aagagatagc gatgtgaccg cgatcgcttg tcaagaatcc cagtgatccc
gaaccatagg aaggcaagct caatgcttgc ctcgtcttga ggactatcta gatgtctgtg
gaacgcacat ttattgccat caagcccgat ggcgttcagc ggggtttggt cggtacgatc
atcggccgct ttgagcaaaa aggcttcaaa ctggtgggcc taaagcagct gaagcccagt
cgcgagctgg ccgaacagca ctatgctgtc caccgcgagc gccccttctt caatggcctc
gtcgagttca tcacctctgg gccgatcgtg gcgatcgtct tggaaggcga aggcgttgtg
gcggctgctc gcaagttgat cggcgctacc aatccgctga cggcagaacc gggcaccatc
cgtggtgatt ttggtgtcaa tattggccgc aacatcatcc atggctcgga tgcaatcgaa
acagcacaac aggaaattgc tctctggttt agcccagcag agctaagtga ttggacccccc
acgattcaac cctggctgta cgaataaggt ctgcattcct tcagagagac attgccatgc
cc

Fig. 15 ctgattgttc taggcgctg

Fig. 16 tttggcaatc tgaagacccg

SEQUENCE LISTING

<160> NUMBER OF SEQ ID NOS: 11

<210> SEQ ID NO 1
<211> LENGTH: 1185
<212> TYPE: DNA
<213> ORGANISM: Artificial Sequence
<220> FEATURE:
<223> OTHER INFORMATION: atoB gene

<400> SEQUENCE: 1

```
atgaaaaact gcgtgatcgt gagcgccgtg cgcaccgcca tcggcagctt taacggcagc        60
ctggccagca ccagcgccat cgatctgggc gccaccgtga tcaaagccgc catcgaacgc       120
gccaaaatcg atagccagca cgtggatgaa gtgatcatgg caacgtgct ccaggccggc        180 ctgggccaga accccgcccg ccaggccctg ctgaaaagcg gcctggccga aaccgtgtgc       240
ggctttaccg tgaacaaagt gtgcggcagc ggcctgaaaa gcgtggccct ggccgcccag       300
gccatccagg ccggccaggc ccagagcatc gtggccggcg gcatggaaaa catgagcctg       360 gcccctacc tgctggatgc caaagcccgc agcggctacc gcctgggcga tgccaggtg        420 tacgatgtga tcctgcgcga tggcctgatg tgcgccaccc acggctacca catgggcatc        480
accgccgaaa acgtggccaa agaatacggc atcacccgcg aaatgcagga tgaactggcc        540
ctgcacagcc agcgcaaagc cgccgccgcc atcgaaagcg gcgcctttac cgccgaaatc        600
gtgcccgtga acgtggtgac ccgcaaaaaa acctttgtgt ttagccagga tgaatttccc        660
aaagccaaca gcaccgccga agccctgggc gcctgcgcc ccgcctttga taaagccggc         720
accgtgaccg ccggcaacgc cagcggcatc aacgatggcg ccgccgccct ggtgatcatg        780
gaagaaagcg ccgccctggc cgccggcctg accccccctgg cccgcatcaa aagctacgcc       840
agcggcggcg tgccccccgc cctgatgggc atgggccccg tgcccgccac ccagaaagcc       900
```

| | |
|---|---|
| ctccagctgg ccggcctcca gctggccgat atcgatctga tcgaagccaa cgaagccttt | 960 |
| gccgcccagt ttctggccgt gggcaaaaac ctgggctttg atagcgaaaa agtgaacgtg | 1020 |
| aacgcggcg ccatcgccct gggccacccc atcgcgcca gcggcgcccg catcctggtg | 1080 |
| accctgctgc acgccatgca ggcccgcgat aaaaccctgg gcctggccac cctgtgcatc | 1140 |
| ggcggcggcc agggcatcgc catggtgatc gaacgcctga actag | 1185 |

<210> SEQ ID NO 2
<211> LENGTH: 990
<212> TYPE: DNA
<213> ORGANISM: Artificial Sequence
<220> FEATURE:
<223> OTHER INFORMATION: nphT7 gene

<400> SEQUENCE: 2

| | |
|---|---|
| atgaccgatg tgcgctttcg catcatcggc accggcgcct acgtgcccga acgcatcgtg | 60 |
| agcaacgatg aagtgggcgc ccccgccggc gtggatgatg attggatcac ccgcaaaacc | 120 |
| ggcatccgcc agcgccgctg gccgccgat gatcaggcca ccagcgatct ggccaccgcc | 180 |
| gccggccgcg ccgccctgaa agccgccggc atcaccccg aacagctgac cgtgatcgcc | 240 |
| gtggccacca gcacccccga tcgccccag ccccccaccg ccgcctacgt gcagcaccac | 300 |
| ctgggcgcca ccggcaccgc cgcctttgat gtgaacgccg tgtgcagcgg caccgtgttt | 360 |
| gccctgagca gcgtggccgg caccctggtg taccgcggcg gctacgccct ggtgatcggc | 420 |
| gccgatctgt acagccgcat cctgaacccc gccgatcgca aaaccgtggt gctgtttggc | 480 |
| gatggcgccg cgccatggt gctgggcccc accagcaccg gcaccggccc catcgtgcgc | 540 |
| cgcgtggccc tgcacacctt tggcggcctg accgatctga tccgcgtgcc gccggcggc | 600 |
| agccgccagc ccctggatac cgatggcctg gatgccggcc tgcagtactt tgccatggat | 660 |
| ggccgcgaag tgcgccgctt tgtgaccgaa cacctgcccc agctgatcaa aggctttctg | 720 |
| cacgaagccg gcgtggatgc cgccgatatc agccactttg tgccccacca ggccaacggc | 780 |
| gtgatgctgg atgaagtgtt tggcgaactg cacctgcccc gccaccat gcaccgcacc | 840 |
| gtggaaaacct acggcaacac cggcgccgcc agcatcccca tcaccatgga tgccgccgtg | 900 |
| cgcgccggca gctttcgccc cggcgaactg gtgctgctgg ccggctttgg cggcggcatg | 960 |
| gccgccagct ttgccctgat cgaatggtag | 990 |

<210> SEQ ID NO 3
<211> LENGTH: 1333
<212> TYPE: DNA
<213> ORGANISM: Artificial Sequence
<220> FEATURE:
<223> OTHER INFORMATION: atoDA gene

<400> SEQUENCE: 3

| | |
|---|---|
| atgaaaacca aactgatgac cctccaggat gccaccggct tttttcgcga tggcatgacc | 60 |
| atcatggtgg gcggctttat gggcatcggc accccccagcc gcctggtgga agccctgctg | 120 |
| gaaagcggcg tgcgcgatct gaccctgatc gccaacgata ccgcctttgt ggataccggc | 180 |
| atcggccccc tgatcgtgaa cggcgcgtg cgcaaagtga tcgccagcca catcggcacc | 240 |
| aaccccgaaa ccgccgccg catgatcagc ggcgaaatgg atgtggtgct ggtgccccag | 300 |
| ggcaccctga tcgaacagat ccgctgcggc ggcgccggcc tgggcggctt tctgacccccc | 360 |
| accggcgtgg gcaccgtggt ggaagaaggc aaacagaccc tgaccctgga tggcaaaacc | 420 |
| tggctgctgg aacgccccct gcgcgccgat ctggcccctga tccgcgccca ccgctgcgat | 480 |

```
accctgggca acctgaccta ccagctgagc gcccgcaact ttaaccccct gatcgccctg    540
gccgccgata tcaccctggt ggaacccgat gaactggtgg aaaccggcga actccagccc    600
gatcacatcg tgaccccccgg cgccgtgatc gatcacatca tcgtgagcca ggaaagcaaa    660
tagttaaaga ggagaatact agatggatgc caaacagcgc atcgcccgcc gcgtggccca    720
ggaactgcgc gatggcgata tcgtgaacct gggcatcggc ctgcccacca tggtggccaa    780
ctacctgccc gaaggcatcc acatcaccct ccagagcgaa aacggctttc tgggcctggg    840
ccccgtgacc accgcccacc ccgatctggt gaacgccggc ggccagccct gcggcgtgct    900
gcccggcgcc gccatgtttg atagcgccat gagctttgcc ctgatccgcg gcggccacat    960
cgatgcctgc gtgctgggcg gcctccaggt ggatgaagaa gccaacctgg ccaactgggt   1020
ggtgcccggc aaaatggtgc ccggcatggg cggcgccatg gatctggtga ccggcagccg   1080
caaagtgatc atcgccatgg aacactgcgc caaagatggc agcgccaaaa tcctgcgccg   1140
ctgcaccatg cccctgaccg cccagcacgc cgtgcacatg ctggtgaccg aactggccgt   1200
gtttcgcttt atcgatggca aaatgtggct gaccgaaatc gccgatggct gcgatctggc   1260
caccgtgcgc gccaaaaccg aagcccgctt tgaagtggcc gccgatctga cacccagcg   1320 cggcgatctg tag                                                      1333

<210> SEQ ID NO 4
<211> LENGTH: 1324
<212> TYPE: DNA
<213> ORGANISM: Artificial Sequence
<220> FEATURE:
<223> OTHER INFORMATION: ctfAB gene

<400> SEQUENCE: 4
atgaacagca aaatcatccg ctttgaaaac ctgcgcagct ttttaaaga tggcatgacc      60 atcatgatcg gcggctttct gaactgcggc accccccacca aactgatcga ttttctggtg    120
aacctgaaca tcaaaaacct gaccatcatc agcaacgata cctgctaccc caacaccggc    180
atcggcaaac tgatcagcaa caaccaggtg aaaaaactga tcgccagcta catcggcagc    240
aaccccgata ccggcaaaaa actgtttaac aacgaactgg aagtggaact gagcccccag    300
ggcaccctgg tggaacgcat ccgcgccggc ggcagcggcc tgggcggcgt gctgaccaaa    360
accggcctgg gcaccctgat cgaaaaaggc aaaaaaaaaa tcagcatcaa cggcaccgaa    420
tacctgctgg aactgccccct gaccgccgat atcgccctga tcaaaggcag catcgtggat    480
gaagccggca cacccttttta caaaggcacc accaaaaact ttaaccccta catggccatg    540
gccgccaaaa ccgtgatcgt ggaagccgaa aacctggtga gctgcgaaaa actggaaaaa    600 gaaaagcca tgaccccggg cgtgctgatc aactacatcg tgaaagaacc cgcctaaaat    660
gatcaacgat aaaaacctgg ccaaagaaat catcgccaaa gcgtggccc gcgaactgaa    720 aaacggccag ctggtgaacc tgggcgtggg cctgcccacc atggtggccg attacatccc    780
caaaaacttt aaaatcacct ttcagagcga aaacggcatc gtgggcatgg cgccagccc    840 caaaatcaac gaagccgata agatgtggt gaacgccggc ggcgattaca ccaccgtgct    900 gccccgatggc acctttttg atagcagcgt gagctttagc ctgatccgcg gcggccacgt    960
ggatgtgacc gtgctgggcg ccctccaggt ggatgaaaaa ggcaacatcg ccaactggat   1020
cgtgcccggc aaaatgctga gcggcatggg cggcgccatg gatctggtga acggcgccaa   1080
aaaagtgatc atcgccatgc ccacaccaa caaaggccag cccaaaatcc tgaaaaaatg   1140
```

| | |
|---|---|
| cacccctgccc ctgaccgcca aaagccaggc caacctgatc gtgaccgaac tgggcgtgat | 1200 |
| cgaagtgatc aacgatggcc tgctgctgac cgaaatcaac aaaaacacca ccatcgatga | 1260 |
| aatccgcagc ctgaccgccg ccgatctgct gatcagcaac gaactgcgcc ccatggccgt | 1320 |
| gtag | 1324 |

```
<210> SEQ ID NO 5
<211> LENGTH: 735
<212> TYPE: DNA
<213> ORGANISM: Artificial Sequence
<220> FEATURE:
<223> OTHER INFORMATION: adc gene

<400> SEQUENCE: 5
```

| | |
|---|---|
| atgctgaaag atgaagtgat caaacagatc agcaccccccc tgaccagccc cgcctttccc | 60 |
| cgcggcccct acaaatttca caaccgcgaa tactttaaca tcgtgtaccg caccgatatg | 120 |
| gatgccctgc gcaaagtggt gcccgaaccc ctggaaatcg atgaacccct ggtgcgcttt | 180 |
| gaaatcatgg ccatgcacga taccagcggc ctgggctgct acaccgaaag cggccaggcc | 240 |
| atccccgtga gctgcaacgg cgtgaaaggc gattacctgc acatgatgta cctggataac | 300 |
| gaacccgcca tcgccgtggg ccgcgaactg agcgcctacc ccaaaaaact gggctacccc | 360 |
| aaactgtttg tggatagcga taccctggtg ggcaccctgg attacggcaa actgcgcgtg | 420 |
| gccaccgcca ccatgggcta caaacacaaa gccctggatg ccaacgaagc caagatcag | 480 |
| atttgccgcc ccaactacat gctgaaaatc atccccaact acgatggcag ccccgcatc | 540 |
| tgcgaactga tcaacgccaa aatcaccgat gtgaccgtgc acgaagcctg gaccggcccc | 600 |
| acccgcctcc agctgtttga tcacgccatg gcccccctga cgatctgcc cgtgaaagaa | 660 |
| atcgtgagca gcagccacat cctggccgat atcatcctgc ccgcgccga agtgatctac | 720 |
| gattacctga aatag | 735 |

```
<210> SEQ ID NO 6
<211> LENGTH: 8481
<212> TYPE: DNA
<213> ORGANISM: Artificial Sequence
<220> FEATURE:
<223> OTHER INFORMATION: pSe1Bb1s-atoB-atoDA-adc vector

<400> SEQUENCE: 6
```

| | |
|---|---|
| gataatctca tgaccaaaat cccttaacgt gagttttcgt tccactgagc gtcagacccc | 60 |
| gtagaaaaga tcaaaggatc ttcttgagat cctttttttc tgcgcgtaat ctgctgcttg | 120 |
| caaacaaaaa aaccaccgct accagcggtg gtttgtttgc cggatcaaga gctaccaact | 180 |
| cttttttccga aggtaactgg cttcagcaga gcgcagatac caaatactgt tcttctagtg | 240 |
| tagccgtagt taggccacca cttcaagaac tctgtagcac cgcctacata cctcgctctg | 300 |
| ctaatcctgt taccagtggc tgctgccagt ggcgataagt cgtgtcttac cgggttggac | 360 |
| tcaagacgat agttaccgga taaggcgcag cggtcgggct gaacggggg ttcgtgcaca | 420 |
| cagcccagct tggagcgaac gacctacacc gaactgagat acctacagcg tgagctatga | 480 |
| gaaagcgcca cgcttcccga agggagaaag gcggacaggt atccggtaag cggcagggtc | 540 |
| ggaacaggag agcgcacgag ggagcttcca gggggaaacg cctggtatct ttatagtcct | 600 |
| gtcgggtttc gccacctctg acttgagcgt cgatttttgt gatgctcgtc aggggggcgg | 660 |
| agcctatgga aaaacgccag caacgcggcc ttttacgtt cctgggcctt ttgctggcct | 720 |
| tttgctcaca tgtgtgctgg gccccaatgc cttctccaag ggcggcattc ccctgactgt | 780 |

```
tgaaggcgtt gccaatatca agattgctgg ggaagaaccg accatccaca acgcgatcga    840
gcggctgctt ggcaaaaacc gtaaggaaat cgagcaaatt gccaaggaga ccctcgaagg    900
caacttgcgt ggtgttttag ccagcctcac gccggagcag atcaacgagg acaaaattgc    960
ctttgccaaa agtctgctgg aagaggcgga ggatgacctt gagcagctgg gtctagtcct   1020
cgatacgctg caagtccaga acatttccga tgaggtcggt tatctctcgg ctagtggacg   1080
caagcagcgg gctgatctgc agcgagatgc ccgaattgct gaagccgatg cccaggctgc   1140
ctctgcgatc caaacggccg aaaatgacaa gatcacggcc ctgcgtcgga tcgatcgcga   1200
tgtagcgatc gcccaagccg aggccgagcg ccggattcag gatgcgttga cgcggcgcga   1260
agcggtggtg gccgaagctg aagcggacat tgctaccgaa gtcgctcgta gccaagcaga   1320
actccctgtg cagcaggagc ggatcaaaca ggtgcagcag caacttcaag ccgatgtgat   1380
cgccccagct gaggcagctt gtaaacgggc gatcgcggaa gcgcgggggg ccgccgcccg   1440
tatcgtcgaa gatggaaaag ctcaagcgga agggacccaa cggctggcgg aggcttggca   1500
gaccgctggt gctaatgccc gcgacatctt cctgctccag aagtctagac cagccaggac   1560
agaaatgcct cgacttcgct gctacccaag gttgccgggt gacgcacacc gtggaaacgg   1620
atgaaggcac gaacccagtg gacataagcc tgttcggttc gtaagctgta atgcaagtag   1680
cgtatgcgct cacgcaactg gtccagaacc ttgaccgaac gcagcggtgg taacggcgca   1740
gtggcggttt tcatggcttg ttatgactgt tttttggggg tacagtctat gcctcgggca   1800
tccaagcagc aagcgcgtta cgccgtgggt cgatgtttga tgttatggag cagcaacgat   1860
gttacgcagc agggcagtcg ccctaaaaca aagttaaaca ttatgaggga agcggtgatc   1920
gccgaagtat cgactcaact atcagaggta gttggcgtca tcgagcgcca tctcgaaccg   1980
acgttgctgg ccgtacattt gtacggctcc gcagtggatg gcggcctgaa gccacacagt   2040
gatattgatt tgctggttac ggtgaccgta aggcttgatg aaacaacgcg gcgagctttg   2100
atcaacgacc ttttggaaac ttcggcttcc cctggagaga gcgagattct ccgcgctgta   2160
gaagtcacca ttgttgtgca cgacgacatc attccgtggc gttatccagc taagcgcgaa   2220
ctgcaatttg gagaatggca gcgcaatgac attcttgctg gtatcttcga gccagccacg   2280
atcgacattg atctggctat cttgctgaca aaagcaagag aacatagcgt tgccttggta   2340
ggtccagcgg cggaggaact cttttgatccg gttcctgaac aggatctatt tgaggcgcta   2400
aatgaaacct taacgctatg gaactcgccg cccgactggg ctggcgatga gcgaaatgta   2460
gtgcttacgt tgtcccgcat ttggtacagc gcagtaaccg gcaaaatcgc gccgaaggat   2520
gtcgctgccg actgggcaat ggagcgcctg ccggcccagt atcagcccgt catacttgaa   2580
gctagacagg cttatcttgg acaagaagaa gatcgcttgg cctcgcgcgc agatcagttg   2640
gaagaatttg tccactacgt gaaaggcgag atcaccaagg tagtcggcaa ataacctcat   2700
tttcgccaga tatcgacgtc gacaccatcg aatggtgcaa aacctttcgc ggtatggcat   2760
gatagcgccc ggaagagagt caattcaggg tggtgaatgt gaaaccagta acgttatacg   2820
atgtcgcaga gtatgccggt gtctcttatc agaccgtttc ccgcgtggtg aaccaggcca   2880
gccacgtttc tgcgaaaacg cgggaaaaag tggaagcggc gatggcggag ctgaattaca   2940
ttcccaaccg cgtggcacaa caactggcgg gcaaacagtc gttgctgatt ggcgttgcca   3000
cctccagtct ggccctgcac gcgccgtcgc aaattgtcgc ggcgattaaa tctcgcgccg   3060
atcaactggg tgccagcgtg gtggtgtcga tggtagaacg aagcggcgtc gaagcctgta   3120
```

```
aagcggcggt gcacaatctt ctcgcgcaac gcgtcagtgg gctgatcatt aactatccgc    3180
tggatgacca ggatgccatt gctgtggaag ctgcctgcac taatgttccg gcgttatttc    3240
ttgatgtctc tgaccagaca cccatcaaca gtattatttt ctcccatgaa gacggtacgc    3300
gactgggcgt ggagcatctg gtcgcattgg gtcaccagca aatcgcgctg ttagcgggcc    3360
cattaagttc tgtctcggcg cgtctgcgtc tggctggctg gcataaatat ctcactcgca    3420
atcaaattca gccgatagcg gaacgggaag gcgactggag tgccatgtcc ggttttcaac    3480
aaaccatgca aatgctgaat gagggcatcg ttcccactgc gatgctggtt gccaacgatc    3540
agatggcgct gggcgcaatg cgcgccatta ccgagtccgg gctgcgcgtt ggtgcggata    3600
tctcggtagt gggatacgac gataccgaag acagctcatg ttatatcccg ccgttaacca    3660
ccatcaaaca ggattttcgc ctgctggggc aaaccagcgt ggaccgcttg ctgcaactct    3720
ctcagggcca ggcggtgaag ggcaatcagc tgttgcccgt ctcactggtg aaaagaaaaa    3780
ccaccctggc gcccaatacg caaaccgcct ctccccgcgc gttggccgat tcattaatgc    3840
agctggcacg acaggtttcc cgactgggaa gcgggcagtg agcgcaacgc aattaatgta    3900
agttagcgcg aattgatctg gtttgacagc ttatcatcga ctgcacggtg caccaatgct    3960
tctggcgtca ggcagccatc ggaagctgtg gtatggctgt gcaggtcgta aatcactgca    4020
taattcgtgt cgctcaaggc gcactcccgt tctggataat gttttttgcg ccgacatcat    4080
aacggttctg gcaaatattc tgaaatgagc tgttgacaat taatcatccg gctcgtataa    4140
tgtgtggaat tgtgagcgga taacaatttc agaattcaaa agatctttaa agaggagaat    4200
actagatgaa aaactgcgtg atcgtgagcg ccgtgcgcac cgccatcggc agctttaacg    4260
gcagcctggc cagcaccagc gccatcgatc tgggcgccac cgtgatcaaa gccgccatcg    4320
aacgcgccaa aatcgatagc cagcacgtgg atgaagtgat catgggcaac gtgctccagg    4380
ccggcctggg ccagaacccc gcccgccagg ccctgctgaa agcggcctg gccgaaaccg    4440 tgtgcggctt taccgtgaac aaagtgtgcg gcagcggcct gaaaagcgtg gccctggccg    4500
cccaggccat ccaggccggc caggcccaga gcatcgtggc cggcggcatg gaaaacatga    4560
gcctggcccc ctacctgctg gatgccaaag cccgcagcgg ctaccgcctg ggcgatggcc    4620
aggtgtacga tgtgatcctg cgcgatggcc tgatgtgcgc cacccacggc taccacatgg    4680
gcatcaccgc cgaaaacgtg gccaaagaat acggcatcac ccgcgaaatg caggatgaac    4740
tggccctgca cagccagcgc aaagccgccg ccgccatcga aagcggcgcc tttaccgccg    4800
aaatcgtgcc cgtgaacgtg gtgacccgca aaaaaacctt tgtgtttagc caggatgaat    4860
ttcccaaagc caacagcacc gccgaagccc tgggcgccct gcgccccgcc tttgataaag    4920
ccggcaccgt gaccgccggc aacgccagcg gcatcaacga tggcgccgcc gcctggtga    4980 tcatggaaga aagcgccgcc ctggccgccg gcctgacccc cctggccgc atcaaaagct    5040 acgcagcgg cggcgtgccc cccgcccctga tgggcatggg ccccgtgccc gccacccaga    5100 aagcccctcca gctggccggc ctccagctgg ccgatatcga tctgatcgaa gccaacgaag    5160
cctttgccgc ccagtttctg gccgtgggca aaaacctggg ctttgatagc gaaaaagtga    5220
acgtgaacgg cggcgccatc gccctgggcc accccatcgg cgccagcggc gcccgcatcc    5280
tggtgaccct gctgcacgcc atgcaggccc gcgataaaac cctgggcctg gccacccctgt    5340 gcatcggcgg cggccagggc atcgccatgg tgatcgaacg cctgaactag aagaggagaa    5400
atactagatg aaaaccaaac tgatgaccct ccaggatgcc accggctttt ttcgcgatgg    5460
catgaccatc atggtgggcg gctttatggg catcggcacc cccagccgcc tggtggaagc    5520
```

```
cctgctggaa agcggcgtgc gcgatctgac cctgatcgcc aacgataccg cctttgtgga   5580
taccggcatc ggcccccctga tcgtgaacgg ccgcgtgcgc aaagtgatcg ccagccacat   5640
cggcaccaac cccgaaaccg gccgccgcat gatcagcggc gaaatggatg tggtgctggt   5700
gccccagggc accctgatcg aacagatccg ctgcggcggc gccggcctgg gcggctttct   5760
gaccccacc ggcgtgggca ccgtggtgga agaaggcaaa cagaccctga ccctggatgg   5820
caaaaccctgg ctgctggaac gcccctgcg cgccgatctg gccctgatcc gcgcccaccg   5880
ctgcgatacc ctgggcaacc tgacctacca gctgagcgcc cgcaactta accccctgat   5940
cgccctggcc gccgatatca ccctggtgga acccgatgaa ctggtggaaa ccggcgaact   6000
ccagcccgat cacatcgtga ccccggcgc cgtgatcgat cacatcatcg tgagccagga   6060
aagcaaaatag ttaaagagga gaatactaga tggatgccaa acagcgcatc gcccgccgcg   6120
tggcccagga actgcgcgat ggcgatatcg tgaacctggg catcggcctg cccaccatgg   6180
tggccaacta cctgcccgaa ggcatccaca tcaccctcca gagcgaaaac ggctttctgg   6240
gcctgggccc cgtgaccacc gcccaccccg atctggtgaa cgccggcggc cagccctgcg   6300
gcgtgctgcc cggcgccgcc atgtttgata gcgccatgag ctttgccctg atccgcggcg   6360
gccacatcga tgcctgcgtg ctgggcggcc tccaggtgga tgaagaagcc aacctggcca   6420
actgggtggt gcccggcaaa atggtgcccg gcatgggcgg cgccatggat ctggtgaccg   6480
gcagccgcaa agtgatcatc gccatggaac actgcgccaa agatggcagc gccaaaatcc   6540
tgcgccgctg caccatgccc ctgaccgccc agcacgccgt gcacatgctg gtgaccgaac   6600
tggccgtgtt tcgctttatc gatggcaaaa tgtggctgac cgaaatcgcc gatggctgcg   6660
atctggccac cgtgcgcgcc aaaaccgaag cccgctttga gtggccgcc gatctgaaca   6720
cccagcgcgg cgatctgtag ggatctggat cttaaagag gagaatacta gatgctgaaa   6780
gatgaagtga tcaaacagat cagcaccccc ctgaccagcc ccgccttcc ccgcggcccc   6840
tacaaatttc acaaccgcga atactttaac atcgtgtacc gcaccgatat ggatgccctg   6900
cgcaaagtgg tgcccgaacc cctggaaatc gatgaacccc tggtgcgctt tgaaatcatg   6960
gccatgcacg ataccagcgg cctgggctgc tacaccgaaa gcggcaggc catccccgtg   7020
agctgcaacg gcgtgaaagg cgattacctg cacatgatgt acctggataa cgaacccgcc   7080
atcgccgtgg gccgcgaact gagcgcctac cccaaaaaac tgggctaccc caaactgttt   7140
gtggatagcg atacccctgg gggcaccctg gattacggca aactgcgcgt ggccaccgcc   7200
accatgggct acaaacacaa agccctggat gccaacgaag ccaaagatca gatttgccgc   7260
cccaactaca tgctgaaaat catccccaac tacgatggca gcccccgcat ctgcgaactg   7320
atcaacgcca aaatcaccga tgtgaccgtg cacgaagcct ggaccggccc cacccgcctc   7380
cagctgtttg atcacgccat ggccccctg aacgatctgc ccgtgaaaga aatcgtgagc   7440
agcagccaca tcctggccga tatcatcctg ccccgcgccg aagtgatcta cgattacctg   7500
aaatagctcg agtaaggatc tccaggcatc aaataaacg aaaggctcag tcgaaagact   7560
gggccttttcg tttatctgt tgtttgtcgg tgaacgctct ctactagagt cacactggct   7620
caccttcggg tgggcctttc tgcgtttata cctagggcgt tcggctgcgg cgagcggtat   7680
cagctcactc aaaggcggta atacgtccct gctcgtcacg ctttcaggca ccgtgccaga   7740
tatcgacgtg gagtcgatca ctgtgattgg cgaagggga ggcagcgcta cccaaatcgc   7800
tagcttgctg gagaagctga aacaaaccac gggcattgat ctggcgaaat ccctaccggg   7860
```

| | |
|---|---|
| tcaatccgac tcgcccgctg cgaagtccta agagatagcg atgtgaccgc gatcgcttgt | 7920 |
| caagaatccc agtgatcccg aaccatagga aggcaagctc aatgcttgcc tcgtcttgag | 7980 |
| gactatctag atgtctgtgg aacgcacatt tattgccatc aagcccgatg gcgttcagcg | 8040 |
| gggtttggtc ggtacgatca tcggccgctt tgagcaaaaa ggcttcaaac tggtgggcct | 8100 |
| aaagcagctg aagcccagtc gcgagctggc cgaacagcac tatgctgtcc accgcgagcg | 8160 |
| cccctttcttc aatggcctcg tcgagttcat cacctctggg ccgatcgtgg cgatcgtctt | 8220 |
| ggaaggcgaa ggcgttgtgg cggctgctcg caagttgatc ggcgctacca atccgctgac | 8280 |
| ggcagaaccg gcaccatcc gtggtgattt tggtgtcaat attggccgca acatcatcca | 8340 |
| tggctcggat gcaatcgaaa cagcacaaca ggaaattgct ctctggttta gcccagcaga | 8400 |
| gctaagtgat tggacccccca cgattcaacc ctggctgtac gaataaggtc tgcattcctt | 8460 |
| cagagagaca ttgccatgcc c | 8481 |

<210> SEQ ID NO 7
<211> LENGTH: 8452
<212> TYPE: DNA
<213> ORGANISM: Artificial Sequence
<220> FEATURE:
<223> OTHER INFORMATION: pSe1Bb1s-atoB-ctfAB-adc vector

<400> SEQUENCE: 7

| | |
|---|---|
| gataatctca tgaccaaaat cccttaacgt gagttttcgt tccactgagc gtcagacccc | 60 |
| gtagaaaaga tcaaaggatc ttcttgagat cctttttttc tgcgcgtaat ctgctgcttg | 120 |
| caaacaaaaa aaccaccgct accagcggtg gtttgtttgc cggatcaaga gctaccaact | 180 |
| ctttttccga aggtaactgg cttcagcaga gcgcagatac caaatactgt tcttctagtg | 240 |
| tagccgtagt taggccacca cttcaagaac tctgtagcac cgcctacata cctcgctctg | 300 |
| ctaatcctgt taccagtggc tgctgccagt ggcgataagt cgtgtcttac cgggttggac | 360 |
| tcaagacgat agttaccgga taaggcgcag cggtcgggct gaacggggg ttcgtgcaca | 420 |
| cagcccagct tggagcgaac gacctacacc gaactgagat acctacagcg tgagctatga | 480 |
| gaaagcgcca cgcttcccga agggagaaag gcggacaggt atccggtaag cggcagggtc | 540 |
| ggaacaggag agcgcacgag ggagcttcca gggggaaacg cctggtatct ttatagtcct | 600 |
| gtcgggtttc gccacctctg acttgagcgt cgatttttgt gatgctcgtc aggggggcgg | 660 |
| agcctatgga aaaacgccag caacgcggcc ttttttacggt tcctggcctt tgctggcct | 720 |
| tttgctcaca tgtgtgctgg gccccaatgc cttctccaag gcggcattc ccctgactgt | 780 |
| tgaaggcgtt gccaatatca agattgctgg ggaagaaccg accatccaca acgcgatcga | 840 |
| gcggctgctt ggcaaaaacc gtaaggaaat cgagcaaatt gccaaggaga ccctcgaagg | 900 |
| caacttgcgt ggtgttttag ccagcctcac gccggagcag atcaacgagg acaaaattgc | 960 |
| ctttgccaaa agtctgctgg aagaggcgga ggatgacctt gagcagctgg gtctagtcct | 1020 |
| cgatacgctg caagtccaga acatttccga tgaggtcggt tatctctcgg ctagtggacg | 1080 |
| caagcagcgg gctgatctgc agcgagatgc ccgaattgct gaagccgatg cccaggctgc | 1140 |
| ctctgcgatc caaacggccg aaaatgacaa gatcacggcc ctgcgtcgga tcgatcgcga | 1200 |
| tgtagcgatc gcccaagccg aggccgagcg ccggattcag gatgcgttga cgcggcgcga | 1260 |
| agcggtggtg gccgaagctg aagcggacat tgctaccgaa gtcgctcgta gccaagcaga | 1320 |
| actccctgtg cagcaggagc ggatcaaaca ggtgcagcag caacttcaag ccgatgtgat | 1380 |
| cgccccagct gaggcagctt gtaaacgggc gatcgcggaa gcgcgggggg ccgccgcccg | 1440 |

```
tatcgtcgaa gatggaaaag ctcaagcgga agggacccaa cggctggcgg aggcttggca    1500
gaccgctggt gctaatgccc gcgacatctt cctgctccag aagtctagac cagccaggac    1560
agaaatgcct cgacttcgct gctacccaag gttgccgggt gacgcacacc gtggaaacgg    1620
atgaaggcac gaacccagtg gacataagcc tgttcggttc gtaagctgta atgcaagtag    1680
cgtatgcgct cacgcaactg gtccagaacc ttgaccgaac gcagcggtgg taacggcgca    1740
gtggcggttt tcatggcttg ttatgactgt ttttttgggg tacagtctat gcctcgggca    1800
tccaagcagc aagcgcgtta cgccgtgggt cgatgtttga tgttatggag cagcaacgat    1860
gttacgcagc agggcagtcg ccctaaaaca aagttaaaca ttatgaggga agcggtgatc    1920
gccgaagtat cgactcaact atcagaggta gttggcgtca tcgagcgcca tctcgaaccg    1980
acgttgctgg cctacatttt gtacggctcc gcagtggatg gcggcctgaa gccacacagt    2040
gatattgatt tgctggttac ggtgaccgta aggcttgatg aaacaacgcg gcgagctttg    2100
atcaacgacc ttttggaaac ttcggcttcc cctggagaga gcgagattct ccgcgctgta    2160
gaagtcacca ttgttgtgca cgacgacatc attccgtggc gttatccagc taagcgcgaa    2220
ctgcaatttg gagaatggca gcgcaatgac attcttgctg gtatcttcga gccagccacg    2280
atcgacattg atctggctat cttgctgaca aaagcaagag aacatagcgt tgccttggta    2340
ggtccagcgg cggaggaact cttttgatccg gttcctgaac aggatctatt tgaggcgcta    2400
aatgaaacct taacgctatg gaactcgccg cccgactggg ctggcgatga gcgaaatgta    2460
gtgcttacgt tgtcccgcat ttggtacagc gcagtaaccg gcaaaatcgc gccgaaggat    2520
gtcgctgccg actgggcaat ggagcgcctg ccggcccagt atcagcccgt catacttgaa    2580
gctagacagg cttatcttgg acaagaagaa gatcgcttgg cctcgcgcgc agatcagttg    2640
gaagaatttg tccactacgt gaaaggcgag atcaccaagg tagtcggcaa ataacctcat    2700
tttcgccaga tatcgacgtc gacaccatcg aatggtgcaa aacctttcgc ggtatggcat    2760
gatagcgccc ggaagagagt caattcaggg tggtgaatgt gaaaccagta acgttatacg    2820
atgtcgcaga gtatgccggt gtctcttatc agaccgtttc ccgcgtggtg aaccaggcca    2880
gccacgtttc tgcgaaaacg cgggaaaaag tggaagcggc gatggcggag ctgaattaca    2940
ttcccaaccg cgtggcacaa caactggcgg gcaaacagtc gttgctgatt ggcgttgcca    3000
cctccagtct ggccctgcac gcgccgtcgc aaattgtcgc ggcgattaaa tctcgcgccg    3060
atcaactggg tgccagcgtg gtggtgtcga tggtagaacg aagcggcgtc gaagcctgta    3120
aagcggcggt gcacaatctt ctcgcgcaac gcgtcagtgg gctgatcatt aactatccgc    3180
tggatgacca ggatgccatt gctgtggaag ctgcctgcac taatgttccg gcgttatttc    3240
ttgatgtctc tgaccagaca cccatcaaca gtattatttt ctcccatgaa gacggtacgc    3300
gactgggcgt ggagcatctg gtcgcattgg gtcaccagca atcgcgctg ttagcgggcc    3360
cattaagttc tgtctcggcg cgtctgcgtc tggctggctg gcataaatat ctcactcgca    3420
atcaaattca gccgatagcg gaacgggaag gcgactggag tgccatgtcc ggttttcaac    3480
aaaccatgca aatgctgaat gagggcatcg ttcccactgc gatgctggtt gccaacgatc    3540
agatggcgct gggcgcaatg cgcgccatta ccgagtccgg gctgcgcgtt ggtgcggata    3600
tctcggtagt gggatacgac gataccgaag acagctcatg ttatatcccg ccgttaacca    3660
ccatcaaaca ggattttcgc ctgctggggc aaaccagcgt ggaccgcttg ctgcaactct    3720
ctcagggcca ggcggtgaag ggcaatcagc tgttgcccgt ctcactggtg aaaagaaaaa    3780
```

```
ccaccctggc gcccaatacg caaaccgcct ctccccgcgc gttggccgat tcattaatgc   3840
agctggcacg acaggtttcc cgactggaaa gcgggcagtg agcgcaacgc aattaatgta   3900
agttagcgcg aattgatctg gtttgacagc ttatcatcga ctgcacggtg caccaatgct   3960
tctggcgtca ggcagccatc ggaagctgtg gtatggctgt gcaggtcgta atcactgca   4020
taattcgtgt cgctcaaggc gcactcccgt tctggataat aacggttctg gcaaatattc   4080
tgaaatgagc tgttgacaat taatcatccg gctcgtataa tgtgtggaat tgtgagcgga   4140
taacaatttc agaattcaaa agatctttaa agaggagaat actagatgaa aaactgcgtg   4200
atcgtgagcg ccgtgcgcac cgccatcggc agctttaacg gcagcctggc cagcaccagc   4260
gccatcgatc tgggcgccac cgtgatcaaa gccgccatcg aacgcgccaa aatcgatagc   4320
cagcacgtgg atgaagtgat catgggcaac gtgctccagg ccggcctggg ccagaacccc   4380
gcccgccagg ccctgctgaa aagcggcctg gccgaaaccg tgtgcggctt taccgtgaac   4440
aaagtgtgcg gcagcggcct gaaaagcgtg gccctggccg cccaggccat ccaggccggc   4500
caggcccaga gcatcgtggc cggcggcatg gaaaacatga cctggccccc ctacctgctg   4560
gatgccaaag cccgcagcgg ctaccgcctg ggcgatggcc aggtgtacga tgtgatcctg   4620
cgcgatggcc tgatgtgcgc cacccacggc taccacatgg gcatcaccgc cgaaaacgtg   4680
gccaaagaat acggcatcac ccgcgaaatg caggatgaac tggccctgca cagccagcgc   4740
aaagccgccg ccgccatcga aagcggcgcc tttaccgccg aaatcgtgcc cgtgaacgtg   4800
gtgacccgca aaaaaacctt tgtgtttagc caggatgaat ttcccaaagc caacagcacc   4860
gccgaagccc tgggcgccct cgccccgcc tttgataaag ccggcaccgt gaccgccggc   4920
aacgccagcg gcatcaacga tggcgccgcc gccctggtga tcatggaaga aagcgccgcc   4980
ctggccgccg gctgaccccc ctggcccgc atcaaaagct acgccagcgg cggcgtgccc   5040
cccgccctga tgggcatggg ccccgtgccc gccacccaga aagccctcca gctggccggc   5100
ctccagctgg ccgatatcga tctgatcgaa gccaacgaag cctttgccgc ccagtttctg   5160
gccgtgggca aaaacctggg ctttgatagc gaaaaagtga acgtgaacgg cggcgccatc   5220
gccctgggcc accccatcgg cgccagcggc gcccgcatcc tggtgaccct gctgcacgcc   5280
atgcaggccc gcgataaaac cctgggcctg gccaccctgt gcatcggcgg cggccagggc   5340
atcgccatgg tgatcgaacg cctgaactag aagaggagaa atactagatg aacagcaaaa   5400
tcatccgctt tgaaaacctg cgcagctttt ttaaagatgg catgaccatc atgatcggcg   5460
gctttctgaa ctgcggcacc cccaccaaac tgatcgattt tctggtgaac ctgaacatca   5520
aaaacctgac catcatcagc aacgatacct gctaccccaa caccggcatc ggcaaactga   5580
tcagcaacaa ccaggtgaaa aaactgatcc cagctacat cggcagcaac cccgataccg   5640
gcaaaaaact gtttaacaac gaactggaag tggaactgag cccccagggc accctggtgg   5700
aacgcatccg cgccggcggc agcggcctgg gcggcgtgct gaccaaaacc ggcctgggca   5760
ccctgatcga aaaaggcaaa aaaaaatca gcatcaacgg caccgaatac ctgctggaac   5820
tgccctgac cgccgatatc gccctgatca aaggcagcat cgtggatgaa gccggcaaca   5880
ccttttacaa aggcaccacc aaaaacttta accctacat ggccatggcc gccaaaaccg   5940
tgatcgtgga agccgaaaac ctggtgagct gcgaaaaact ggaaaagaa aaagccatga   6000
cccccggcgt gctgatcaac tacatcgtga agaacccgc ctaaaatgat caacgataaa   6060
aacctggcca agaaatcat cgccaaacgc gtggcccgcg aactgaaaaa cggccagctg   6120
gtgaacctgg gcgtgggcct gcccaccatg gtggccgatt acatccccaa aaactttaaa   6180
```

```
atcacctttc agagcgaaaa cggcatcgtg gcatgggcg ccagccccaa aatcaacgaa    6240
gccgataaag atgtggtgaa cgccggcggc gattacacca ccgtgctgcc cgatggcacc    6300 tttttgata gcagcgtgag ctttagcctg atccgcggcg ccacgtgga tgtgaccgtg    6360 ctgggcgccc tccaggtgga tgaaaaaggc aacatcgcca actggatcgt gcccggcaaa    6420
atgctgagcg gcatgggcgg cgccatggat ctggtgaacg gcgccaaaaa agtgatcatc    6480
gccatgcgcc acaccaacaa aggccagccc aaaatcctga aaaaatgcac cctgcccctg    6540
accgccaaaa gccaggccaa cctgatcgtg accgaactgg gcgtgatcga agtgatcaac    6600
gatggcctgc tgctgaccga aatcaacaaa acaccacca tcgatgaaat ccgcagcctg    6660
accgccgccg atctgctgat cagcaacgaa ctgcgcccca tggccgtgta gggatctgga    6720
tctttaaaga ggagaatact agatgctgaa agatgaagtg atcaaacaga tcagcacccc    6780
cctgaccagc cccgcctttc cccgcggccc ctacaaattt cacaaccgcg aatactttaa    6840
catcgtgtac cgcaccgata tggatgccct gcgcaaagtg gtgcccgaac ccctggaaat    6900
cgatgaaccc ctggtgcgct ttgaaatcat ggccatgcac gataccagcg gcctgggctg    6960
ctacaccgaa agcggccagg ccatccccgt gagctgcaac ggcgtgaaag gcgattacct    7020
gcacatgatg tacctggata cgaacccgc catcgccgtg ggccgcgaac tgagcgccta    7080
ccccaaaaaa ctgggctacc ccaaactgtt tgtggatagc gatacccctgg tgggcaccct    7140 ggattacggc aaactgcgcg tggccaccgc caccatgggc tacaaacaca aagccctgga    7200
tgccaacgaa gccaaagatc agatttgccg ccccaactac atgctgaaaa tcatccccaa    7260
ctacgatggc agccccgca tctgcgaact gatcaacgcc aaaatcaccg atgtgaccgt    7320
gcacgaagcc tggaccggcc ccacccgcct ccagctgttt gatcacgcca tggccccccct    7380 gaacgatctg cccgtgaaag aaatcgtgag cagcagccac atcctggccg atatcatcct    7440
gccccgcgcc gaagtgatct acgattacct gaaatagctc gagtaaggat ctccaggcat    7500
caaataaaac gaaaggctca gtcgaaagac tgggcctttc gttttatctg ttgtttgtcg    7560
gtgaacgctc tctactagag tcacactggc tcaccttcgg gtgggccttt ctgcgtttat    7620
acctagggcg ttcggctgcg cgagcggta tcagctcact caaaggcggt aatacgtccc    7680
tgctcgtcac gctttcaggc accgtgccag atatcgacgt ggagtcgatc actgtgattg    7740
gcgaagggga aggcagcgct acccaaatcg ctagcttgct ggagaagctg aaacaaacca    7800
cgggcattga tctggcgaaa tccctaccgg gtcaatccga ctcgcccgct gcgaagtcct    7860
aagagatagc gatgtgaccg cgatcgcttg tcaagaatcc cagtgatccc gaaccatagg    7920
aaggcaagct caatgcttgc ctcgtcttga ggactatcta gatgtctgtg aacgcacat    7980 ttattgccat caagcccgat ggcgttcagc ggggttggt cggtacgatc atcgccgct    8040 ttgagcaaaa aggcttcaaa ctggtgggcc taaagcagct gaagcccagt cgcgagctgg    8100
ccgaacagca ctatgctgtc caccgcgagc gcccccttctt caatggcctc gtcgagttca    8160
tcacctctgg gccgatcgtg gcgatcgtct tggaaggcga aggcgttgtg gcggctgctc    8220
gcaagttgat cggcgctacc aatccgctga cggcagaacc gggcaccatc cgtggtgatt    8280
ttggtgtcaa tattggccgc aacatcatcc atggctcgga tgcaatcgaa acagcacaac    8340
aggaaattgc tctctggttt agcccagcag agctaagtga ttggacccc acgattcaac    8400 cctggctgta cgaataaggt ctgcattcct tcagagagac attgccatgc cc          8452
```

<210> SEQ ID NO 8

<211> LENGTH: 8291
<212> TYPE: DNA
<213> ORGANISM: Artificial Sequence
<220> FEATURE:
<223> OTHER INFORMATION: pSe1Bb1s-nphT7-atoDA-adc vector

<400> SEQUENCE: 8

| | | | | | |
|---|---|---|---|---|---|
| gataatctca | tgaccaaaat | cccttaacgt | gagttttcgt | tccactgagc | gtcagacccc | 60 |
| gtagaaaaga | tcaaaggatc | ttcttgagat | ccttttttc | tgcgcgtaat | ctgctgcttg | 120 |
| caaacaaaaa | aaccaccgct | accagcggtg | gtttgtttgc | cggatcaaga | gctaccaact | 180 |
| ctttttccga | aggtaactgg | cttcagcaga | gcgcagatac | caaatactgt | tcttctagtg | 240 |
| tagccgtagt | taggccacca | cttcaagaac | tctgtagcac | cgcctacata | cctcgctctg | 300 |
| ctaatcctgt | taccagtggc | tgctgccagt | ggcgataagt | cgtgtcttac | cgggttggac | 360 |
| tcaagacgat | agttaccgga | taaggcgcag | cggtcgggct | gaacggggg | ttcgtgcaca | 420 |
| cagcccagct | tggagcgaac | gacctacacc | gaactgagat | acctacagcg | tgagctatga | 480 |
| gaaagcgcca | cgcttcccga | agggagaaag | gcggacaggt | atccggtaag | cggcagggtc | 540 |
| ggaacaggag | agcgcacgag | ggagcttcca | gggggaaacg | cctggtatct | ttatagtcct | 600 |
| gtcgggtttc | gccacctctg | acttgagcgt | cgatttttgt | gatgctcgtc | aggggggcgg | 660 |
| agcctatgga | aaaacgccag | caacgcggcc | tttttacggt | tcctggcctt | ttgctggcct | 720 |
| tttgctcaca | tgtgtgctgg | gccccaatgc | cttctccaag | gcggcattc | ccctgactgt | 780 |
| tgaaggcgtt | gccaatatca | agattgctgg | ggaagaaccg | accatccaca | acgcgatcga | 840 |
| gcggctgctt | ggcaaaaacc | gtaaggaaat | cgagcaaatt | gccaaggaga | ccctcgaagg | 900 |
| caacttgcgt | ggtgttttag | ccagcctcac | gccggagcag | atcaacgagg | acaaaattgc | 960 |
| ctttgccaaa | agtctgctgg | aagaggcgga | ggatgacctt | gagcagctgg | gtctagtcct | 1020 |
| cgatacgctg | caagtccaga | acatttccga | tgaggtcggt | tatctctcgg | ctagtggacg | 1080 |
| caagcagcgg | gctgatctgc | agcgagatgc | ccgaattgct | gaagccgatg | cccaggctgc | 1140 |
| ctctgcgatc | caaacggccg | aaaatgacaa | gatcacggcc | ctgcgtcgga | tcgatcgcga | 1200 |
| tgtagcgatc | gcccaagccg | aggccgagcg | ccggattcag | gatgcgttga | gcggcgcga | 1260 |
| agcggtggtg | gccgaagctg | aagcggacat | tgctaccgaa | gtcgctcgta | gccaagcaga | 1320 |
| actccctgtg | cagcaggagc | ggatcaaaca | ggtgcagcag | caacttcaag | ccgatgtgat | 1380 |
| cgccccagct | gaggcagctt | gtaaacgggc | gatcgcggaa | gcgcgggggg | ccgccgcccg | 1440 |
| tatcgtcgaa | gatggaaaag | ctcaagcgga | agggacccaa | cggctggcgg | aggcttggca | 1500 |
| gaccgctggt | gctaatgccc | gcgacatctt | cctgctccag | aagtctagac | cagccaggac | 1560 |
| agaaatgcct | cgacttcgct | gctacccaag | gttgccgggt | gacgcacacc | gtggaaacgg | 1620 |
| atgaaggcac | gaacccagtg | gacataagcc | tgttcggttc | gtaagctgta | atgcaagtag | 1680 |
| cgtatgcgct | cacgcaactg | gtccagaacc | ttgaccgaac | gcagcggtgg | taacggcgca | 1740 |
| gtggcggttt | tcatggcttg | ttatgactgt | ttttttgggg | tacagtctat | gcctcgggca | 1800 |
| tccaagcagc | aagcgcgtta | cgccgtgggt | cgatgtttga | tgttatggag | cagcaacgat | 1860 |
| gttacgcagc | agggcagtcg | ccctaaaaca | aagttaaaca | ttatgaggga | agcggtgatc | 1920 |
| gccgaagtat | cgactcaact | atcagaggta | gttggcgtca | tcgagcgcca | tctcgaaccg | 1980 |
| acgttgctgg | ccgtacattt | gtacggctcc | gcagtggatg | gcggcctgaa | gccacacagt | 2040 |
| gatattgatt | tgctggttac | ggtgaccgta | aggcttgatg | aaacaacgcg | gcgagctttg | 2100 |
| atcaacgacc | ttttggaaac | ttcggcttcc | cctggagaga | gcgagattct | ccgcgctgta | 2160 |

```
gaagtcacca ttgttgtgca cgacgacatc attccgtggc gttatccagc taagcgcgaa    2220
ctgcaatttg gagaatggca gcgcaatgac attcttgctg gtatcttcga gccagccacg    2280
atcgacattg atctggctat cttgctgaca aaagcaagag aacatagcgt tgccttggta    2340
ggtccagcgg cggaggaact ctttgatccg gttcctgaac aggatctatt tgaggcgcta    2400
aatgaaacct taacgctatg gaactcgccg cccgactggg ctggcgatga gcgaaatgta    2460
gtgcttacgt tgtcccgcat ttggtacagc gcagtaaccg gcaaaatcgc gccgaaggat    2520
gtcgctgccg actgggcaat ggagcgcctg ccggcccagt atcagcccgt catacttgaa    2580
gctagacagg cttatcttgg acaagaagaa gatcgcttgg cctcgcgcgc agatcagttg    2640
gaagaatttg tccactacgt gaaaggcgag atcaccaagg tagtcggcaa ataacctcat    2700
tttcgccaga tatcgacgtc gacaccatcg aatggtgcaa aacctttcgc ggtatggcat    2760
gatagcgccc ggaagagagt caattcaggg tggtgaatgt gaaaccagta acgttatacg    2820
atgtcgcaga gtatgccggt gtctcttatc agaccgtttc ccgcgtggtg aaccaggcca    2880
gccacgtttc tgcgaaaacg cgggaaaaag tggaagcggc gatggcggag ctgaattaca    2940
ttcccaaccg cgtggcacaa caactggcgg gcaaacagtc gttgctgatt ggcgttgcca    3000
cctccagtct ggccctgcac gcgccgtcgc aaattgtcgc ggcgattaaa tctcgcgccg    3060
atcaactggg tgccagcgtg gtggtgtcga tggtagaacg aagcggcgtc gaagcctgta    3120
aagcggcggt gcacaatctt ctcgcgcaac gcgtcagtgg gctgatcatt aactatccgc    3180
tggatgacca ggatgccatt gctgtggaag ctgcctgcac taatgttccg gcgttatttc    3240
ttgatgtctc tgaccagaca cccatcaaca gtattatttt ctcccatgaa gacggtacgc    3300
gactgggcgt ggagcatctg gtcgcattgg gtcaccagca atcgcgctg ttagcgggcc    3360 cattaagttc tgtctcggcg cgtctgcgtc tggctggctg gcataaatat ctcactcgca    3420
atcaaattca gccgatagcg gaacgggaag gcgactggag tgccatgtcc ggttttcaac    3480
aaaccatgca aatgctgaat gagggcatcg ttcccactgc gatgctggtt gccaacgatc    3540
agatggcgct gggcgcaatg cgcgccatta ccgagtccgg gctgcgcgtt ggtgcggata    3600
tctcggtagt gggatacgac gataccgaag acagctcatg ttatatcccg ccgttaacca    3660
ccatcaaaca ggattttcgc ctgctggggc aaaccagcgt ggaccgcttg ctgcaactct    3720
ctcagggcca ggcggtgaag gcaatcagc tgttgcccgt ctcactggtg aaaagaaaaa    3780
ccaccctggc gcccaatacg caaaccgcct ctccccgcgc gttggccgat tcattaatgc    3840
agctggcacg acaggtttcc cgactggaaa gcgggcagtg agcgcaacgc aattaatgta    3900
agttagcgcg aattgatctg gtttgacagc ttatcatcga ctgcacggtg caccaatgct    3960
tctggcgtca ggcagccatc ggaagctgtg gtatggctgt gcaggtcgta aatcactgca    4020
taattcgtgt cgctcaaggc gcactcccgt tctggataat gttttttgcg ccgacatcat    4080
aacggttctg gcaaatattc tgaaatgagc tgttgacaat taatcatccg gctcgtataa    4140
tgtgtggaat tgtgagcgga taacaatttc agaattcaaa agatctaaag aggagaaata    4200
ctagatgacc gatgtgcgct ttcgcatcat cggcaccggc gcctacgtgc cgaacgcat    4260 cgtgagcaac gatgaagtgg gcgccccccgc cggcgtggat gatgattgga tcacccgcaa    4320
aaccggcatc cgccagcgcc gctgggccgc cgatgatcag gccaccagcg atctggccac    4380
cgccgccggc cgcgccgccc tgaaagccgc cggcatcacc cccgaacagc tgaccgtgat    4440
cgccgtggcc accagcaccc ccgatcgccc ccagccccc accgccgcct acgtgcagca    4500
```

-continued

```
ccacctgggc gccaccggca ccgccgcctt tgatgtgaac gccgtgtgca gcggcaccgt    4560
gtttgccctg agcagcgtgg ccggcaccct ggtgtaccgc ggcggctacg ccctggtgat    4620
cggcgccgat ctgtacagcc gcatcctgaa ccccgccgat cgcaaaaccg tggtgctgtt    4680
tggcgatggc gccggcgcca tggtgctggg ccccaccagc accggcaccg gcccatcgt     4740
gcgccgcgtg gccctgcaca cctttggcgg cctgaccgat ctgatccgcg tgcccgccgg    4800
cggcagccgc cagcccctgg ataccgatgg cctggatgcc ggcctgcagt actttgccat    4860
ggatggccgc gaagtgcgcc gctttgtgac cgaacacctg ccccagctga tcaaaggctt    4920
tctgcacgaa gccggcgtgg atgccgccga tatcagccac tttgtgcccc accaggccaa    4980
cggcgtgatg ctggatgaag tgtttggcga actgcacctg ccccgcgcca ccatgcaccg    5040
caccgtggaa acctacgcca acaccggcgc cgccagcatc cccatcacca tggatgccgc    5100
cgtgcgcgcc ggcagctttc gccccggcga actggtgctg ctggccggct ttggcggcgg    5160
catggccgcc agctttgccc tgatcgaatg gtagggatct aagaggagaa atactagatg    5220
aaaaccaaac tgatgacccc tccaggatgcc accggctttt tcgcgatgg catgaccatc    5280
atggtgggcg gctttatggg catcggcacc cccagccgcc tggtggaagc cctgctggaa    5340
agcggcgtgc gcgatctgac cctgatcgcc aacgataccg cctttgtgga taccggcatc    5400
ggccccctga tcgtgaacgg ccgcgtgcgc aaagtgatcg ccagccacat cggcaccaac    5460
cccgaaaccg gccgccgcat gatcagcggc gaaatggatg tggtgctggt gccccagggc    5520
accctgatcg aacagatccg ctgcggcggc gccggcctgg gcggctttct gaccccccacc    5580
ggcgtgggca ccgtggtgga agaaggcaaa cagaccctga ccctggatgg caaaacctgg    5640
ctgctggaac gccccctgcg cgccgatctg gccctgatcc gcgcccaccg ctgcgatacc    5700
ctgggcaacc tgacctacca gctgagcgcc cgcaacttta ccccctgat cgccctggcc    5760
gccgatatca ccctggtgga acccgatgaa ctggtggaaa ccggcgaact ccagcccgat    5820
cacatcgtga ccccggcgc cgtgatcgat cacatcatcg tgagccagga aagcaaatag    5880
ttaaagagga gaatactaga tggatgccaa acagcgcatc gcccgccgcg tggcccagga    5940
actgcgcgat ggcgatatcg tgaacctggg catcggcctg cccaccatgg tggccaacta    6000
cctgcccgaa ggcatccaca tcaccctcca gagcgaaaac ggctttctgg gcctgggccc    6060
cgtgaccacc gcccacccg atctggtgaa cgccggcggc cagccctgcg gcgtgctgcc    6120
cggcgccgcc atgtttgata cgccatgag ctttgccctg atccgcggcg ccacatcga     6180
tgcctgcgtg ctgggcggcc tccaggtgga tgaagaagcc aacctggcca actgggtggt    6240
gcccggcaaa atggtgcccg gcatgggcgg cgccatggat ctggtgaccg gcagccgcaa    6300
agtgatcatc gccatggaac actgcgccaa agatggcagc gccaaaatcc tgcgccgctg    6360
caccatgccc ctgaccgccc agcacgccgt gcacatgctg gtgaccgaac tggccgtgtt    6420
tcgctttatc gatggcaaaa tgtggctgac cgaaatcgcc gatggctgcg atctggccac    6480
cgtgcgcgcc aaaaccgaag cccgctttga agtggccgcc gatctgaaca cccagcgcgg    6540
cgatctgtag ggatctggat cttttaaagag gagaatacta gatgctgaaa gatgaagtga    6600
tcaaacagat cagcaccccc ctgaccagcc ccgccttttcc ccgcggcccc tacaaattc    6660
acaaccgcga atactttaac atcgtgtacc gcaccgatat ggatgccctg cgcaaagtgg    6720
tgcccgaacc cctggaaatc gatgaacccc tggtgcgctt tgaaatcatg gccatgcacg    6780
ataccagcgg cctgggctgc tacaccgaaa gcggccaggc catccccgtg agctgcaacg    6840
gcgtgaaagg cgattacctg cacatgatgt acctggataa cgaacccgcc atcgccgtgg    6900
```

```
gccgcgaact gagcgcctac cccaaaaaac tgggctaccc caaactgttt gtggatagcg      6960
ataccctggt gggcaccctg gattacggca aactgcgcgt ggccaccgcc accatgggct      7020
acaaacacaa agccctggat gccaacgaag ccaaagatca gatttgccgc cccaactaca      7080
tgctgaaaat catccccaac tacgatggca gcccccgcat ctgcgaactg atcaacgcca      7140
aaatcaccga tgtgaccgtg cacgaagcct ggaccggccc cacccgcctc cagctgtttg      7200
atcacgccat ggcccccctg aacgatctgc ccgtgaaaga atcgtgagc agcagccaca      7260 tcctggccga tatcatcctg ccccgcgccg aagtgatcta cgattacctg aaatagctcg      7320
agtaaggatc tccaggcatc aaataaaacg aaaggctcag tcgaaagact gggccttttcg     7380 ttttatctgt tgtttgtcgg tgaacgctct ctactagagt cacactggct caccttcggg      7440
tgggcctttc tgcgtttata cctagggcgt tcggctgcgg cgagcggtat cagctcactc      7500
aaaggcggta atacgtccct gctcgtcacg cttttcaggca ccgtgccaga tatcgacgtg    7560
gagtcgatca ctgtgattgg cgaaggggaa ggcagcgcta cccaaatcgc tagcttgctg     7620
gagaagctga acaaaccac gggcattgat ctggcgaaat ccctaccggg tcaatccgac      7680
tcgcccgctg cgaagtccta agagatagcg atgtgaccgc gatcgcttgt caagaatccc     7740
agtgatcccg aaccatagga aggcaagctc aatgcttgcc tcgtcttgag gactatctag    7800
atgtctgtgg aacgcacatt tattgccatc aagcccgatg gcgttcagcg gggtttggtc    7860
ggtacgatca tcggccgctt tgagcaaaaa ggcttcaaac tggtgggcct aaagcagctg    7920
aagcccagtc gcgagctggc cgaacagcac tatgctgtcc accgcgagcg ccccttcttc    7980
aatggcctcg tcgagttcat cacctctggg ccgatcgtgg cgatcgtctt ggaaggcgaa    8040
ggcgttgtgg cggctgctcg caagttgatc ggcgctacca atccgctgac ggcagaaccg    8100
ggcaccatcc gtggtgattt tggtgtcaat attggccgca acatcatcca tggctcggat    8160
gcaatcgaaa cagcacaaca ggaaattgct ctctggttta gcccagcaga gctaagtgat    8220 tggacccca cgattcaacc ctggctgtac gaataaggtc tgcattcctt cagagagaca      8280
ttgccatgcc c                                                         8291
```

<210> SEQ ID NO 9
<211> LENGTH: 8282
<212> TYPE: DNA
<213> ORGANISM: Artificial Sequence
<220> FEATURE:
<223> OTHER INFORMATION: pSe1Bb1s-nphT7-ctfAB-adc vector

<400> SEQUENCE: 9

```
gataatctca tgaccaaaat cccttaacgt gagttttcgt tccactgagc gtcagacccc       60
gtagaaaaga tcaaaggatc ttcttgagat cctttttttc tgcgcgtaat ctgctgcttg      120
caaacaaaaa aaccaccgct accagcggtg gtttgtttgc cggatcaaga gctaccaact      180
ctttttccga aggtaactgg cttcagcaga gcgcagatac caaatactgt tcttctagtg      240
tagccgtagt taggccacca cttcaagaac tctgtagcac cgcctacata cctcgctctg      300
ctaatcctgt taccagtggc tgctgccagt ggcgataagt cgtgtcttac cgggttggac      360
tcaagacgat agttaccgga taaggcgcag cggtcgggct gaacggggg ttcgtgcaca      420 cagcccagct tggagcgaac gacctacacc gaactgagat acctacagcg tgagctatga     480
gaaagcgcca cgcttcccga agggagaaag gcggacaggt atccggtaag cggcagggtc     540
ggaacaggag agcgcacgag ggagcttcca gggggaaacg cctggtatct ttatagtcct     600
```

```
gtcgggtttc gccacctctg acttgagcgt cgattttgt gatgctcgtc agggggggcgg    660 agcctatgga aaaacgccag caacgcggcc tttttacggt tcctggcctt ttgctggcct    720
tttgctcaca tgtgtgctgg gccccaatgc cttctccaag ggcggcattc ccctgactgt    780
tgaaggcgtt gccaatatca agattgctgg ggaagaaccg accatccaca acgcgatcga    840
gcggctgctt ggcaaaaacc gtaaggaaat cgagcaaatt gccaaggaga ccctcgaagg    900
caacttgcgt ggtgttttag ccagcctcac gccggagcag atcaacgagg acaaaattgc    960
ctttgccaaa agtctgctgg aagaggcgga ggatgacctt gagcagctgg gtctagtcct   1020
cgatacgctg caagtccaga acatttccga tgaggtcggt tatctctcgg ctagtggacg   1080
caagcagcgg gctgatctgc agcgagatgc ccgaattgct gaagccgatg cccaggctgc   1140
ctctgcgatc caaacggccg aaaatgacaa gatcacggcc ctgcgtcgga tcgatcgcga   1200
tgtagcgatc gcccaagccg aggccgagcg ccggattcag gatgcgttga cgcggcgcga   1260
agcggtggtg gccgaagctg aagcggacat tgctaccgaa gtcgctcgta gccaagcaga   1320
actccctgtg cagcaggagc ggatcaaaca ggtgcagcag caacttcaag ccgatgtgat   1380
cgccccagct gaggcagctt gtaaacgggc gatcgcggaa gcgcggggggg ccgccgcccg   1440 tatcgtcgaa gatggaaaag ctcaagcgga agggacccaa cggctggcgg aggcttggca   1500
gaccgctggt gctaatgccc gcgacatctt cctgctccag aagtctagac cagccaggac   1560
agaaatgcct cgacttcgct gctacccaag gttgccgggt gacgcacacc gtggaaacgg   1620
atgaaggcac gaacccagtg gacataagcc tgttcggttc gtaagctgta atgcaagtag   1680
cgtatgcgct cacgcaactg gtccagaacc ttgaccgaac gcagcggtgg taacggcgca   1740
gtggcggttt tcatggcttg ttatgactgt tttttgggg tacagtctat gcctcgggca   1800
tccaagcagc aagcgcgtta cgccgtgggt cgatgtttga tgttatggag cagcaacgat   1860
gttacgcagc agggcagtcg ccctaaaaca aagttaaaca ttatgaggga agcggtgatc   1920
gccgaagtat cgactcaact atcagaggta gttggcgtca tcgagcgcca tctcgaaccg   1980
acgttgctgg ccgtacattt gtacggctcc gcagtggatg gcggcctgaa gccacacagt   2040
gatattgatt tgctggttac ggtgaccgta aggcttgatg aaacaacgcg gcgagctttg   2100
atcaacgacc ttttggaaac ttcggcttcc cctggagaga gcgagattct ccgcgctgta   2160
gaagtcacca ttgttgtgca cgacgacatc attccgtggc gttatccagc taagcgcgaa   2220
ctgcaatttg gagaatggca gcgcaatgac attcttgctg gtatcttcga gccagccacg   2280
atcgacattg atctggctat cttgctgaca aaagcaagag aacatagcgt tgccttggta   2340
ggtccagcgg cggaggaact cttttgatccg gttcctgaac aggatctatt tgaggcgcta   2400
aatgaaacct taacgctatg gaactcgccg cccgactggg ctggcgatga gcgaaatgta   2460
gtgcttacgt tgtcccgcat ttggtacagc gcagtaaccg gcaaaatcgc gccgaaggat   2520
gtcgctgccg actgggcaat ggagcgcctg ccggcccagt atcagcccgt catacttgaa   2580
gctagacagg cttatcttgg acaagaagaa gatcgcttgg cctcgcgcgc agatcagttg   2640
gaagaatttg tccactacgt gaaaggcgag atcaccaagg tagtcggcaa ataacctcat   2700
tttcgccaga tatcgacgtc gacaccatcg aatggtgcaa aaccttttcgc ggtatggcat   2760 gatagcgccc ggaagagagt caattcaggg tggtgaatgt gaaaccagta acgttatacg   2820
atgtcgcaga gtatgccggt gtctcttatc agaccgtttc ccgcgtggtg aaccaggcca   2880
gccacgtttc tgcgaaaacg cgggaaaaag tggaagcggc gatggcggag ctgaattaca   2940
ttcccaaccg cgtggcacaa caactggcgg gcaaacagtc gttgctgatt ggcgttgcca   3000
```

```
cctccagtct ggccctgcac gcgccgtcgc aaattgtcgc ggcgattaaa tctcgcgccg   3060
atcaactggg tgccagcgtg gtggtgtcga tggtagaacg aagcggcgtc gaagcctgta   3120
aagcggcggt gcacaatctt ctcgcgcaac gcgtcagtgg gctgatcatt aactatccgc   3180
tggatgacca ggatgccatt gctgtggaag ctgcctgcac taatgttccg gcgttatttc   3240
ttgatgtctc tgaccagaca cccatcaaca gtattatttt ctcccatgaa gacggtacgc   3300
gactgggcgt ggagcatctg gtcgcattgg gtcaccagca aatcgcgctg ttagcgggcc   3360
cattaagttc tgtctcggcg cgtctgcgtc tggctggctg gcataaatat ctcactcgca   3420
atcaaattca gccgatagcg gaacgggaag gcgactggag tgccatgtcc ggttttcaac   3480
aaaccatgca aatgctgaat gagggcatcg ttcccactgc gatgctggtt gccaacgatc   3540
agatggcgct gggcgcaatg cgcgccatta ccgagtccgg gctgcgcgtt ggtgcggata   3600
tctcggtagt gggatacgac gataccgaag acagctcatg ttatatcccg ccgttaacca   3660
ccatcaaaca ggattttcgc ctgctggggc aaaccagcgt ggaccgcttg ctgcaactct   3720
ctcagggcca ggcggtgaag ggcaatcagc tgttgcccgt ctcactggtg aaaagaaaaa   3780
ccaccctggc gcccaatacg caaaccgcct ctccccgcgc gttggccgat tcattaatgc   3840
agctggcacg acaggtttcc cgactggaaa gcgggcagtg agcgcaacgc aattaatgta   3900
agttagcgcg aattgatctg gtttgacagc ttatcatcga ctgcacggtg caccaatgct   3960
tctggcgtca ggcagccatc ggaagctgtg gtatggctgt gcaggtcgta aatcactgca   4020
taattcgtgt cgctcaaggc gcactcccgt tctggataat gttttttgcg ccgacatcat   4080
aacggttctg gcaaatattc tgaaatgagc tgttgacaat taatcatccg gctcgtataa   4140
tgtgtggaat tgtgagcgga taacaatttc agaattcaaa agatctaaag aggagaaata   4200
ctagatgacc gatgtgcgct ttcgcatcat cggcaccggc gcctacgtgc ccgaacgcat   4260
cgtgagcaac gatgaagtgg cgcccccgc cggcgtggat gatgattgga tcacccgcaa   4320
aaccggcatc cgccagcgcc gctgggccgc cgatgatcag gccaccagcg atctggccac   4380
cgccgccggc cgcgccgccc tgaaagccgc cggcatcacc cccgaacagc tgaccgtgat   4440
cgccgtggcc accagcaccc ccgatcgccc ccagcccccc accgccgcct acgtgcagca   4500
ccacctgggc gccaccggca ccgccgcctt tgatgtgaac gccgtgtgca gcggcaccgt   4560
gtttgccctg agcagcgtgg ccggcaccct ggtgtaccgc ggcggctacg ccctggtgat   4620
cggcgccgat ctgtacagcc gcatcctgaa ccccgccgat cgcaaaaccg tggtgctgtt   4680
tggcgatggc gccggcgcca tggtgctggg ccccaccagc accggcaccg gccccatcgt   4740
gcgccgcgtg gccctgcaca cctttggcgg cctgaccgat ctgatccgcg tgcccgccgg   4800
cggcagccgc cagcccctgg ataccgatgg cctggatgcc ggcctgcagt actttgccat   4860
ggatggccgc gaagtgcgcc gctttgtgac cgaacacctg ccccagctga tcaaaggctt   4920
tctgcacgaa gccggcgtgg atgccgccga tatcagccac tttgtgcccc accaggccaa   4980
cggcgtgatg ctggatgaag tgtttggcga actgcacctg ccccgcgcca ccatgcaccg   5040
caccgtggaa acctacggca cacccggcgc cgccagcatc cccatcacca tggatgccgc   5100
cgtgcgcgcc ggcagctttc gccccggcga actggtgctg ctggccggct ttggcggcgg   5160
catggccgcc agctttgccc tgatcgaatg gtagggatct aagaggagaa atactagatg   5220
aacagcaaaa tcatccgctt tgaaaacctg cgcagctttt ttaaagatgg catgaccatc   5280
atgatcggcg gctttctgaa ctgcggcacc cccaccaaac tgatcgattt tctggtgaac   5340
```

```
ctgaacatca aaaacctgac catcatcagc aacgatacct gctaccccaa caccggcatc      5400
ggcaaactga tcagcaacaa ccaggtgaaa aaactgatcg ccagctacat cggcagcaac      5460
cccgataccg gcaaaaaact gtttaacaac gaactggaag tggaactgag cccccagggc      5520
accctggtgg aacgcatccg cgccggcggc agcggcctgg gcggcgtgct gaccaaaacc      5580
ggcctgggca ccctgatcga aaaggcaaa aaaaaatca gcatcaacgg caccgaatac       5640
ctgctggaac tgcccctgac cgccgatatc gccctgatca aaggcagcat cgtggatgaa      5700
gccggcaaca ccttttacaa aggcaccacc aaaaacttta acccctacat ggccatggcc      5760
gccaaaaccg tgatcgtgga agccgaaaac ctggtgagct gcgaaaaact ggaaaaagaa      5820
aaagccatga cccccggcgt gctgatcaac tacatcgtga agaacccgc ctaaaatgat       5880 caacgataaa aacctggcca agaaatcat cgccaaacgc gtggcccgcg aactgaaaaa       5940
cggccagctg gtgaacctgg gcgtgggcct gcccaccatg gtggccgatt acatccccaa      6000
aaactttaaa atcaccttc agagcgaaaa cggcatcgtg gcatgggcg ccagcccca        6060 aatcaacgaa gccgataaag atgtggtgaa cgccggcggc gattacacca ccgtgctgcc      6120
cgatggcacc ttttttgata gcagcgtgag ctttagcctg atccgcggcg ccacgtgga       6180 tgtgaccgtg ctgggcgccc tccaggtgga tgaaaaaggc aacatcgcca actggatcgt      6240
gcccggcaaa atgctgagcg gcatgggcgg cgccatggat ctggtgaacg gcgccaaaaa      6300
agtgatcatc gccatgcgcc acaccaacaa aggccagccc aaaatcctga aaaatgcac      6360 cctgccctg accgccaaaa gccaggccaa cctgatcgtg accgaactgg gcgtgatcga      6420
agtgatcaac gatggcctgc tgctgaccga aatcaacaaa acaccacca tcgatgaaat       6480 ccgcagcctg accgccgccg atctgctgat cagcaacgaa ctgcgcccca tggccgtgta      6540
gggatctgga tctttaaaga ggagaatact agatgctgaa agatgaagtg atcaaacaga      6600
tcagcacccc cctgaccagc cccgccttc cccgcggccc ctacaaattt cacaaccgcg       6660
aatactttaa catcgtgtac cgcaccgata tggatgccct gcgcaaagtg gtgccccgaac     6720 ccctggaaat cgatgaaccc ctggtgcgct ttgaaatcat ggccatgcac gataccagcg      6780
gcctgggctg ctacaccgaa agcggccagg ccatccccgt gagctgcaac ggcgtgaaag      6840
gcgattacct gcacatgatg tacctggata acgaacccgc catcgccgtg ggccgcgaac      6900
tgagcgccta ccccaaaaaa ctgggctacc ccaaactgtt tgtggatagc gatacctgg      6960 tgggcaccct ggattacggc aaactgcgcg tggccaccgc caccatgggc tacaaacaca      7020
aagccctgga tgccaacgaa gccaaagatc agatttgccg ccccaactac atgctgaaaa      7080
tcatccccaa ctacgatggc agcccccgca tctgcgaact gatcaacgcc aaaatcaccg      7140
atgtgaccgt gcacgaagcc tggaccggcc ccacccgcct ccagctgttt gatcacgcca      7200
tggcccccct gaacgatctg cccgtgaaag aaatcgtgag cagcagccac atcctggccg      7260
atatcatcct gccccgcgcc gaagtgatct acgattacct gaaatagctc gagtaaggat      7320
ctccaggcat caaataaaac gaaaggctca gtcgaaagac tgggcctttc gttttatctg      7380
ttgtttgtcg gtgaacgctc tctactagag tcacactggc tcaccttcgg gtgggccttt      7440
ctgcgtttat acctagggcg ttcggctgcg cgagcggta tcagctcact caaaggcggt       7500
aatacgtccc tgctcgtcac gctttcaggc accgtgccag atatcgacgt ggagtcgatc      7560
actgtgattg gcgaagggga aggcagcgct acccaaatcg ctagcttgct ggagaagctg      7620
aaacaaacca cggcattga tctggcgaaa tccctaccgg gtcaatccga ctcgcccgct       7680
gcgaagtcct aagagatagc gatgtgaccg cgatcgcttg tcaagaatcc cagtgatccc      7740
```

```
gaaccatagg aaggcaagct caatgcttgc ctcgtcttga ggactatcta gatgtctgtg    7800
gaacgcacat ttattgccat caagcccgat ggcgttcagc ggggtttggt cggtacgatc    7860
atcggccgct ttgagcaaaa aggcttcaaa ctggtgggcc taaagcagct gaagcccagt    7920
cgcgagctgg ccgaacagca ctatgctgtc caccgcgagc gccccttctt caatggcctc    7980
gtcgagttca tcacctctgg gccgatcgtg gcgatcgtct tggaaggcga aggcgttgtg    8040
gcggctgctc gcaagttgat cggcgctacc aatccgctga cggcagaacc gggcaccatc    8100
cgtggtgatt ttggtgtcaa tattggccgc aacatcatcc atggctcgga tgcaatcgaa    8160
acagcacaac aggaaattgc tctctggttt agcccagcag agctaagtga ttggacccc    8220 acgattcaac cctggctgta cgaataaggt ctgcattcct tcagagagac attgccatgc    8280
cc                                                                  8282

<210> SEQ ID NO 10
<211> LENGTH: 19
<212> TYPE: DNA
<213> ORGANISM: Artificial Sequence
<220> FEATURE:
<223> OTHER INFORMATION: PRIMER(FORWARD)

<400> SEQUENCE: 10
ctgattgttc taggcgctg                                                          19

<210> SEQ ID NO 11
<211> LENGTH: 20
<212> TYPE: DNA
<213> ORGANISM: Artificial Sequence
<220> FEATURE:
<223> OTHER INFORMATION: PRIMER(REVERSE)

<400> SEQUENCE: 11
tttggcaatc tgaagacccg                                                         20
```

TRANSFORMED *SYNECHOCOCCUS ELONGATUS* HAVING CAPABILITY OF PRODUCING ACETONE FROM CARBON DIOXIDE

DESCRIPTION ABOUT NATIONAL SUPPORT RESEARCH AND DEVELOPMENT

This work is supported by business of the National Research Foundation of Korea grant-funded by the Korean Government (Ministry of Science, ICT and Future Planning) under the supervision of Korea Institute of Science and Technology, and the subject number thereof is 2015U00023 (2N40353). Also, This work is supported by the support of KCRC CCS2020 business of Korea Ministry of Science, ICT and Future Planning under the supervision of Korea Institute of Science and Technology, and the subject name thereof is Development of original technology of using recombinant cyanobacteria for continuous direct production of biodiesel (2N38970) (Subject Identification No. 2014M1A8A1049277).

FIELD OF THE INVENTION

Disclosed herein are a transformed *Synechococcus elongatus* strain having improved capability of producing acetone and a method for producing acetone and a method for removing carbon dioxide using the same.

CROSS-REFERENCE TO RELATED APPLICATION

This application claims priority to Korean Patent Application No. 10-2015-0030616, filed on Mar. 4, 2015, and all the benefits accruing therefrom under 35 U.S.C. §119, the contents of which in its entirety are herein incorporated by reference.

BACKGROUND OF THE INVENTION

Recently, concerns about depletion of fossil fuel resources and environmental pollution are increasing globally and the energy problem is becoming an important social issue due to change in oil prices, effectuation of the UN Framework Convention on Climate Change, etc. In particular, with the prediction of depletion of petroleum which is used in all industrial fields, the energy problem is becoming an important threat to national security and survival. For this reason, interests in biofuels that can replace the fossil fuel are increasing consistently.

A biofuel refers to a fuel obtained from biomass, including not only living organisms but also byproducts of metabolic activities such as excrement of animals. It is a renewable source of energy, unlike the fossil fuel. Recently, also in Korea, development of biofuels using microorganisms is being studied actively with the advance in biotechnology and attempts are made to extend its scope to bioethanol, biobutanol, biodiesel, etc.

SUMMARY

In an aspect, the present disclosure is directed to providing a *Synechococcus elongatus* strain having improved capability of producing acetone.

In another aspect, the present disclosure is directed to producing acetone on a large scale using a *Synechococcus elongatus* strain.

In another aspect, the present disclosure is directed to removing a carbon dioxide using a *Synechococcus elongatus* strain.

In an aspect, the present disclosure relates to a *Synechococcus elongatus* strain having an acetone selectivity, defined as the molar ratio of acetone in the total product produced by the strain, of 0.8 or greater under a condition of 30° C. and 5% carbon dioxide.

In another aspect, the present disclosure relates to a method for producing acetone, including a step of culturing a *Synechococcus elongatus* strain.

In another aspect, the present disclosure relates to a method for removing carbon dioxide, including a step of culturing a *Synechococcus elongatus* strain.

In an aspect, the transformed *Synechococcus elongatus* strain of the present disclosure can produce acetone with high selectivity using carbon dioxide as a carbon source. The present disclosure is economical because the *Synechococcus elongatus* strain can economically produce high value-added acetone using carbon dioxide existing in the atmosphere as a carbon source without requiring an additional catalytic reaction. Also, the present disclosure is environment-friendly because carbon dioxide in the atmosphere can be removed or reduced using the microorganism.

BRIEF DESCRIPTION OF THE DRAWINGS

FIG. 6 shows the sequence of an atoB-derived gene (SEQ ID NO.: 1).

FIG. 7 shows the sequence of an nphT7-derived gene (SEQ ID NO.: 2).

FIG. 8 shows the sequence of an atoDA-derived gene (SEQ ID NO.: 3).

FIG. 9 shows the sequence of a ctfAB-derived gene (SEQ ID NO.: 4).

FIG. 10 shows the sequence of an adc-derived gene (SEQ ID NO.: 5).

FIGS. 11A to 11D show the sequence of a pSe1Bb1s-atoB-atoDA-adc vector, in sequence (SEQ ID NO.: 6).

FIGS. 12A to 12D show the sequence of a pSe1Bb1s-atoB-ctfAB-adc vector, in sequence (SEQ ID NO.: 7).

FIGS. 13A to 13D show the sequence of a pSe1Bb1s-nphT7-atoDA-adc vector(SEQ ID NO.: 8), in sequence.

FIGS. 14A to 14D show the sequence of a pSe1Bb1s-nphT7-ctfAB-adc vector (SEQ ID NO.: 9), in sequence.

FIG. 15 shows the sequence of a forward primer(SEQ ID NO.: 10) used in polymerase chain reaction (PCR) for identifying the transformation of the strain.

FIG. 16 shows the sequence of a reverse primer(SEQ ID NO.: 11) used in polymerase chain reaction (PCR) for identifying the transformation of the strain.

DETAILED DESCRIPTION

Figure 1:
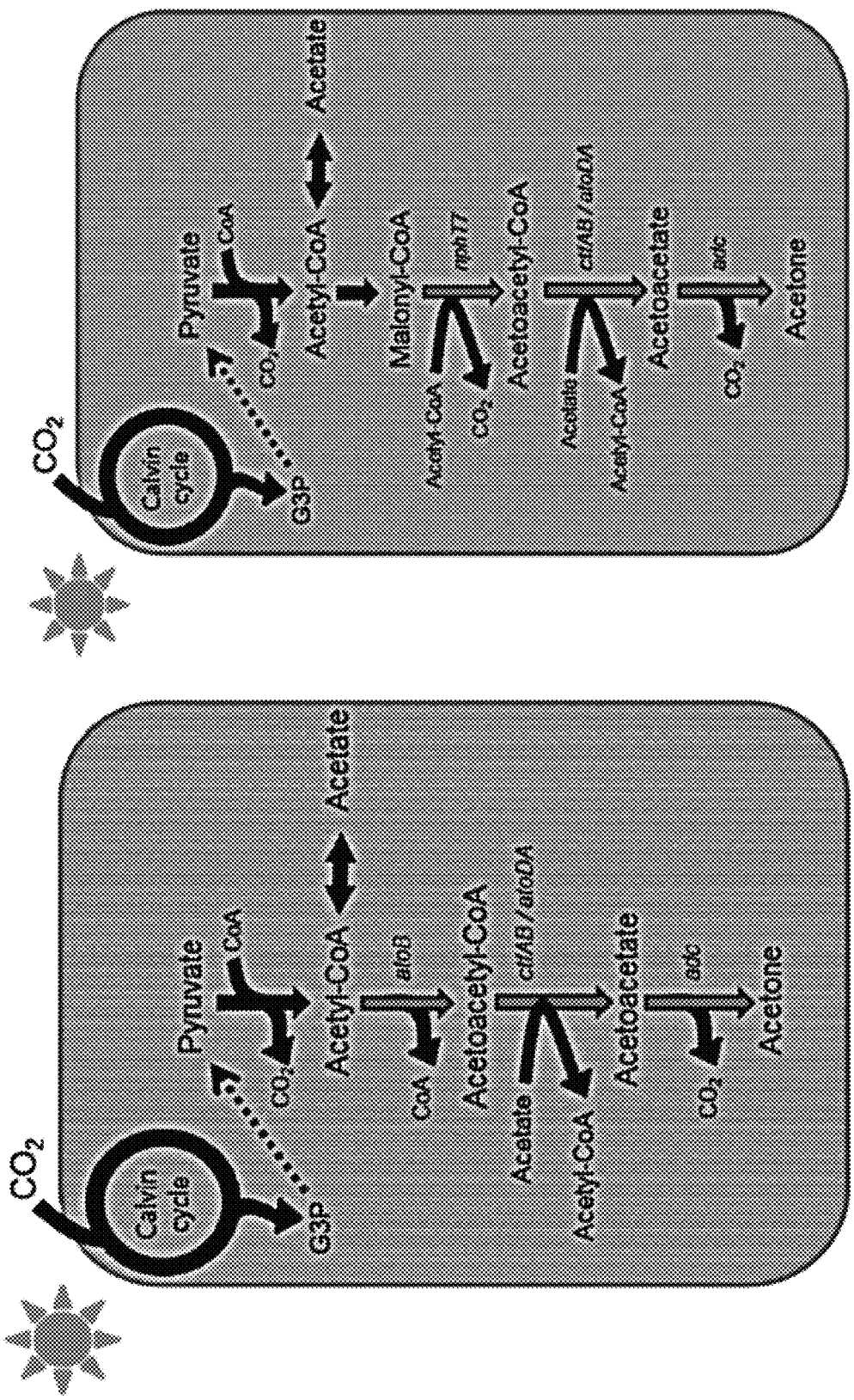
FIG. 1 shows the acetone metabolic pathway of a transformed *Synechococcus elongatus* strain.

Hereinafter, the present disclosure is described in detail.

*Synechococcus elongatus* is a species of cyanobacteria. The prokaryotic cyanobacteria are useful in altering metabolic pathways or artificially regulating metabolites because genetic modification is easy. The inventors of the present disclosure have completed the present disclosure based on this characteristic of cyanobacteria using the techniques of synthetic biology and metabolic engineering.

In an aspect, the present disclosure relates to a *Synechococcus elongatus* strain having an acetone selectivity of 0.8 or greater under a condition of 30° C. and 5% carbon dioxide.

In the present disclosure, the acetone selectivity is defined as the molar ratio of acetone in the total product produced by the *Synechococcus elongatus* strain.

Specifically, the acetone selectivity may be 0.7 or greater, 0.75 or greater, 0.8 or greater, 0.81 or greater, 0.83 or greater, 0.85 or greater, 0.87 or greater, 0.89 or greater, 0.91 or greater, 0.93 or greater, 0.95 or greater, 0.97 or greater, 0.98 or greater, 0.99 or greater or 1. And, the temperature may be, for example, 10-50° C., 10-45° C., 10-40° C., 10-35° C., 15-50° C., 20-45° C., 25-40° C. or 30-40° C. And, the carbon dioxide concentration may be 1-10%. But, without being limited thereto, the concentration may be 0.01% or higher, 0.05% or higher, 0.07% or higher, 0.09% or higher, 1% or higher, 2% or higher, 4% or higher, 5% or higher, 6% or higher, 8% or higher, 9% or higher, 11% or higher, 13% or higher, 15% or higher, 17% or higher, 20% or higher, 25% or higher, 30% or higher, 40% or higher, 50% or higher, 60% or higher, 70% or higher, 80% or higher or 90% or higher, and may be 91% or lower, 85% or lower, 80% or lower, 76% or lower, 71% or lower, 66% or lower, 61% or lower, 56% or lower, 51% or lower, 46% or lower, 41% or lower, 36% or lower, 31% or lower, 25% or lower, 19% or lower, 15% or lower, 13% or lower, 12% or lower, 9% or lower, 7% or lower, 5% or lower, 4% or lower, 3% or lower, 2% or lower or 1% or lower.

In this aspect, the strain may contain: one or more selected from a group consisting of an acetyl-CoA transferase gene and an acetyl-CoA synthase gene; an acetoacetyl-CoA transferase gene; and an acetoacetate decarboxylase gene.

In the present disclosure, the acetyl-CoA transferase gene refers to a gene that encodes acetyl-CoA transferase. For example, it may be one derived from an atoB gene of an *E. coli* K-12 MG1655 strain.

In the present disclosure, the acetyl-CoA synthase gene refers to a gene that encodes acetyl-CoA synthase. For example, it may be one derived from an nphT7 gene of a *Streptomyces* sp. strain.

And, in the present disclosure, the acetoacetyl-CoA transferase gene refers to a gene that encodes acetoacetyl-CoA transferase. For example, it may be one derived from an atoDA gene of an *E. coli* K-12 MG1655 strain. Or, it may be one derived from a ctfAB gene of a *Clostridium acetobutylicum* strain.

Also, in the present disclosure, the acetoacetate decarboxylase gene refers to a gene that encodes the enzyme acetoacetate decarboxylase. For example, it may be one derived from an adc gene of a *Clostridium acetobutylicum* strain.

In the *Synechococcus elongatus* strain according to an aspect of the present disclosure, the acetyl-CoA transferase gene may contain a sequence of SEQ ID NO 1, the acetyl-CoA synthase gene may contain a sequence of SEQ ID NO 2, the acetoacetyl-CoA transferase gene may contain a sequence of SEQ ID NO 3 or SEQ ID NO 4, and the acetoacetate decarboxylase gene may contain a sequence of SEQ ID NO 5.

In this aspect, in the present disclosure, the sequence of SEQ ID NO 1 contains a sequence derived from an atoB gene, which encodes the acetyl-CoA transferase gene, and the sequence of SEQ ID NO 2 contains a sequence derived from an nphT7 gene, which encodes the acetyl-CoA synthase gene. And, the sequence of SEQ ID NO 3 contains a sequence derived from an atoDA gene, which encodes the acetoacetyl-CoA transferase gene, and the sequence of SEQ ID NO 4 contains a sequence derived from a ctfAB gene, which encodes the acetoacetyl-CoA transferase gene. And, the sequence of SEQ ID NO 5 contains a sequence derived from an adc gene, which encodes the acetoacetate decarboxylase gene.

In this aspect, the *Synechococcus elongatus* strain may be one transformed with a vector containing: a gene containing a sequence derived from an atoB gene or an nphT7 gene; a gene containing a sequence derived from an atoDA gene or a cftAB gene; and a gene containing a sequence derived from an adc gene.

The genes in all the vectors disclosed in the present disclosure are linked operably. The expression operable means that a target gene can be expressed normally.

Also, the transformed *Synechococcus elongatus* strain may be *Synechococcus elongatus* PCC7942 (ATCC® 33912™) transformed with the vector.

In this aspect, the vector may further contain: a pUC replication origin as a replication origin; neutral sites located upstream and downstream of the replication origin; a spectinomycin resistance gene as a selection marker; a repressor selected from a group consisting of a lac I repressor, a tetR repressor and an AraC repressor; a promoter selected from a group consisting of a trc promoter, a tetA promoter or a modified tetA promoter, a BAD promoter and a cbbL promoter; and a BglII site, a BamHI site, an EcoRI site and an XhoI site as restriction enzyme sites.

The neutral site may be one derived from *Synechococcus elongatus* PCC 7942. For example, the neutral site may include NSIa and NSIb. The vector may be inserted into the genome of *Synechococcus elongatus* PCC 7942 through the neutral sites.

In this aspect, the vector may contain a target gene. For example, the target gene may be a gene containing a sequence derived from an atoB gene (hereinafter, an atoB-derived gene), a gene containing a sequence derived from an nphT7 gene (hereinafter, an nphT7-derived gene), a gene containing a sequence derived from an atoDA gene (hereinafter, an atoDA-derived gene), a gene containing a sequence derived from a cftAB gene (hereinafter, a cftAB-derived gene) or a gene containing a sequence derived from an adc gene (hereinafter, an adc-derived gene). These genes may be derived from different vectors. The different vectors may have a BglII site and a BamHI site on both sides of the target gene, and two target genes may be contained in one vector through complementary binding between the BglII site of one vector and the BamHI site of another vector upon treatment with a restriction enzyme. For example, a vector containing an atoB-derived gene (hereinafter, a pSe1Bb1s-atoB vector) or a vector containing an nphT7-derived gene (hereinafter, a pSe1Bb1s-nphT7 vector) may be prepared by removing the GFP portion of a SyneBrick vector pSe1Bb1s-GFP using EcoRI-BamHI restriction enzymes and then inserting the DNA sequence of an atoB-derived gene or an nphT7-derived gene. After treating each vector with BamHI-XhoI restriction enzymes, a vector containing 'an atoB-derived gene and an atoDA-derived gene' (hereinafter, a pSe1Bb1s-atoB-atoDA vector), a vector containing 'an atoB-derived gene and a ctfAB-derived gene' (hereinafter, a pSe1Bb1s-atoB-ctfAB vector), a vector containing 'an nphT7-derived gene and an atoDA-derived gene' (hereinafter, a pSe1Bb1s-nphT7-atoDA vector) and a vector containing 'an nphT7-derived gene and a ctfAB-derived gene' (hereinafter, a pSe1Bb1s-nphT7-ctfAB vector) may be prepared by inserting the DNA sequence of an atoDA-derived gene or a ctfAB-derived gene treated with BglII-XhoI restriction enzymes. Then, by treating each vector with BamHI-XhoI restriction enzymes and inserting the DNA sequence of an adc-derived gene treated with BglII-XhoI restriction enzymes, a vector containing 'an atoB-derived gene, an atoDA-derived gene and an adc-derived gene' (hereinafter, a pSe1Bb1s-atoB-atoDA-adc vector), a vector containing 'an atoB-derived gene, a ctfAB-derived gene and an adc-derived gene' (hereinafter, a pSe1Bb1s-atoB-ctfAB-adc vector), a vector containing 'an nphT7-derived gene, an atoDA-derived gene and an adc-derived gene' (hereinafter, a pSe1Bb1s-nphT7-atoDA-adc vector) and a vector containing 'an nphT7-derived gene, a ctfAB-derived gene and an adc-derived gene' (hereinafter, a pSe1Bb1s-nphT7-ctfAB-adc vector) may be obtained.

In this aspect, the BglII site and the BamHI site may be located on both sides of the target gene. In another aspect, the order of the target gene and the restriction enzyme sites may be: EcoRI site->BglII site->target gene->BamHI site->XhoII site.

In the *Synechococcus elongatus* strain according to an aspect of the present disclosure, the vector may contain a sequence from SEQ ID NOS 6-9. Specifically, SEQ ID NO 6 is the sequence of a vector containing an atoB-derived gene, an atoDA-derived gene and an adc-derived gene, SEQ ID NO 7 is the sequence of a vector containing an atoB-derived gene, a ctfAB-derived gene and an adc-derived gene, SEQ ID NO 8 is the sequence of a vector containing an nphT7-derived gene, an atoDA-derived gene and an adc-derived gene, and SEQ ID NO 9 is the sequence of a vector containing an nphT7-derived gene, a ctfAB-derived gene and an adc-derived gene.

The *Synechococcus elongatus* strain according to an aspect of the present disclosure may be a KCTC12758BP strain, a KCTC12759BP strain, a KCTC 12760BP strain or a KCTC12761BP strain. Specifically, the KCTC12758BP strain is one transformed with the vector of SEQ ID NO 6, the KCTC12759BP strain is one transformed with the vector of SEQ ID NO 7, the KCTC 12760BP strain is one transformed with the vector of SEQ ID NO 8, and the KCTC12761BP strain is one transformed with the vector of SEQ ID NO 9.

The strain may absorb and fix carbon dioxide.

In another aspect, the present disclosure relates to a method for producing acetone, including a step of culturing a *Synechococcus elongatus* strain.

In this aspect, the method for producing acetone may further include a step of supplying carbon dioxide to the strain and may further include a step of supplying potassium acetate. The transformed *Synechococcus elongatus* strain of the present disclosure may produce a larger amount of acetone when it is further supplied with potassium acetate in addition to carbon dioxide. The potassium acetate may be supplied with a concentration of 1-30 mM, although not being limited thereto. Specifically, the concentration may be 0.5-40 mM, 1-30 mM, 3-25 mM, 5-20 mM, 8-15 mM or 9-13 mM.

In another aspect, the present disclosure relates to a method for removing carbon dioxide, including a step of culturing a *Synechococcus elongatus* strain. Because the strain uses carbon dioxide as a carbon source, it may be useful in removing or reducing carbon dioxide in the atmosphere.

Hereinafter, the present disclosure will be described in detail through examples. However, the following examples are for illustrative purposes only and it will be apparent to those of ordinary skill in the art that the scope of the present disclosure is not limited by the examples.

EXAMPLE 1

Establishment of Strategy for Producing Acetone

A metabolic pathway as shown in FIG. 1 was designed to prepare a *Synechococcus elongatus* strain having excellent capability of producing acetone.

EXAMPLE 2

Preparation of Vector

At first, pBbE1c-RFP (Lee T S, Krupa R A, Zhang F, Hajimorad M, Holtz W J, Prasad N, Lee S K, Keasling J D (2011 b) BglBrick vectors and datasheets: a synthetic biology platform for gene expression. *J Biol Eng* 5:12) and Invitrogen's pSyn_1 were used. Specifically, the lacI, ptrc and RFP portions of pBbE1c-RFP were subjected to PCR and the spectinomycin resistance gene, NSIa, NS1b and pUC replication origin of pSyn_1 were subjected to PCR. Then, a new vector was completed by joining the two PCR products through the OPEC cloning method (Quan J, Tian J (2009) Circular Polymerase Extension Cloning of Complex Gene Libraries and Pathways. *PLoS ONE* 4 (7): e6441. doi:10.1371/journal.pone.0006441) (CPEC Ref. j5.jbei.org/j5manual/pages/22.html). In order to replace the RFP portion of the vector with GFP, RFP was removed using EcoRI/XhoI restriction enzymes and the GFP portion of another BglBrick vector pBbB5k-GFP (Lee T S, Krupa R A, Zhang F, Hajimorad M, Holtz W J, Prasad N, Lee S K, Keasling J D (2011b) BglBrick vectors and datasheets: a synthetic biology platform for gene expression. *J Biol Eng* 5:12) was inserted using EcoRI/XhoI restriction enzymes and a ligase. After transforming the vector into *E. coli* HIT-DH5a (Cat# RH617-J80, RBC Bioscience), the vector was extracted by mini-prep. Because the assembled vector, prepared through PCR, might have been mutated, the entire sequence was investigated through plasmid sequencing. The resulting vector was named as pSe1Bb1s-GFP. Then, after removing the GFP portion using EcoRI-BamHI restriction enzymes, the DNA sequence of an atoB-derived gene or an nphT7-derived gene was inserted. Thus prepared pSe1Bb1s-atoB-derived gene vector and pSe1Bb1s-nphT7-derived gene vector were treated with BamHI-XhoI restriction enzymes and then the DNA sequence of an atoDA-derived gene or a ctfAB-derived gene treated with BglII-XhoI restriction enzymes was inserted. The atoB-derived gene was derived from an *E. coli* K-12 MG1655 strain, the nphT7-derived gene was derived from a *Streptomyces* sp. strain, the atoDA-derived gene was derived from an *E. coli* K-12 MG1655 strain, and the ctfAB-derived gene and the adc-derived gene were derived from a *Clostridium aceto-* butylicum strain. All the genes introduced into the vectors were prepared by GENSCRIPT[R].

As a result, four vectors, i.e., a pSe1Bb1s-atoB-atoDA vector, a pSe1Bb1s-atoB-ctfAB vector, a pSe1 Bb1 s-nphT7-atoDA vector and a pSe1Bb1s-nphT7-ctfAB vector, were prepared and finally four acetone-producing vectors were prepared by treating with BamHI-XhoI and then inserting the DNA sequence of an adc gene treated with BglII-XhoI restriction enzymes: a pSe1Bb1s-atoB-atoDA-adc vector (SEQ ID NO 6), a pSe1Bb1s-atoB-ctfAB-adc vector (SEQ ID NO 7), a pSe1Bb1s-nphT7-atoDA-adc vector (SEQ ID NO 8) and a pSe1Bb1s-nphT7-ctfAB-adc vector (SEQ ID NO 9).

EXAMPLE 3

Preparation of Transformed *Synechococcus elongatus* Strain

The vectors of SEQ ID NOS 6-9 prepared in Example 2 were inserted into the neutral site I of a wild-type *Synechococcus elongatus* (*S. elongatus*) PCC7942 strain (PCC7942 (ATCC® 33912™)) by natural transformation (Golden et al. 1987, Grigorieva and Shestakov 1982). The transformation was confirmed by PCR (5'->3' primer sequence: forward (SEQ ID NO 10): CTGATTGTTCTAGGCGCTG/reverse (SEQ ID NO 11): TTTGGCAATCTGAAGACCCG).

EXAMPLE 4

Confirmation of Capability of Transformed *Synechococcus elongatus* Strain of Producing Acetone The transformed strain obtained in Example 3 was cultured under a carbon dioxide environment and it was investigated whether acetone was produced. Specifically, 100 mL of a BG-11 medium containing a 10 mM MOPS (3-morpholinopropane-1-sulfonic acid) buffer was added to a 100-mL bottle and the acetone-producing strain diluted to an optical density (O.D) of 0.6 initially was added. Then, after adding 10 μg/mL spectinomycin and 10 mM potassium acetate, incubation was performed under a condition of 30° C., 100 μE·m$^{-2}$·s$^{-1}$ and continuous supply of 5% $CO_2$. Since day 1 after the start of the incubation, 0.1 mM IPTG was added as an inducer necessary for gene expression. Optical density at 730 nm, acetate production, pH and acetone production were measured until day 5.

Figure 2A:
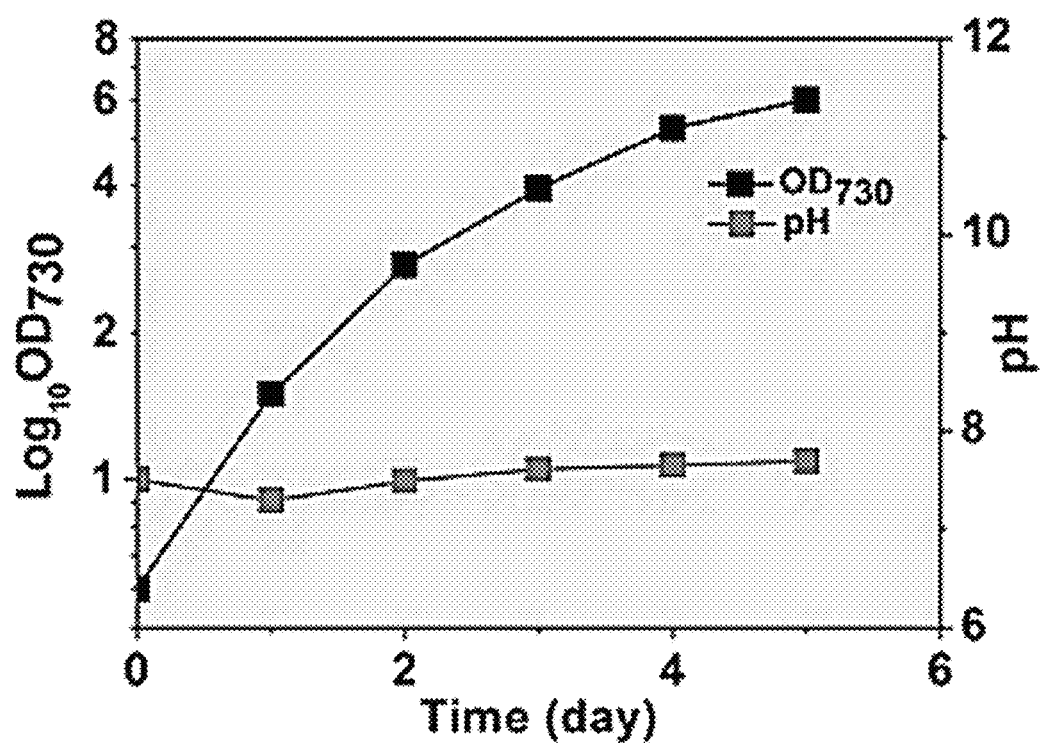
FIGS. 2A to 2C show the optical density (FIG. 2A), acetone production (FIG. 2B) and acetate production (FIG. 2C) of a *Synechococcus elongatus* strain transformed with a pSe1Bb1s-atoB-atoDA-adc vector.
Figure 2B:
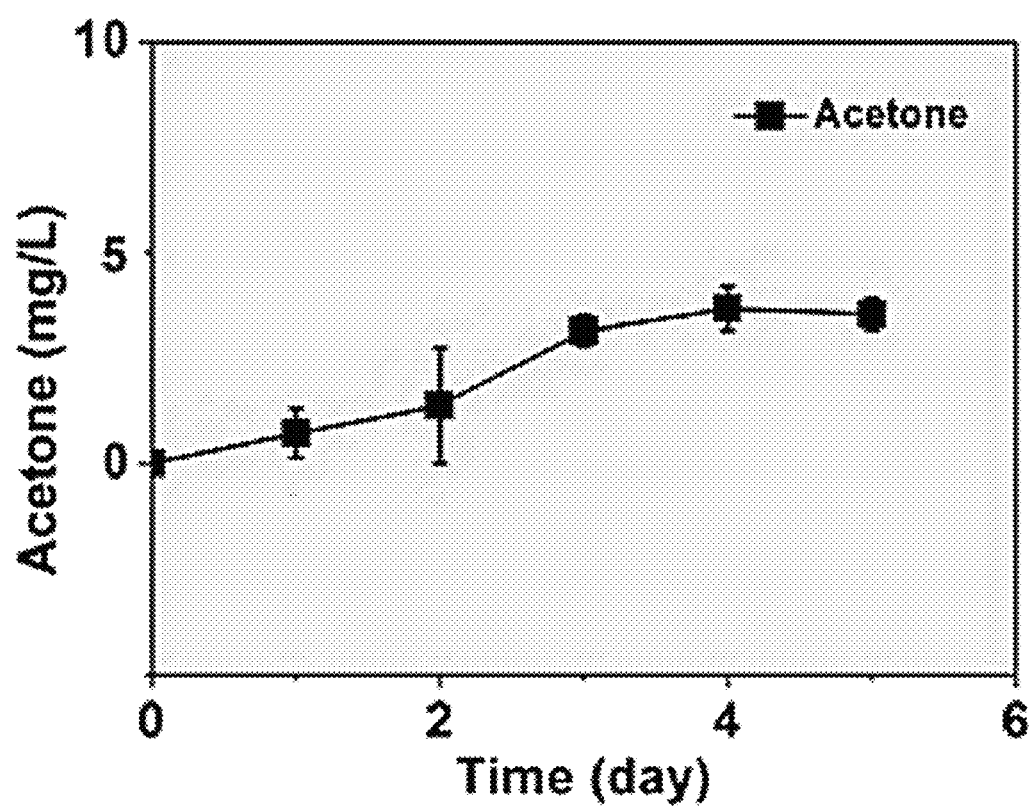
Figure 2C:
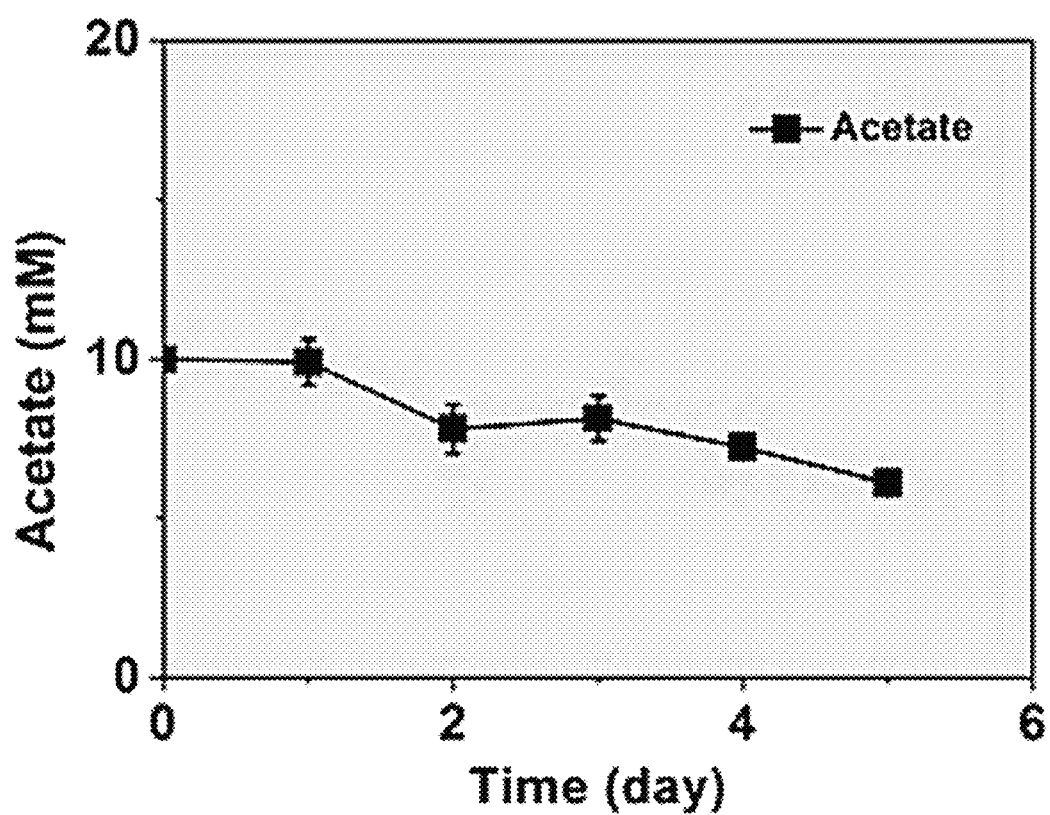
Figure 3A:
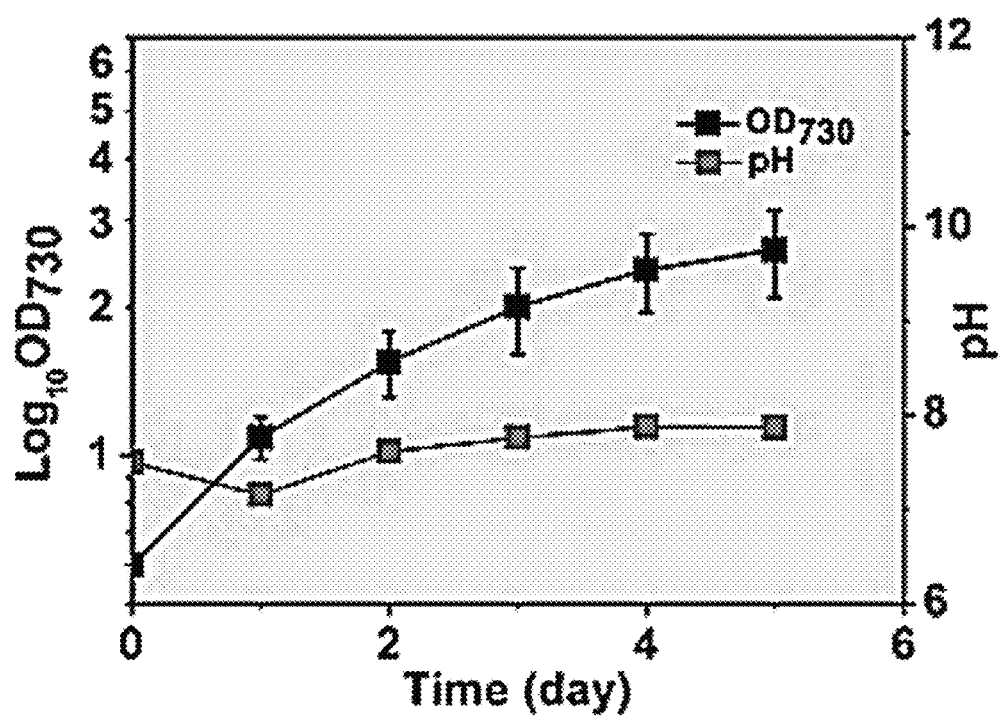
FIGS. 3A to 3C show the optical density (FIG. 3A), acetone production (FIG. 3B) and acetate production (FIG. 3C) of a *Synechococcus elongatus* strain transformed with a pSe1Bb1s-atoB-ctfAB-adc vector.
Figure 3B:
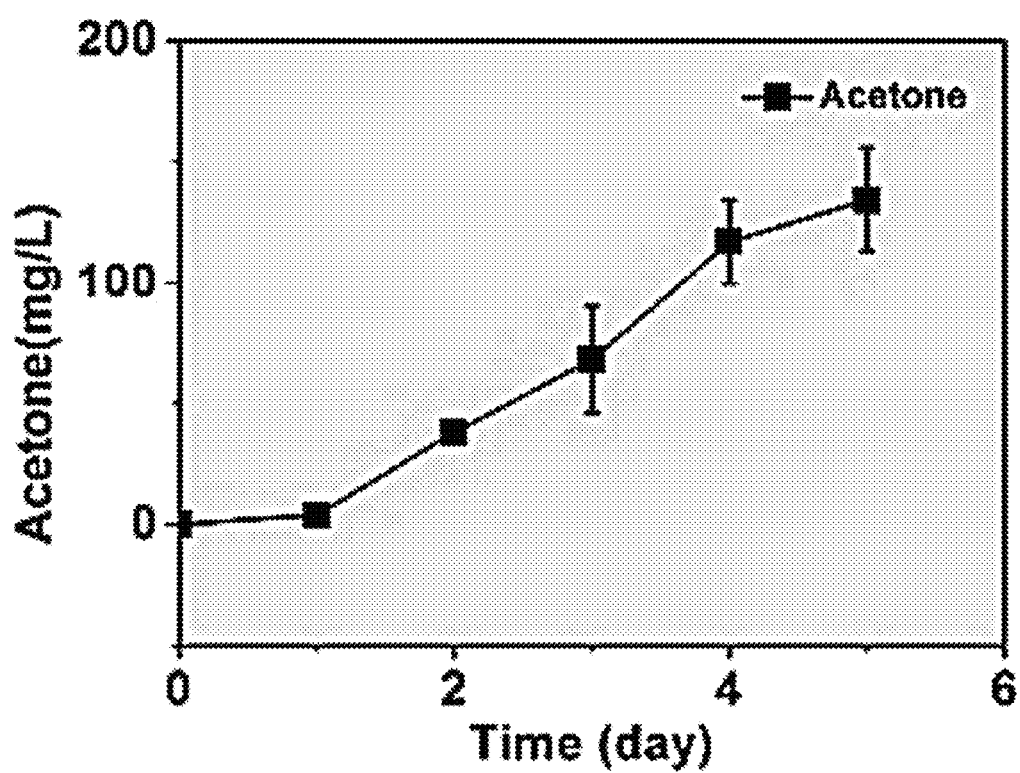
Figure 3C:
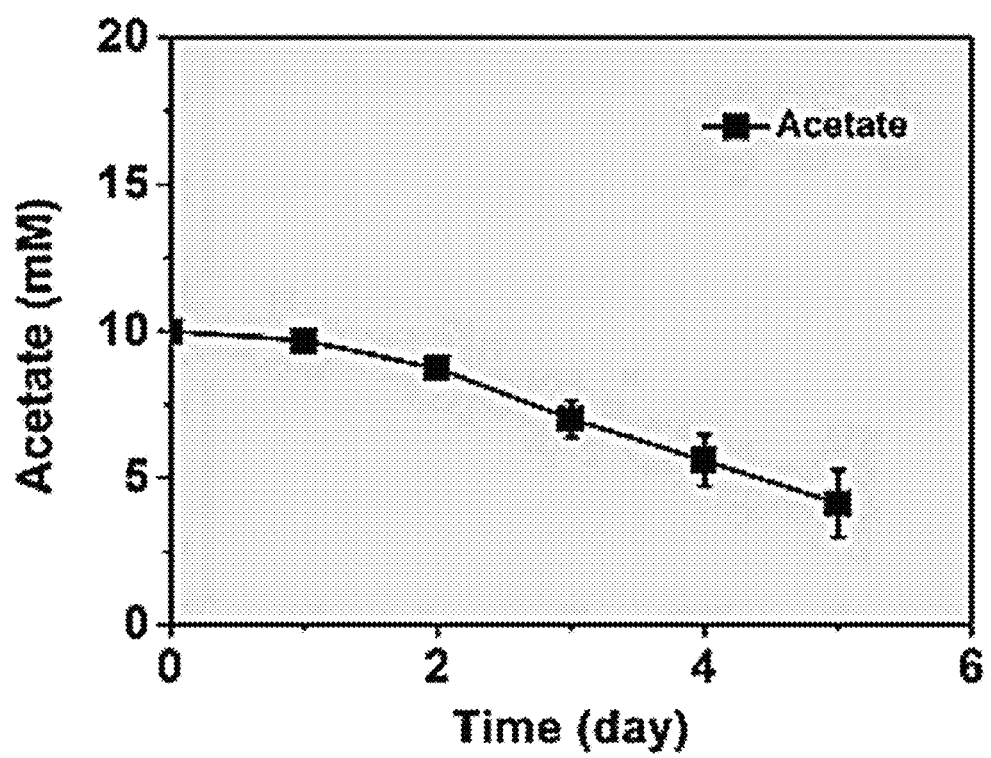
Figure 4A:
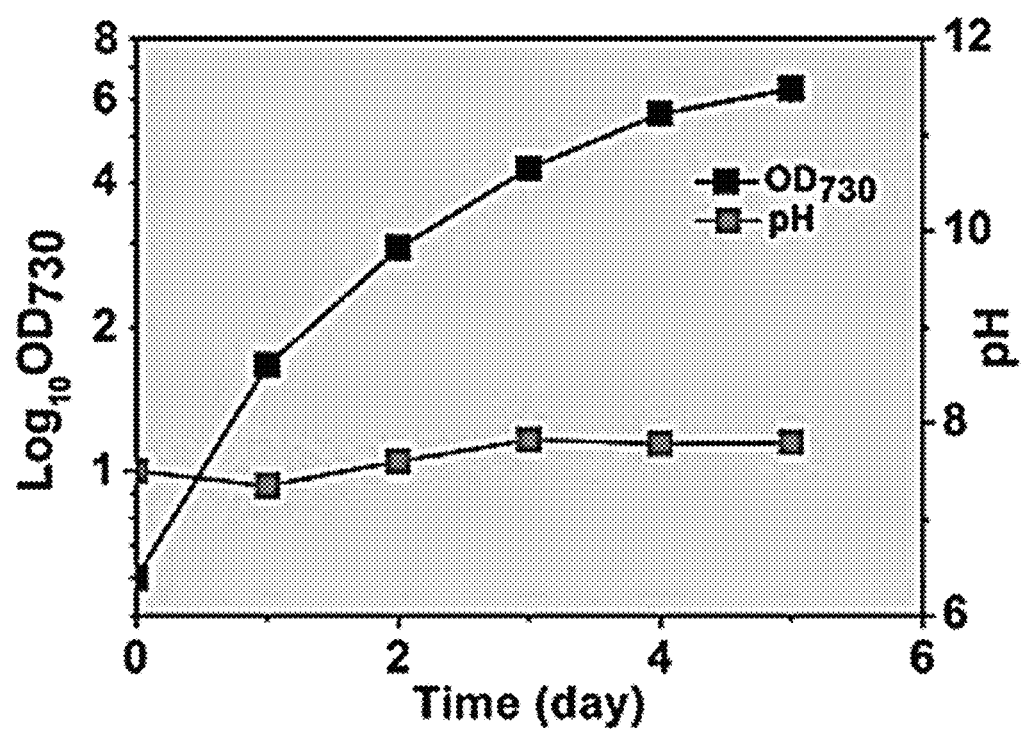
FIGS. 4a to 4c show the optical density (FIG. 4A), acetone production (FIG. 4B) and acetate production (FIG. 4C) of a *Synechococcus elongatus* strain transformed with a pSe1Bb1s-nphT7-atoDA-adc vector.
Figure 4B:
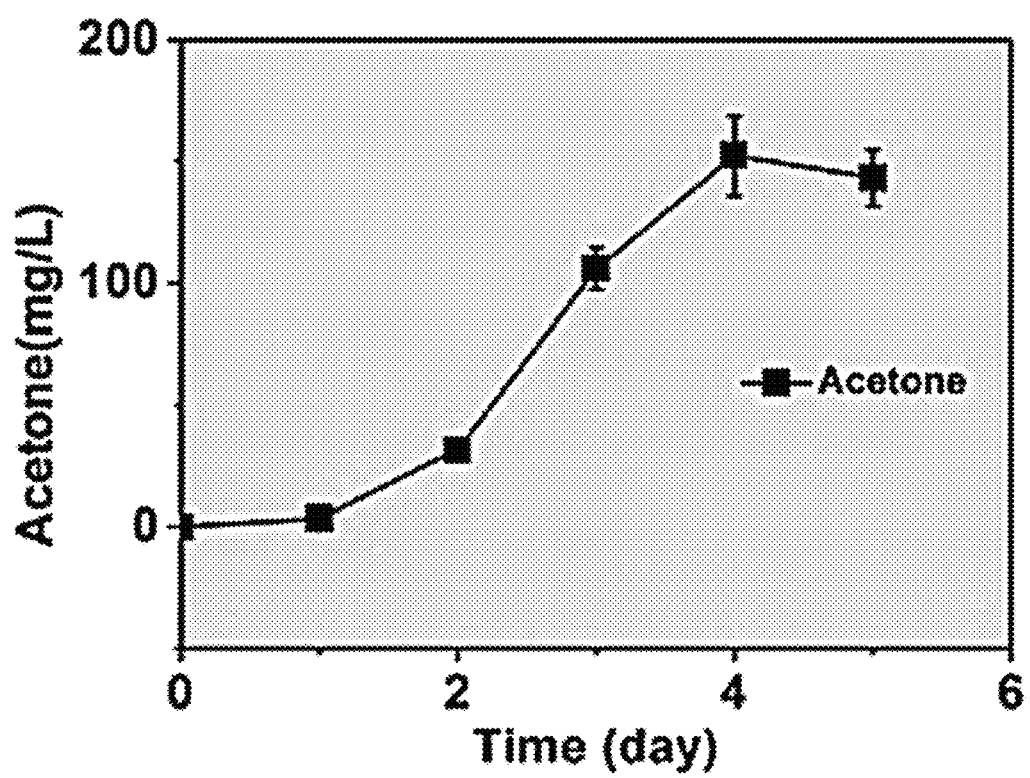
Figure 4C:
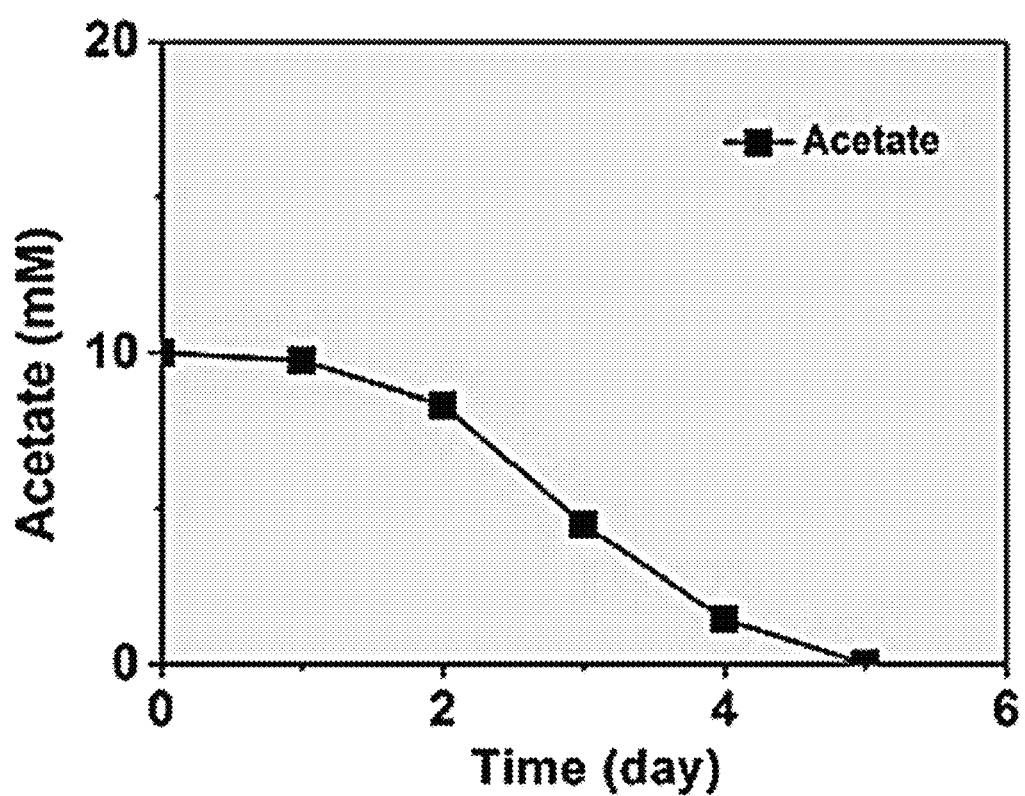
Figure 5A:
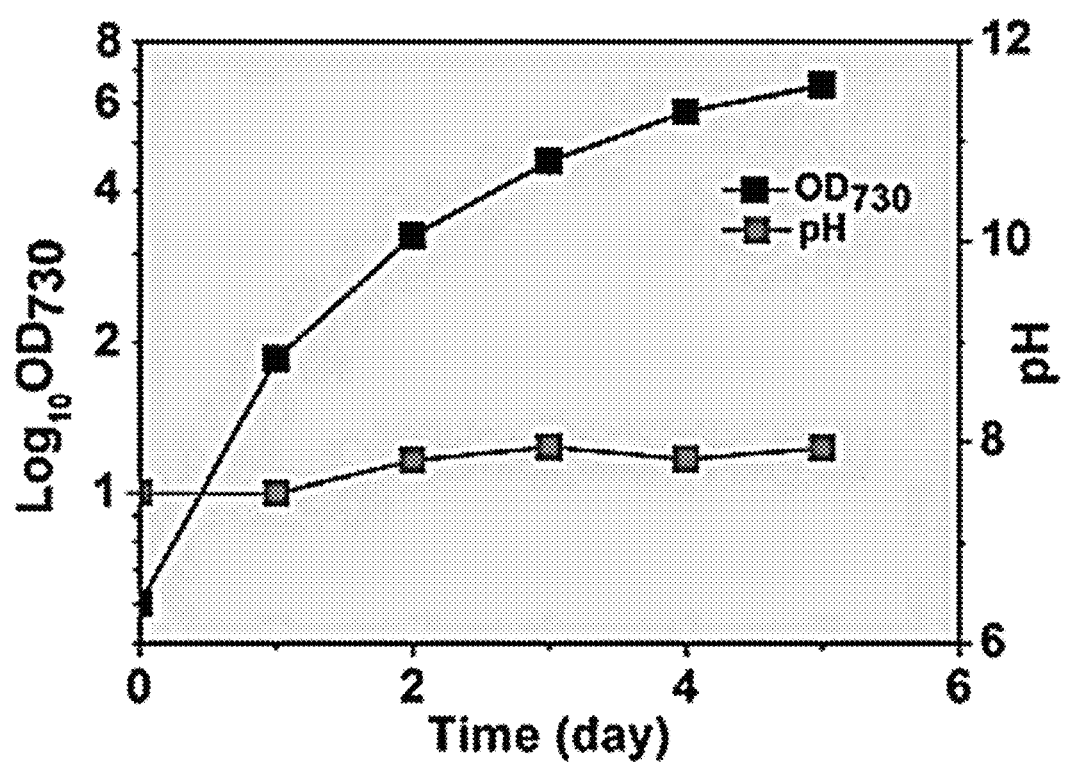
FIGS. 5A to 5C show the optical density (FIG. 5A), acetone production (FIG. 5B) and acetate production (FIG. 5C) of a *Synechococcus elongatus* strain transformed with a pSe1Bb1s-nphT7-ctfAB-adc vector.
Figure 5B:
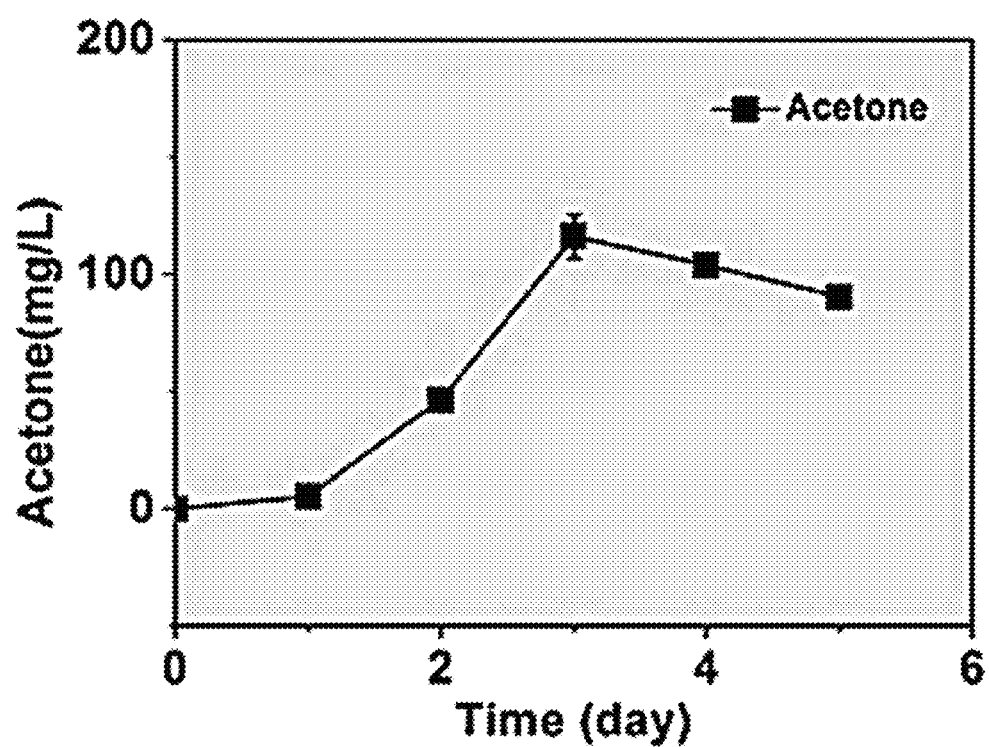
Figure 5C:
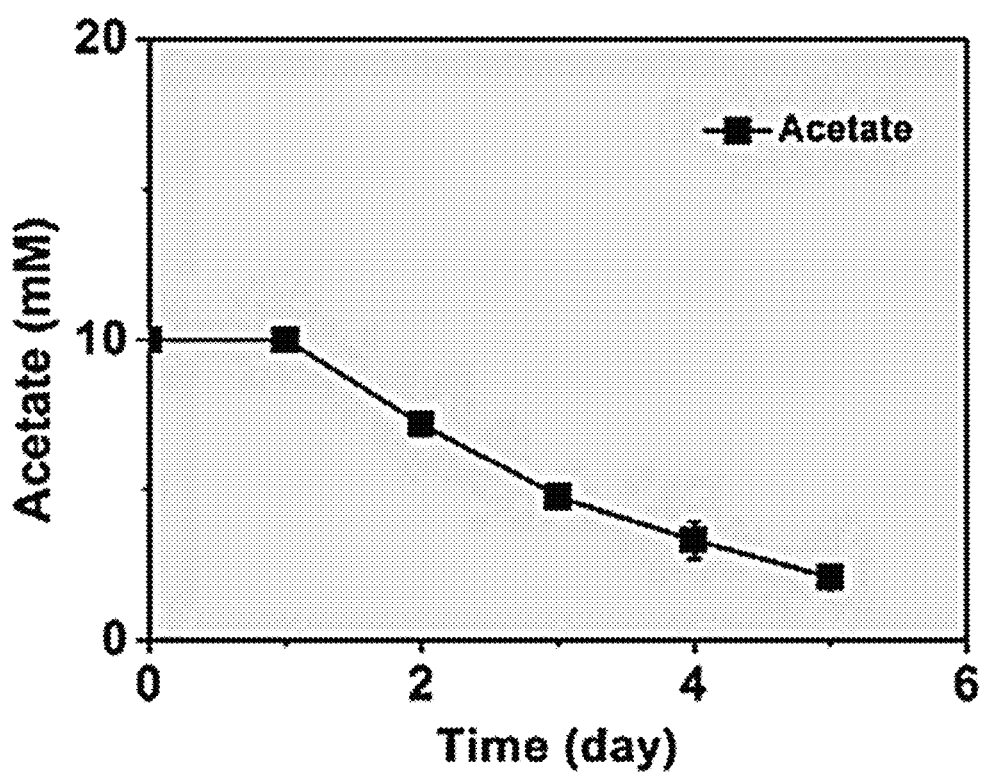

The strain transformed with the pSe1Bb1s-atoB-atoDA-adc vector (SEQ ID NO 6) produced 3.6 mg/L of acetone (FIG. 2b). The strain transformed with the pSe1Bb1s-atoB-ctfAB-adc vector (SEQ ID NO 7) produced 134 mg/L of acetone (FIG. 3b). The strain transformed with the pSe1Bb1s-nphT7-atoDA-adc vector (SEQ ID NO 8) produced 152 mg/L of acetone (FIG. 4b), and the strain transformed with the pSe1Bb1s-nphT7-ctfAB-adc vector (SEQ ID NO 9) produced 116 mg/L of acetone (FIG. 5b).

What is claimed is:

1. A *Synechococcus elongatus* strain being capable of enhanced production of acetone, wherein the strain comprises:
   one or more selected from a group consisting of:
   an acetyl-CoA transferase gene containing SEQ ID NO: 1 and an acetyl-CoA synthase gene contains SEQ ID NO: 2;
   an acetoacetyl-CoA transferase gene containing SEQ ID NO: 3 or SEQ ID NO: 4; and
   an acetoacetate decarboxylase gene containing SEQ ID NO: 5,
   wherein the strain produces acetone in a molar ratio of 0.8 or greater in the total product under a condition of 30° C. and 5% carbon dioxide.

2. The strain according to claim 1, wherein the strain is one transformed with a vector comprising: one or more selected from a group consisting of an acetyl-CoA transferase gene containing SEQ ID NO: 1 and an acetyly-CoA synthase gene containing SEQ ID NO: 2;
   an acetoacetyl-CoA transferase gene containing SEQ ID NO: 3 or SEQ ID NO: 4; and
   an acetoacetate decarboxylase gene containing SEQ ID NO: 5.

3. The strain according to claim 2, wherein the strain is *Synechococcus elongatus* PCC7942 transformed with the vector.

4. The strain according to claim 2, wherein the vector further comprises:
   a pUC replication origin as a replication origin;
   neutral sites located upstream and downstream of the replication origin;
   a spectinomycin resistance gene as a selection marker;
   a repressor selected from a group consisting of a lac I repressor, a tetR repressor and an AraC repressor;
   a promoter selected from a group consisting of a trc promoter, a tetA promoter or a modified tetA promoter, a BAD promoter and a cbbL promoter; and
   a BglII site, a BamHI site, an EcoRI site and an XhoI site as restriction enzyme sites.

5. The strain according to claim 4, wherein one or more selected from a group consisting of an acetyl-CoA transferase gene containing SEQ ID NO: 1 and an acetyl-CoA synthase gene containing SEQ ID NO: 2; an acetoacetyl-CoA transferase gene containing SEQ ID NO: 3 or SEQ ID NO: 4; and an acetoacetate decarboxylase gene containing SEQ ID NO: 5 are located between the BglII site and the BamHI site.

6. The strain according to claim 2, wherein the vector comprises a sequence from SEQ ID NOS: 6-9.

7. The strain according to claim 1, wherein the strain is a *Synechococcus elongatus* strain of accession number KCTC12758BP, KCTC12759BP, KCTC12760BP or KCTC12761BP.

8. The strain according to claim 1, wherein the strain absorbs and fixes carbon dioxide.

\* \* \* \* \*